(12) United States Patent
Forsell

(10) Patent No.: US 10,736,745 B2
(45) Date of Patent: *Aug. 11, 2020

(54) IMPLANTABLE LUBRICATION DEVICE AND METHOD OF TREATING A HUMAN OR MAMMAL PATIENT BY MEANS OF THE DEVICE

(71) Applicant: Peter Forsell, Bouveret (CH)

(72) Inventor: Peter Forsell, Bouveret (CH)

( * ) Notice: Subject to any disclaimer, the term of this patent is extended or adjusted under 35 U.S.C. 154(b) by 0 days.

This patent is subject to a terminal disclaimer.

(21) Appl. No.: 14/935,482

(22) Filed: Nov. 9, 2015

(65) Prior Publication Data

US 2016/0166387 A1 Jun. 16, 2016

Related U.S. Application Data

(63) Continuation of application No. 13/382,990, filed as application No. PCT/SE2010/050825 on Jul. 12, 2010, now Pat. No. 9,180,011.

(Continued)

(30) Foreign Application Priority Data

| Jul. 10, 2009 | (SE) | 0900957 |
|---|---|---|
| Jul. 10, 2009 | (SE) | 0900958 |
| Jul. 10, 2009 | (SE) | 0900959 |
| Jul. 10, 2009 | (SE) | 0900960 |
| Jul. 10, 2009 | (SE) | 0900961 |
| Jul. 10, 2009 | (SE) | 0900962 |

(Continued)

(51) Int. Cl.
*A61F 2/30* (2006.01)
*A61B 17/16* (2006.01)
(Continued)

(52) U.S. Cl.
CPC ...... *A61F 2/30756* (2013.01); *A61B 17/1666* (2013.01); *A61F 2/30* (2013.01);
(Continued)

(58) Field of Classification Search
CPC .................. A61F 2/30721; A61M 2005/1587
See application file for complete search history.

(56) References Cited

U.S. PATENT DOCUMENTS

| 5,681,289 A | * | 10/1997 | Wilcox | A61B 17/60 604/175 |
|---|---|---|---|---|
| 6,106,495 A | * | 8/2000 | Scott | A61B 17/88 604/506 |

(Continued)

*Primary Examiner* — Bruce E Snow
*Assistant Examiner* — Melissa A Hoban

(57) ABSTRACT

A lubrication device for lubricating a joint of a human or mammal patient, which is entirely implantable in a patient's body, comprises a reservoir for storing a lubricating fluid and a fluid connection for introducing the lubricating fluid into the joint when the device is implanted in the patient's body. Further, the fluid connection comprises a fluid connection device connecting the reservoir with the joint such that a lubricating fluid flow is established from the reservoir into the joint. The fluid connection comprises either an infusion needle adapted to be intermittently placed into the joint for injecting the lubricating fluid, or a tube adapted to be permanently placed into the joint for continuously injecting the lubricating fluid.

20 Claims, 35 Drawing Sheets

Related U.S. Application Data

(60) Provisional application No. 61/229,752, filed on Jul. 30, 2009, provisional application No. 61/229,755, filed on Jul. 30, 2009, provisional application No. 61/229,738, filed on Jul. 30, 2009, provisional application No. 61/229,739, filed on Jul. 30, 2009, provisional application No. 61/229,743, filed on Jul. 30, 2009, provisional application No. 61/229,745, filed on Jul. 30, 2009, provisional application No. 61/229,746, filed on Jul. 30, 2009, provisional application No. 61/229,747, filed on Jul. 30, 2009, provisional application No. 61/229,748, filed on Jul. 30, 2009, provisional application No. 61/229,751, filed on Jul. 30, 2009, provisional application No. 61/229,752, filed on Jul. 30, 2009, provisional application No. 61/229,761, filed on Jul. 30, 2009, provisional application No. 61/229,767, filed on Jul. 30, 2009, provisional application No. 61/229,778, filed on Jul. 30, 2009, provisional application No. 61/229,786, filed on Jul. 30, 2009, provisional application No. 61/229,789, filed on Jul. 30, 2009, provisional application No. 61/229,796, filed on Jul. 30, 2009, provisional application No. 61/229,735, filed on Jul. 30, 2009, provisional application No. 61/229,730, filed on Jul. 30, 2009, provisional application No. 61/229,733, filed on Jul. 30, 2009, provisional application No. 61/229,802, filed on Jul. 30, 2009, provisional application No. 61/229,805, filed on Jul. 30, 2009, provisional application No. 61/229,811, filed on Jul. 30, 2009, provisional application No. 61/229,815, filed on Jul. 30, 2009, provisional application No. 61/229,816, filed on Jul. 30, 2009, provisional application No. 61/229,731, filed on Jul. 30, 2009.

(30) Foreign Application Priority Data

| Jul. 10, 2009 | (SE) | ..................................... 0900963 |
| Jul. 10, 2009 | (SE) | ..................................... 0900964 |
| Jul. 10, 2009 | (SE) | ..................................... 0900965 |
| Jul. 10, 2009 | (SE) | ..................................... 0900966 |
| Jul. 10, 2009 | (SE) | ..................................... 0900967 |
| Jul. 10, 2009 | (SE) | ..................................... 0900968 |
| Jul. 10, 2009 | (SE) | ..................................... 0900969 |
| Jul. 10, 2009 | (SE) | ..................................... 0900970 |
| Jul. 10, 2009 | (SE) | ..................................... 0900971 |
| Jul. 10, 2009 | (SE) | ..................................... 0900972 |
| Jul. 10, 2009 | (SE) | ..................................... 0900973 |
| Jul. 10, 2009 | (SE) | ..................................... 0900974 |
| Jul. 10, 2009 | (SE) | ..................................... 0900975 |
| Jul. 10, 2009 | (SE) | ..................................... 0900976 |
| Jul. 10, 2009 | (SE) | ..................................... 0900977 |
| Jul. 10, 2009 | (SE) | ..................................... 0900978 |
| Jul. 10, 2009 | (SE) | ..................................... 0900979 |
| Jul. 10, 2009 | (SE) | ..................................... 0900980 |
| Jul. 10, 2009 | (SE) | ..................................... 0900981 |
| Nov. 24, 2009 | (WO) | ................. PCT/SE2009/000502 |

(51) Int. Cl.

| A61F 2/34 | (2006.01) |
| A61F 2/32 | (2006.01) |
| A61B 17/56 | (2006.01) |
| A61B 17/74 | (2006.01) |
| A61B 17/86 | (2006.01) |
| A61F 2/36 | (2006.01) |
| A61F 2/46 | (2006.01) |
| A61F 2/48 | (2006.01) |
| A61M 5/142 | (2006.01) |
| A61B 17/88 | (2006.01) |
| A61B 18/04 | (2006.01) |
| A61F 2/38 | (2006.01) |
| A61L 27/16 | (2006.01) |
| A61L 31/04 | (2006.01) |
| A61L 31/14 | (2006.01) |

(52) U.S. Cl.

CPC ............ *A61F 2/30721* (2013.01); *A61F 2/32* (2013.01); *A61F 2/34* (2013.01); *A61B 17/1604* (2013.01); *A61B 17/1637* (2013.01); *A61B 17/1664* (2013.01); *A61B 17/1668* (2013.01); *A61B 17/562* (2013.01); *A61B 17/74* (2013.01); *A61B 17/86* (2013.01); *A61B 17/8805* (2013.01); *A61B 18/04* (2013.01); *A61B 2018/046* (2013.01); *A61F 2/30942* (2013.01); *A61F 2/36* (2013.01); *A61F 2/3601* (2013.01); *A61F 2/3603* (2013.01); *A61F 2/389* (2013.01); *A61F 2/3859* (2013.01); *A61F 2/46* (2013.01); *A61F 2/4618* (2013.01); *A61F 2002/30065* (2013.01); *A61F 2002/3067* (2013.01); *A61F 2002/30471* (2013.01); *A61F 2002/30507* (2013.01); *A61F 2002/30558* (2013.01); *A61F 2002/30563* (2013.01); *A61F 2002/30565* (2013.01); *A61F 2002/30579* (2013.01); *A61F 2002/30583* (2013.01); *A61F 2002/30655* (2013.01); *A61F 2002/30668* (2013.01); *A61F 2002/30672* (2013.01); *A61F 2002/30673* (2013.01); *A61F 2002/30675* (2013.01); *A61F 2002/30754* (2013.01); *A61F 2002/30757* (2013.01); *A61F 2002/30759* (2013.01); *A61F 2002/30878* (2013.01); *A61F 2002/30886* (2013.01); *A61F 2002/3241* (2013.01); *A61F 2002/3483* (2013.01); *A61F 2002/3615* (2013.01); *A61F 2002/3631* (2013.01); *A61F 2002/4631* (2013.01); *A61F 2002/4635* (2013.01); *A61F 2002/4655* (2013.01); *A61F 2002/4677* (2013.01); *A61F 2002/482* (2013.01); *A61F 2002/485* (2013.01); *A61F 2250/00* (2013.01); *A61L 27/16* (2013.01); *A61L 31/042* (2013.01); *A61L 31/044* (2013.01); *A61L 31/046* (2013.01); *A61L 31/148* (2013.01); *A61L 2300/406* (2013.01); *A61L 2400/06* (2013.01); *A61L 2430/24* (2013.01); *A61M 5/14276* (2013.01); *A61M 2005/14284* (2013.01)

(56) References Cited

U.S. PATENT DOCUMENTS

| 6,387,098 B1* | 5/2002 | Cole ................. A61M 25/0108 |
| | | 606/62 |
| 6,454,696 B1* | 9/2002 | Kindlein ............. A61N 5/1007 |
| | | 600/7 |
| 9,039,661 B2* | 5/2015 | Becker ................ A61J 15/0015 |
| | | 604/174 |
| 9,265,610 B2* | 2/2016 | Forsell ................ A61F 2/30721 |
| 9,421,051 B2* | 8/2016 | Finley ................... A61B 17/844 |
| 2003/0018232 A1* | 1/2003 | Elliott ................ A61M 37/0069 |
| | | 600/1 |
| 2003/0069541 A1* | 4/2003 | Gillis ................. A61M 39/0208 |
| | | 604/164.01 |
| 2004/0176664 A1* | 9/2004 | Iddan ................. A61B 1/00156 |
| | | 600/160 |

(56) References Cited

U.S. PATENT DOCUMENTS

| | | | |
|---|---|---|---|
| 2004/0267375 A1* | 12/2004 | Friedrichs | A61F 2/30721 623/22.18 |
| 2006/0264897 A1* | 11/2006 | Lobl | A61M 39/0208 604/506 |
| 2007/0032878 A1* | 2/2007 | Bader | A61F 2/34 623/22.17 |
| 2007/0088442 A1* | 4/2007 | Cima | A61B 5/055 623/18.11 |
| 2007/0179609 A1* | 8/2007 | Goble | A61B 17/86 623/16.11 |
| 2007/0233019 A1* | 10/2007 | Forsell | A61M 5/14276 604/288.03 |
| 2007/0265680 A1* | 11/2007 | Liu | A61N 1/0502 607/46 |
| 2008/0177218 A1* | 7/2008 | McKay | A61B 17/56 604/19 |
| 2011/0196301 A1* | 8/2011 | Forsell | A61F 2/26 604/150 |
| 2013/0041353 A1* | 2/2013 | Shin | A61M 5/14248 604/892.1 |
| 2013/0253447 A1* | 9/2013 | Ball | A61M 5/14276 604/272 |

\* cited by examiner

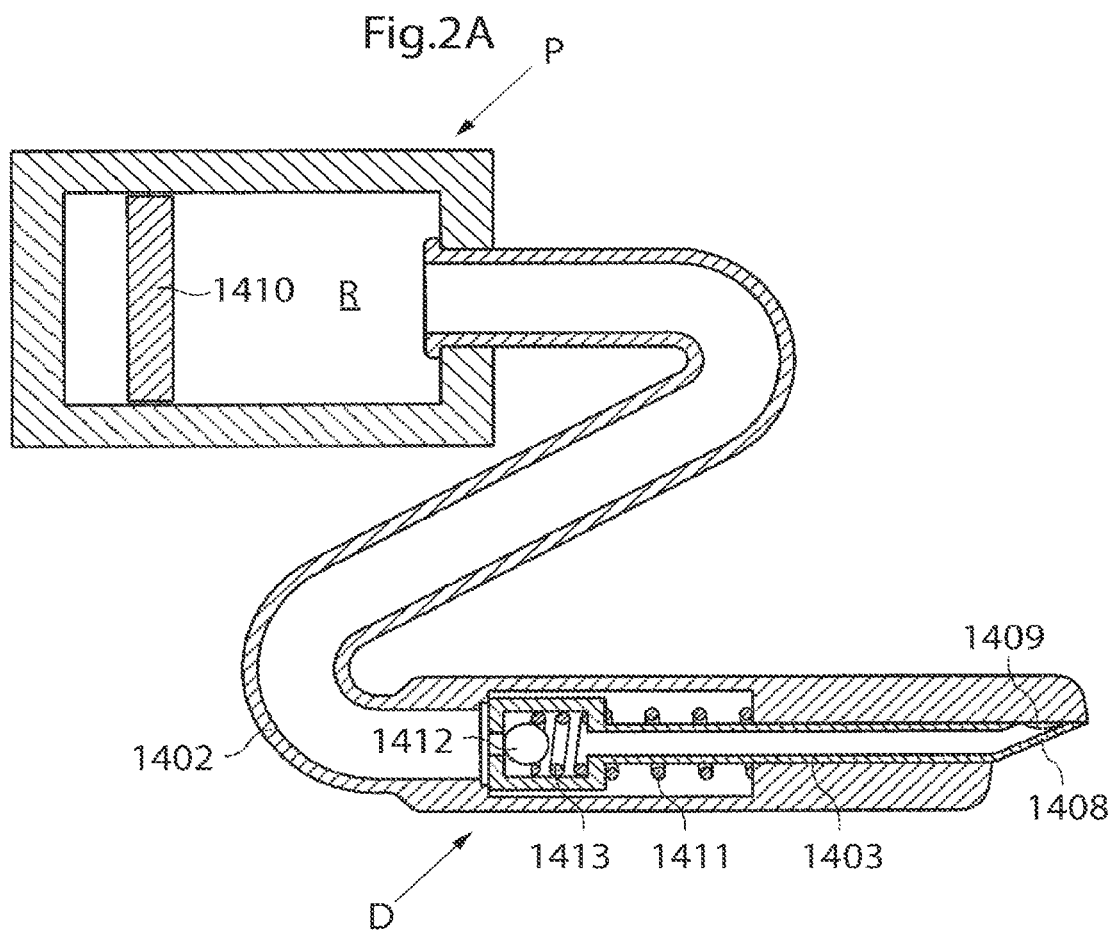
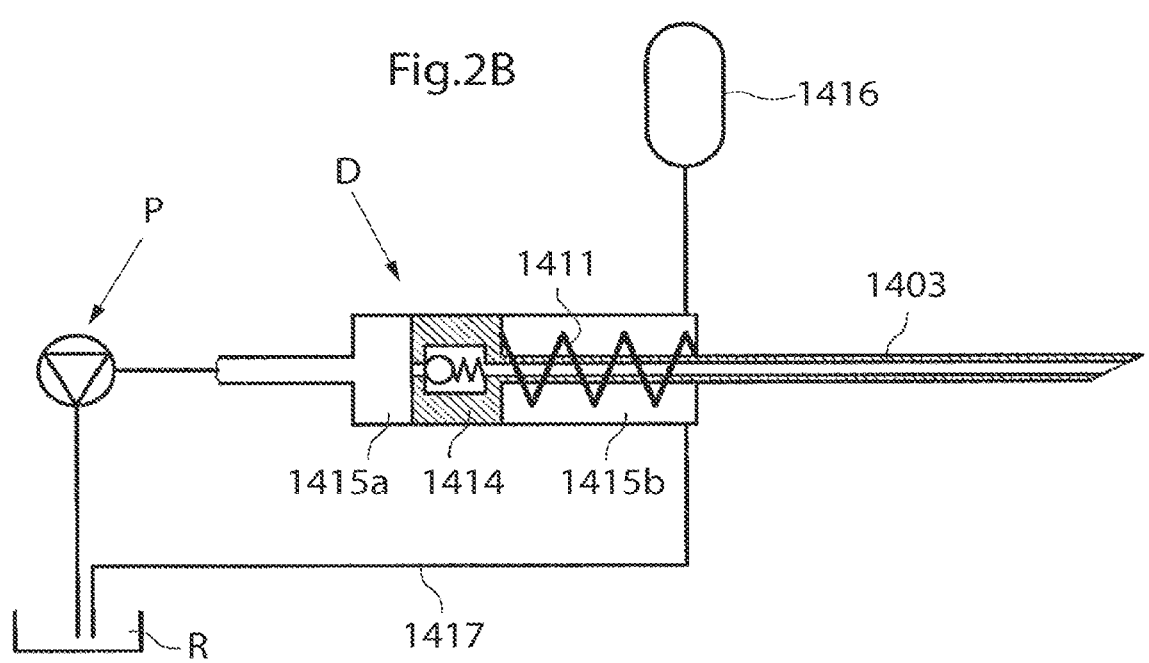

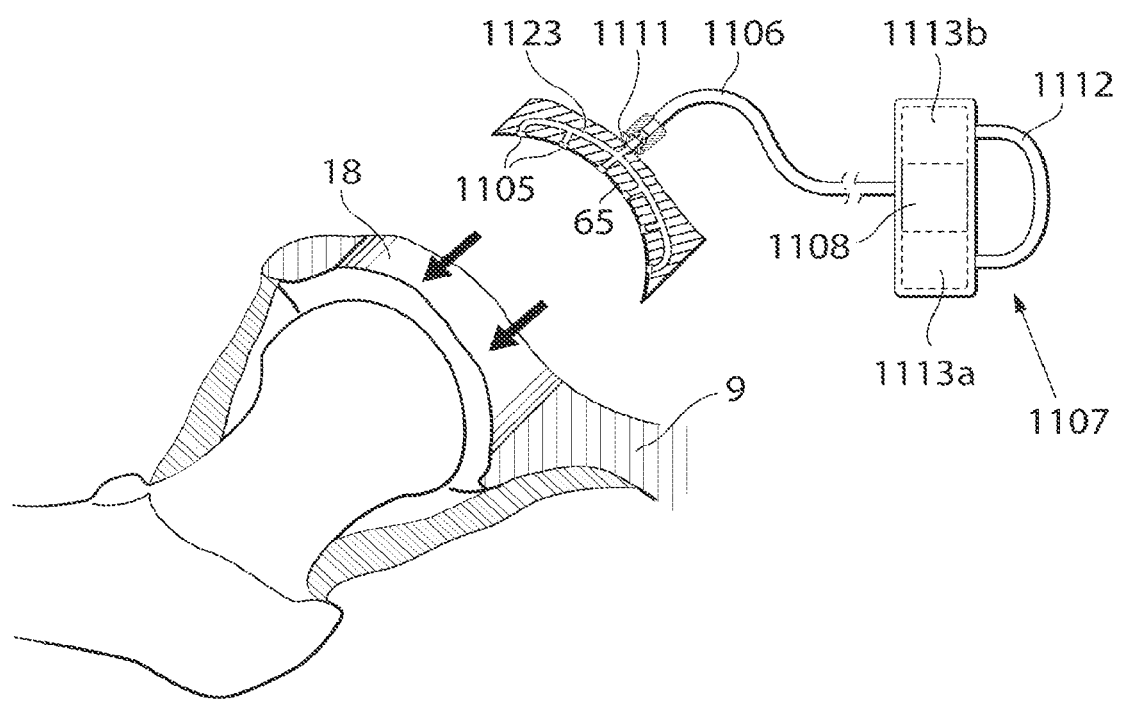

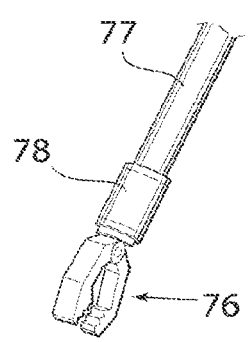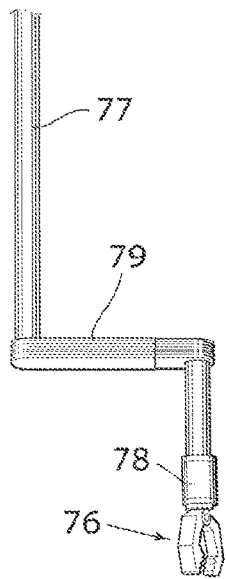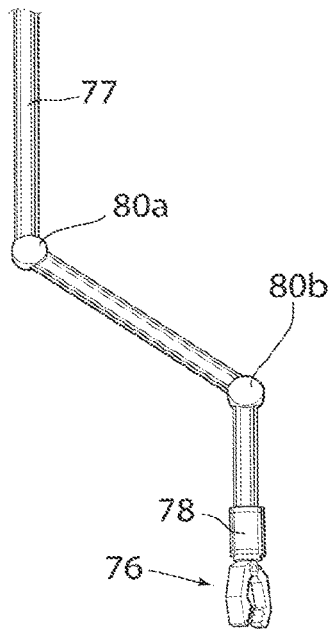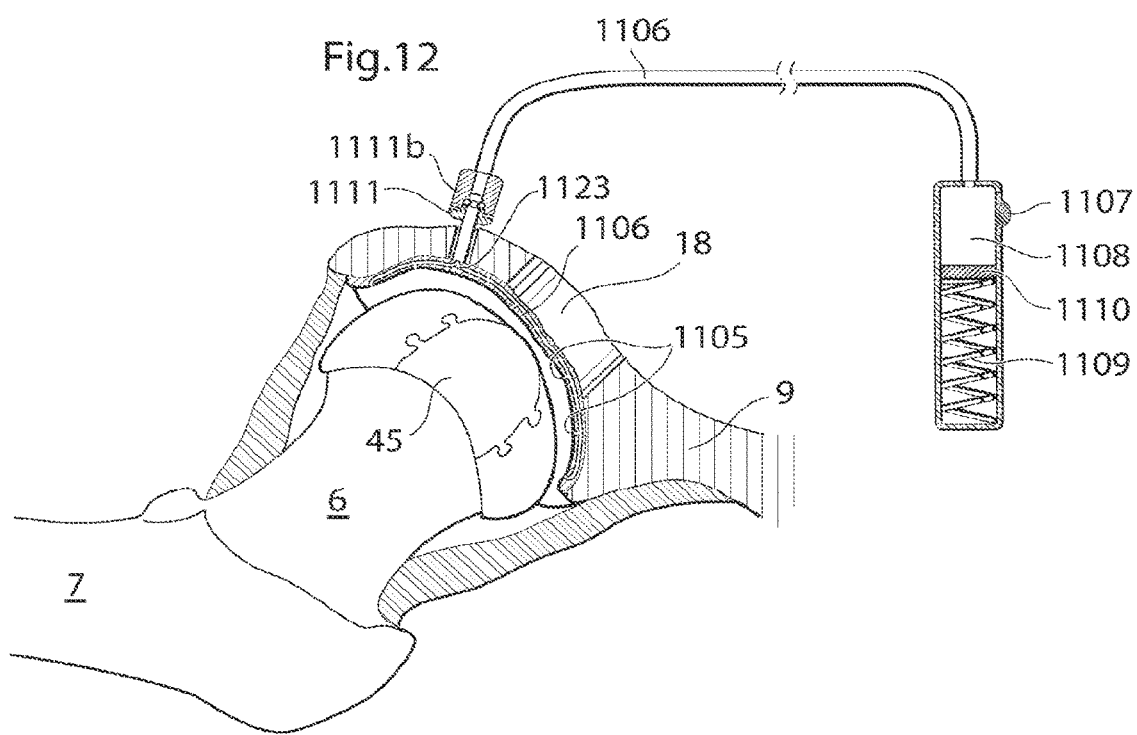

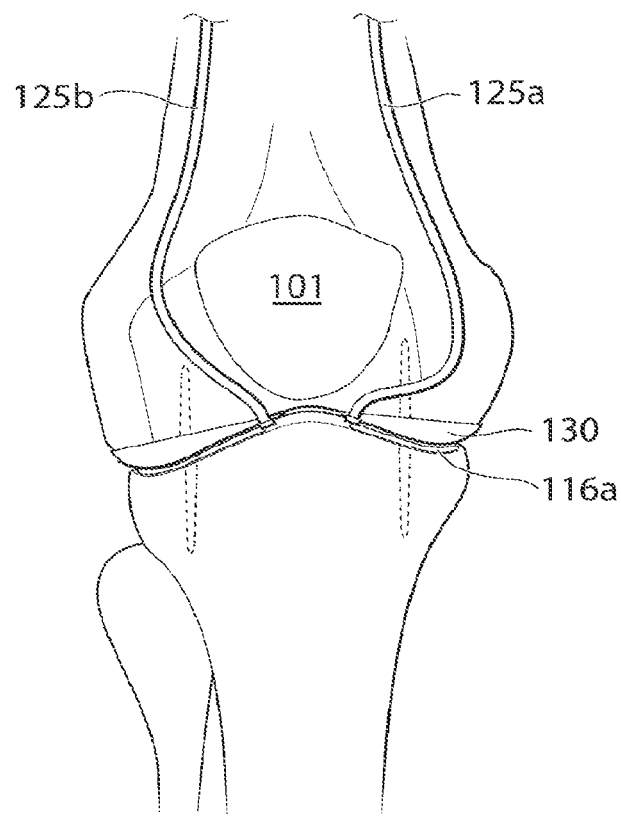
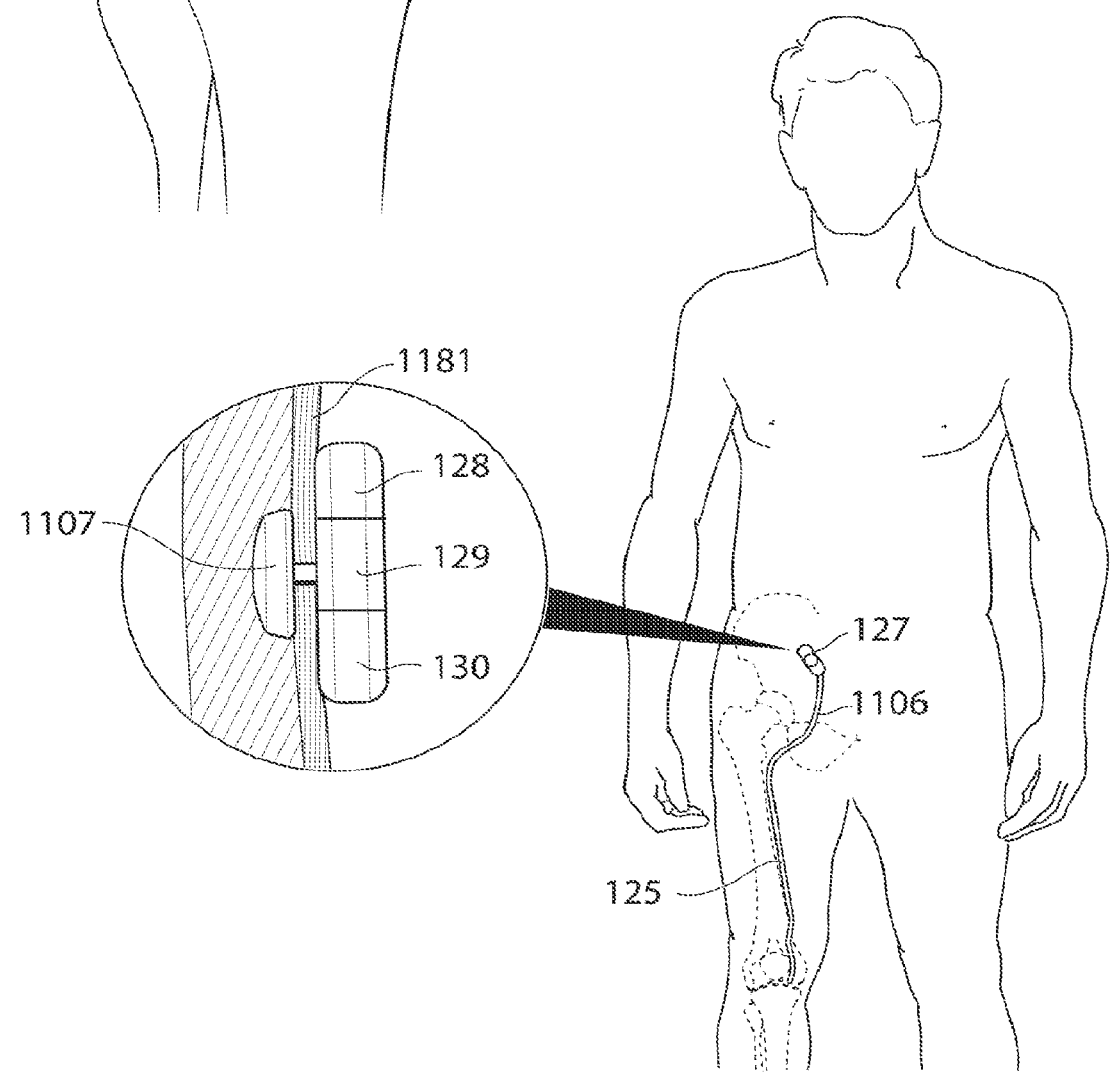

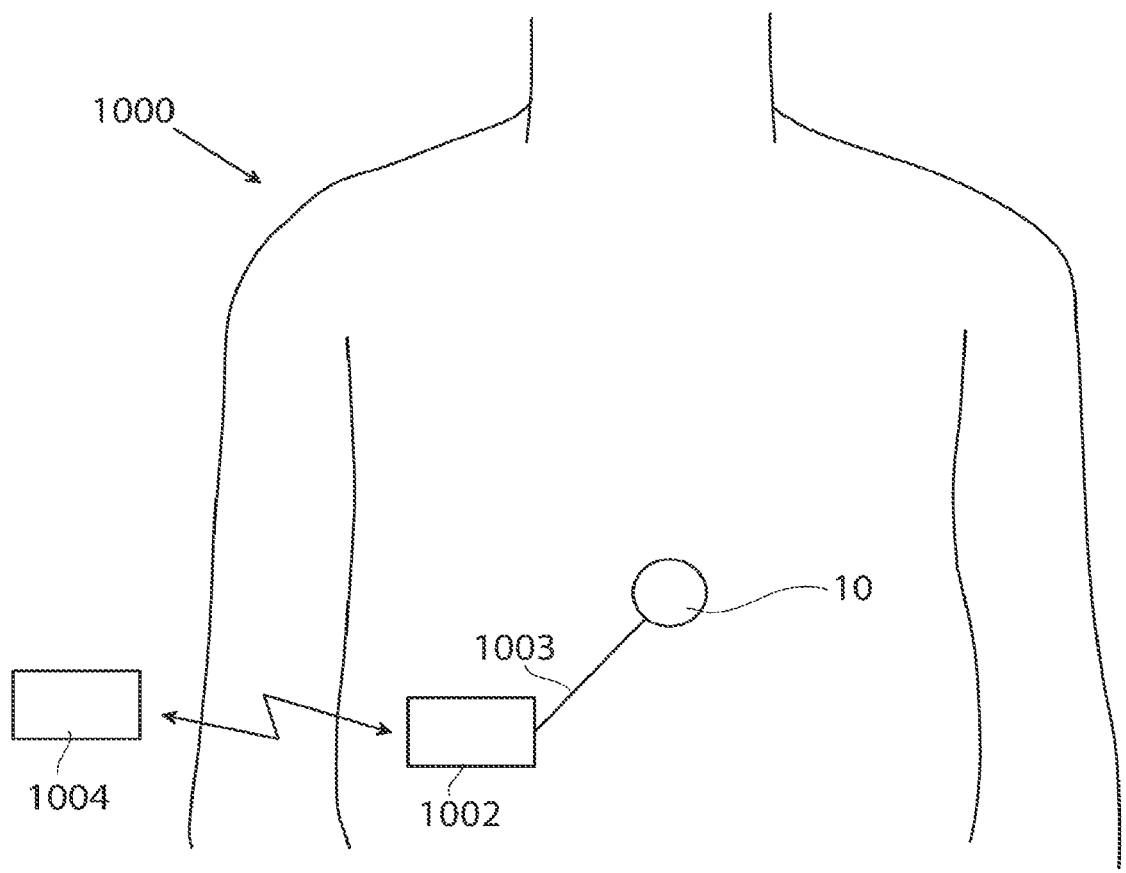

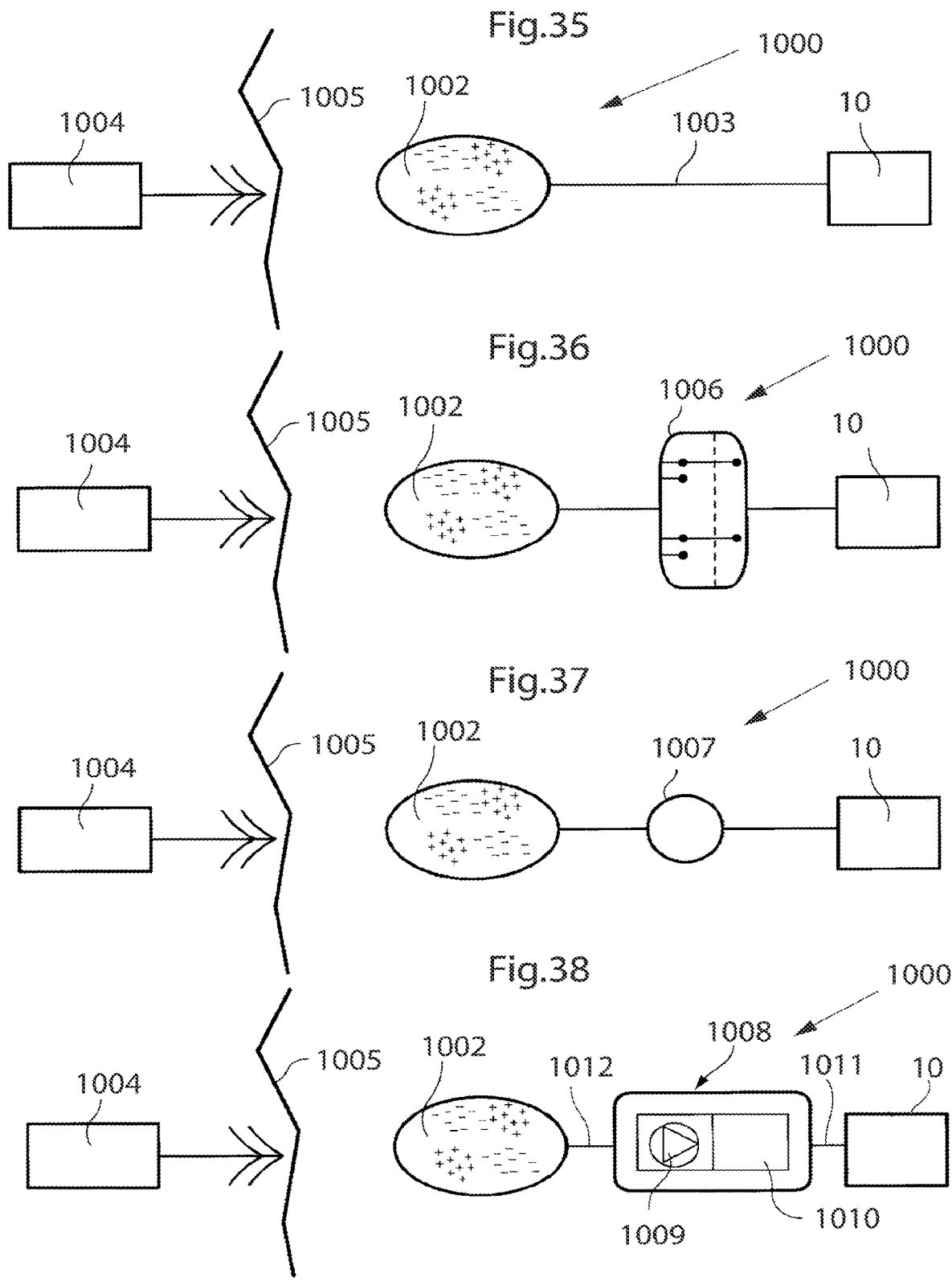

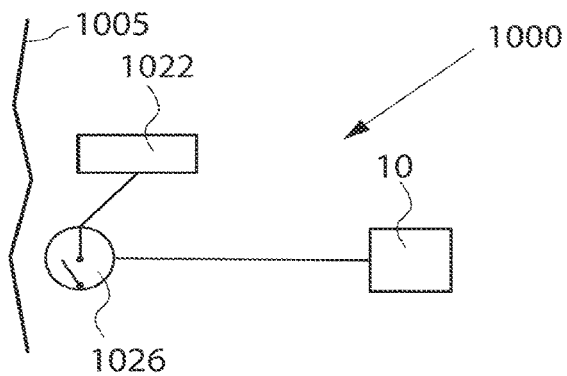
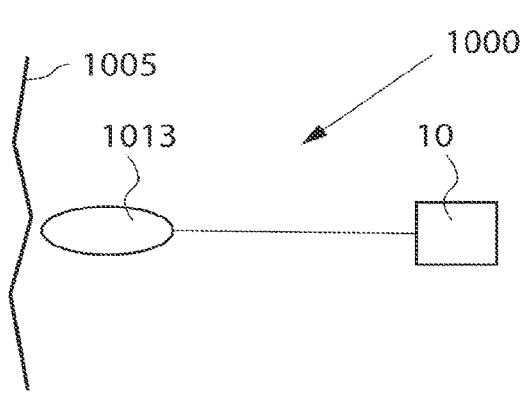
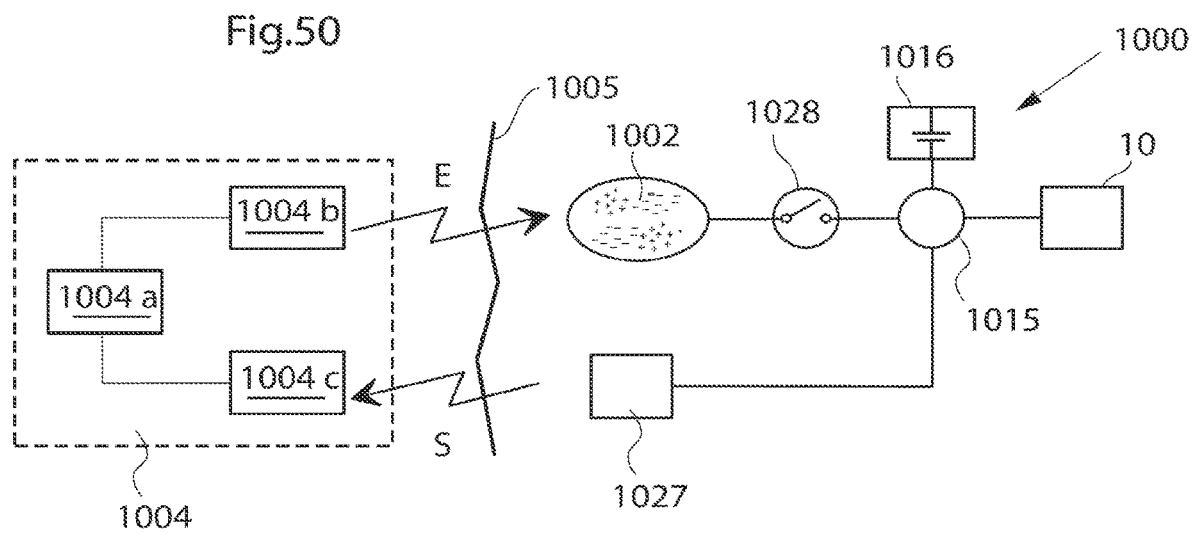

IMPLANTABLE LUBRICATION DEVICE AND METHOD OF TREATING A HUMAN OR MAMMAL PATIENT BY MEANS OF THE DEVICE

This application is a continuation of U.S. patent application Ser. No. 13/382,990 filed 9 Jan. 2012, which is the U.S. national phase of the International Application No. PCT/SE2010/050825, filed 12 Jul. 2010, which designated the U.S. and claims the benefit of U.S. Provisional Nos. 61/229,730 filed 30 Jul. 2009; 61/229,731 filed 30 Jul. 2009; 61/229,733 filed 30 Jul. 2009; 61/229,735 filed 30 Jul. 2009; 61/229,738 filed 30 Jul. 2009; 61/229,739 filed 30 Jul. 2009; 61/229,743 filed 30 Jul. 2009; 61/229,745 filed 30 Jul. 2009; 61/229,746 filed 30 Jul. 2009; 61/229,747 filed 30 Jul. 2009; 61/229,748 filed 30 Jul. 2009; 61/229,751 filed 30 Jul. 2009; 61/229,752 filed 30 Jul. 2009; 61/229,755, filed 30 Jul. 2009; 61/229,761 filed 30 Jul. 2009; 61/229,767 filed 30 Jul. 2009; 61/229,778 filed 30 Jul. 2009; 61/229,786 filed 30 Jul. 2009; 61/229,789 filed 30 Jul. 2009; 61/229,796 filed 30 Jul. 2009; 61/229,802 filed 30 Jul. 2009; 61/229,805 filed 30 Jul. 2009; 61/229,811 filed 30 Jul. 2009; 61/229,815 filed 30 Jul. 2009; 61/229,816 filed 30 Jul. 2009; and which claims priority to Swedish Application Nos. 0900981-2 filed 10 Jul. 2009; 0900957-2 filed 10 Jul. 2009; 0900958-0 filed 10 Jul. 2009; 0900959-8 filed 10 Jul. 2009; 0900960-6 filed 10 Jul. 2009; 0900961-4 filed 10 Jul. 2009; 0900962-2 filed 10 Jul. 2009; 0900963-0 filed 10 Jul. 2009; 0900964-8 filed 10 Jul. 2009; 0900965-5 filed 10 Jul. 2009; 0900966-3 filed 10 Jul. 2009; 0900967-1 filed 10 Jul. 2009; 0900968-9 filed 10 Jul. 2009; 0900969-7 filed 10 Jul. 2009; 0900970-5 filed 10 Jul. 2009; 0900971-3 filed 10 Jul. 2009; 0900972-1 filed 10 Jul. 2009; 0900973-9 filed 10 Jul. 2009; 0900974-7 filed 10 Jul. 2009; 0900975-4 filed 10 Jul. 2009; 0900976-2 filed 10 Jul. 2009; 0900977-0 filed 10 Jul. 2009; 0900978-8 filed 10 Jul. 2009; 0900979-6 filed 10 Jul. 2009; 0900980-4 filed 10 Jul. 2009 and PCT/SE2009/000502 filed 24 Nov. 2009, the entire contents of each of which are hereby incorporated by reference.

BACKGROUND

The present invention relates to an implantable lubrication device for lubricating a joint of a human or mammal patient, an implantable lubrication system and methods of treating a human or mammal patient by means of said implantable lubrication system.

The present invention is particularly suitable for long term or permanent introduction of lubricating fluid in a joint, i.e. for introduction of lubricating fluid on a permanent or periodical basis over long time intervals, e.g. over years.

The lubricating fluid (synovial fluid) reduces friction between the articular cartilage and other tissues in a joint and lubricates and cushions the bone and tissue components of the joint during movement. If the lubricating fluid is negatively affected and/or the joint articular cartilage usually covering the joint bone is damaged, in most cases due to older age and/or continuing extensive or abnormal strain on human or mammal joints (e.g. knee joint, hip joint), this can result in a degenerative joint disease (also known as osteoarthritis) characterized by a painful inflammation of the joint. Upon pathological reduction and change of composition of the lubricating fluid within the joint space, which consists of the articulating surfaces of the adjacent bones with the joint being stabilized and encompassed by the joint capsule and the synovial membrane, the lubricating fluid can no longer perform its usual task, i.e. lubrication of joint areas and shock absorption, together with the articular cartilage.

If the articular cartilage is also severely damaged due to osteoarthritis or the like and/or the synovial fluid is reduced or altered in its composition reducing its potential to lower friction within the joint, the articulating surfaces are subjected to high friction and increased wear causing a painful inflammation of the joint. This can result in serious restraints of movement, especially in walking and standing, which further augment degenerative processes of the joint. Degenerative joint disease is highly prevalent in the western world, with this disease being one of the leading causes for chronic disability in Europe and the US.

Patients with osteoarthritis require a regular long term treatment by which lubricating fluid is introduced into the affected joint, which, on the one hand, restores the physiological functionality of the damaged joint as far as possible and, on the other hand, involves as little extra stress as possible—both physical and psychological—for the patient.

A known standard therapy is periodical extracorporeal injection of synthetic lubricating fluid into the joint space by a syringe in order to substitute the absent physiological lubricating fluid. In such conventional treatment it is inconvenient for the patient to deliver the lubricating fluid at regular time intervals through the skin and the joint capsule into the joint by way of a syringe. Also, this may cause injuries to the skin and the joint capsule, which increases the risk of severe infections of the delicate joint tissues. Therefore, an injection may not be performed more often than every half a year.

However, many patients need a replenishment of lubricating fluid more often, i.e. a continuous replenishment of small amounts of lubricating fluid.

SUMMARY

An object is therefore to suggest an improved technique for lubricating a damaged or worn out joint of a human or mammal patient that, on the one hand, sufficiently lubricates the joint and, on the other hand, has a minimal infection risk.

The implantable lubrication device at least comprises, firstly, a reservoir that stores a lubricating fluid and, secondly, a fluid connection that introduces the stored lubricating fluid into the damaged joint when the lubrication device is implanted in a patient's body. The lubricating device can be completely implanted into the patient's body such that a damaged joint can post-operatively be appropriately lubricated from within the patient's body. This significantly reduces the infection risk for the patient and permits a post-operative supply of lubricating fluid to the damaged joint, continuously, intermittently, periodically or as required, e.g. depending on a fluid level within the joint.

An implanted lubrication system according to the present invention comprises the implanted lubrication device and a lubricating fluid stored in its reservoir which is introduced into the joint by means of its fluid connection.

Further compulsory or optional components of the implantable lubrication device, such as a reservoir, a pump or motor, an energy source, a control unit, may also be fully implemented within a patient's body. Such components may belong to the implantable infusion device or form an integral part of the implantable lubrication system separate from the actual implantable infusion device. Since the implantable lubrication device is entirely implantable in the patient's body, i.e. the implanted lubrication system provides both a functionality for storing and a functionality for transporting lubricating fluid within the patient's body, the complete flow path of the lubricating fluid for lubricating the joint lies within the patient's body. Hence, there is no longer a need for extracorporeal injections into the joint.

The fluid connection comprises a fluid connection device that connects the reservoir of the implantable infusion device to the joint, thus establishing a flow path for the lubricating fluid from the reservoir into the joint. The fluid connection device is also fully implantable and preferably consists of a flexible tube or the like that is suitable for post-operatively transporting the lubricating fluid stored in the reservoir to the joint.

Further, the fluid connection comprises an infusion member connected to the fluid connection device. The infusion member may be introduced into the patient's body in close relation to or inside the joint during a surgery, such that, post-operatively, the lubricating fluid can be introduced into the joint. It may be arranged to intermittently inject lubricating fluid into the joint, e.g. periodically or if the fluid level falls below a predetermined threshold, e.g. upon actuation by a drive mechanism and dependent on sensor data. Alternatively and preferably, the infusion member may also be arranged to continuously inject lubricating fluid into the joint, e.g. a predetermined amount of lubricating fluid per time unit, e.g. one drop per hour or the like.

An intermittent or periodical injection may be achieved e.g. by an infusion needle that is placed in close relation to the joint during a surgery such that post-operatively it may be intermittently advanced into the joint in the right position and retracted thereafter by a drive mechanism, thereby allowing intermittent lubrication of the joint through a tip end of the infusion needle. The drive mechanism is configured for advancing and retracting the tip end of the infusion needle into and out of the joint. While the drive mechanism may be separate from the infusion needle and/or the fluid connection device, it is nevertheless arranged as an integral part of the implantable lubrication device such that it is entirely implanted into the patient's body.

Alternatively, the infusion member may comprise an infusion tube that is permanently placed in the joint in order to continuously introduce lubricating fluid into the joint. In this case a separate drive mechanism for advancing/retracting an infusion needle is not needed, since the infusion tube may be of a reasonably soft material that does not, or not appreciably, disturb the normal operation of the joint. Therefore, the infusion tube may lie within the joint on a permanent basis, such that lubricating fluid may be continuously inserted into the joint space.

Preferably, the reservoir of the implantable lubrication device comprises a reservoir coupled to the fluid connection device for storing the lubricating fluid. Typically the lubricating liquid is contained in the reservoir. The reservoir may be arranged as a separate part of the implantable lubrication device, which has to be separately implanted in the patient's body. In order to establish a proper fluid flow of lubricating fluid into the joint, the reservoir may be adapted to change its volume for creating an adequate pressure within the fluid connection device and the infusion member to transport the lubricating fluid into the joint.

Therefore, at least a portion of a periphery of the reservoir may comprise a flexible outer wall for changing the volume of the reservoir by deformation of the flexible material as the lubricating fluid is filled into or drawn out of the reservoir and for causing a fluid flow from the reservoir to the joint through the fluid connection device.

Thus, the reservoir may be of balloon type. The flexible material may comprise a polymer membrane. A bellows construction is preferable having pre-bent creases to reduce long term degradation. Drawing liquid from the reservoir into the fluid connection device and to the joint may cause a pressure decrease in at least part of the reservoir so that a negative pressure is attained as compared to the pressure in front of the infusion needle or the infusion tube at the joint end of the fluid connection device. For instance, the reservoir may comprise a gas chamber and a liquid chamber, said chambers being separated by a membrane, e.g. the polymer membrane, and act as a spring for changing the volume of the reservoir, such that the pressure in the gas chamber will decrease when lubricating liquid is drawn from the liquid chamber into the fluid connection device.

The reservoir may also have a refill injection port for refilling lubricating liquid from outside the human body into the implanted reservoir. The reservoir implanted in the patient's body along with the fluid connecting device may thus be kept small since the reservoir can be refilled easily at appropriate time intervals. Preferably, the injection port comprises a self-sealing material in respect of penetrations caused by a replenishing syringe that would be typically used to refill the reservoir through the patient's skin. It is preferable to implant the reservoir of the lubrication device, or at least the self-sealing injection port of the reservoir, subcutaneously in the patient's body so that it is easily accessible for refill by means of the syringe.

While the reservoir may be compressed manually in order to introduce lubricating fluid through the fluid connection device and the infusion needle or infusion tube into the patient's joint, it is preferred to connect a pump to said fluid connection device and couple it between the reservoir and the infusion member for pumping the lubricating fluid from the reservoir into the joint. By means of the pump, it is easy to measure out an exact dose of the lubricating fluid and thereby supply an appropriate amount of lubricating fluid into the joint in a continuous or intermittent way.

The implantable pump preferably comprises a valve device having a first and a second valve member, each of the said first and second valve members having a smooth surface facing each other so as to form a sealing contact between the first and second valve members and further having different liquid channels that can be brought into alignment by displacement of the two smooth surfaces relative to one another while maintaining the sealing contact. This type of pump is described in great detail in WO 2004/012806 A1. The first and second valve members are preferably made from a ceramic material for its excellent sealing capabilities over a long period of time and its inertness to many substances. The pump may be a membrane type pump, as also described in WO 2004/012806 A1, but is not restricted to this type of pump. The membrane type pump may comprise a membrane displaceable by a piston as the piston moves, the piston being coupled to the valve device so as to slidably displace the first and second valve members relative to one another as the piston moves.

Preferably, manual actuation of either the pump or the drive mechanism simultaneously causes actuation of the other, i.e. the drive mechanism or the pump. For instance, the pressure built up by the pump may cause the drive mechanism to advance the infusion needle and when the infusion liquid has been delivered through the tip end of the needle into the patient's body, the pressure relief in the pump will allow a return spring or other resilient means to retract the infusion needle.

The implanted pump may be actuated by mechanical remote control, by a pressure sensitive switch arranged so as to be manually operable when implanted subcutaneously in the patient's body, or by a sensor mechanism that measures the fluid level in the joint and actuates the pump (and the drive mechanism for advancement and/or retraction of the infusion needle) and actuates the pump if the measured fluid level falls below a predetermined threshold. Preferably, actuation of either the pump or the drive mechanism simultaneously causes actuation of the other, i.e. the drive mechanism or the pump. For instance, the pressure built up by the pump may cause the drive mechanism to advance the infusion needle and when the lubricating liquid has been delivered through the tip end of the infusion needle into the patient's body, the pressure relief in the pump will allow a return spring or other resilient means to retract the infusion needle.

For actuating the pump and, if utilized, a drive mechanism for advancing and/or retracting an infusion needle into/out of the joint, and for directly or indirectly causing a lubricating fluid flow into the joint within said lubrication device, at least one motor may be provided. The motor may be arranged e.g. for electrically, magnetically or electromagnetically actuating the pump and/or drive mechanism or for hydraulically actuating the pump and/or drive mechanism. Preferably, the motor is arranged for actuating either the pump or the drive mechanism, thereby causing simultaneous actuation of the other, i.e. the drive mechanism or the pump. A motor may also be provided for actuation of any other energy consuming part of the infusion device.

The term "motor" in the sense of the present invention includes anything that employs energy other than manual power and either automatically transforms such energy into kinetic or hydraulic or another type of energy or directly uses such energy to activate the pump, drive mechanism and/or other parts of the implanted lubricating device. As such, it is possible that part of the drive mechanism also forms a part of the motor, e.g. in the case of an electromagnetically actuated drive mechanism.

The motor forms part of the lubricating device and is implanted within the patient's body either separate from the body of the lubricating device for remote implantation within the patient's body or contained in the body of the lubrication device. Coupling elements may be provided either for conductive or for wireless energy transfer from outside the device to the motor. For instance, the motor may be arranged for being wirelessly driven by an external electromagnetic field. It is also possible to use an external energy source for use outside the patient's body, such as a primary energy source or a battery, in particular a rechargeable battery, that is mounted on the patient's skin to provide energy to the pump and/or drive mechanism and/or any other energy consuming part of the lubrication device. The energy source may in particular be connected to the at least one motor for actuating these components. An external energy source for wireless energy transfer may be adapted to create an external field, such as an electromagnetic field, magnetic field or electric field, or create a wave signal, such as an electromagnetic wave or sound wave signal.

Where the energy is wirelessly transferred to the implanted lubrication device, a transforming device for transforming the wirelessly transferred energy into electric energy may be provided. Such transforming device is preferably adapted to be placed directly under the patient's skin so as to minimize the distance and the amount of tissue between the transforming device and the energy supply means outside the patient's body.

An energy transmission device for wireless energy transfer from the energy source and/or energy storage means to the transforming device may be adapted to generate an electromagnetic field. Alternatively or in addition, the energy transmission device for wireless energy transfer may be adapted to generate a magnetic field. Also, the energy transmission device for wireless energy transfer may be adapted to generate an electric field. The wireless energy may also be transmitted by the energy transmission device by at least one wave signal. Such signal may comprise an electromagnetic wave signal, including at least one of an infrared light signal, a visible light signal, an ultraviolet light signal, a laser signal, a microwave signal, a radio wave signal, an X-ray radiation signal and a y-radiation signal. Also, the wave signal may comprise a sound or ultrasound wave signal. Furthermore, the wireless energy may be transmitted as a digital or analog signal or a combination thereof.

Instead of or in addition to an external energy source, the implantable lubrication device may itself be provided with an energy source. Such energy source may be part of or may be contained within the body of the lubricating device. However, it may also be provided separate from the body of the lubricating device for remote implantation within the patient's body.

Such implantable energy source preferably comprises energy storage means, such as a long-life battery or, more preferably, an accumulator. The accumulator has the advantage of being rechargeable. Preferably, the accumulator comprises a rechargeable battery and/or a capacitor.

Again, coupling elements for conductive or wireless energy transfer from a primary energy source outside the device to the accumulator may be provided for charging the accumulator from outside the patient's body when the device is implanted in the patient's body. Similarly, the accumulator may comprise coupling elements for conductive and/or wireless energy supply to the at least one motor of the infusion device.

While the at least one motor may be provided with actuating means for manual activation of the motor, it is preferred to also provide a control unit for controlling the at least one motor. The control unit may also be used to control the pump, drive mechanism and/or any other energy consuming part of the implanted lubricating device and, where the device includes an internal or external energy source, may even be used to control such energy source. The control unit may be adjusted to the patient's individual needs, such that the appropriate amount of medicine will be administered at appropriate time intervals. Automatic administration will substantially relieve the patient.

Preferably, the control unit has a data transfer port for data transfer between an external data processing device outside the patient's body and the control unit implanted in the patient's body, regardless of whether the control unit is contained in the body of the lubrication device or whether it is implanted within the patient's body remote from the body of the lubricating device. Said data transfer port allows for supervising the control unit to adapt the infusion device to changing needs of the patient. Preferably, the data transfer port is a wireless transfer port for the data transfer, so as to provide easy data exchange between the control unit and the data processing device, e.g. during a visit at the doctor's. Most preferably, the control unit is programmable to further increase its adaptation flexibility.

The control unit—with or without the data transfer port—may also be provided extracorporeally, e.g. mounted on the patient's skin. An external control unit has the advantage of being easily accessible in case of any failure. It is preferably adapted for wireless remote control of the at least one motor implanted with the infusion device.

A control signal transmission device may be provided for wireless transmission of an extracorporeal control signal to an implanted motor. Similarly, a data transmission interface for wirelessly transmitting data from outside the patient's body to a control unit implanted inside the patient's body may be provided. Again, the wireless control signal and/or data transmission may comprise one of the aforementioned wave signals, being digital or analog or a combination thereof. More preferably, the control signal may be transmitted in the same manner as the energy is transmitted to the motor. For instance, the control signal may be transmitted by modulation of the energy signal, the energy signal thereby serving as a carrier wave signal for the digital or analog control signal. More particularly, the control signal may be a frequency, phase and/or amplitude modulated signal.

Apart from or as a part of the control unit, feedback may be provided on parameters relevant for the treatment of the patient. Such parameters may be either physical parameters of the patient and/or process parameters of the device. For that purpose, at least one feedback sensor is provided for detecting such parameters. For instance, the feedback sensor may detect the level of lubricating fluid within the joint or other parameters relating to the condition of the joint and its lubrication. The feedback sensors may be connected to the control unit and the control unit may comprise a control program for controlling delivery of lubricating fluid to the joint in response to one or more signals of the feedback sensors. In addition or alternatively, feedback data may be transferred from the control unit to the external data processing device. Such feedback data may be useful for the doctor's diagnosis.

Preferably, the fluid connection device consists of two fluid connection portions each being connected to the reservoir and having an infusion member at its open end to be inserted into the joint space. The two fluid connection portions may be arranged within the patient's body such that, post-operatively, they form a circular flow path for the lubricating fluid via the joint, i.e. from the pump and/or reservoir to the joint (via a first fluid connection portion) and back to the pump and/or reservoir (via a second fluid connection portion). Under the pressure created by a pump or a flexible outer wall of a reservoir the lubricating fluid may circulate intermittently or continuously through the circular flow path, the second fluid connection portion picking up the lubricating fluid in the joint space that has been inserted thereinto via the first fluid connection portion.

Since due to the circular flow path the lubricating fluid is at least partly re-used after passing the joint, the fluid is soiled in the course of time by impurities or other foreign particles which may reduce the quality and desired effects of the lubricating fluid. The circular fluid connection device of the implantable lubrication device, therefore, may also comprise a filtering device having a filter connected into the circular flow path to remove impure particles from the soiled circulating lubricating fluid. Preferably, the filtering device is adapted to regularly clean the filter and to remove the particles filtered out of the lubricating fluid. These removed impurities or foreign particles may then be deposited into a sealed deposition space or may be given back to the patient's body, e.g. to the surrounding tissue or into a blood vessel or the like.

The lubricating device may be implanted in the patient's body at various locations, preferably as near as possible to the damaged joint to be lubricated. For instance, implantation of the lubrication device—or a part thereof—in the thigh for lubricating the femur ball or knee joint is possible. When the lubricating device or, e.g., its reservoir is relatively voluminous, it may be preferable to implant the lubricating device with a completely filled reservoir as it might be difficult to refill the reservoir in the abdomen. However, a subcutaneously positioned refill injection port connected via a tube to the reservoir may be suitable in this case. Alternatively, the lubrication device may also be implanted subcutaneously. Subcutaneous implantation increases the possibilities of wireless energy and/or data transfer to/from the lubricating device, if desired. Also, refilling the reservoir through a refill injection port by means of a replenishing needle penetrating through the patient's skin is substantially facilitated when the lubricating device is implanted subcutaneously. Depending on the individual treatment, it may be advantageous to implant the lubricating device within fat tissue or intramuscularly or adjacent a joint so that the lubricating fluid can be injected into the particular joint.

Apart from the lubrication device with its various components described above, an implanted lubrication system according to the present invention comprises an appropriate lubricating fluid that is adapted to be stored in the reservoir and to be introduced into the joint by the implanted fluid connection. Preferably, the lubricating fluid is resorbable and bio-compatible in order to ensure resorption of and biological and chemical interaction with the synthetic lubricating fluid by the patient's body in the same way as with a physiological lubricating fluid. Preferably, the lubricating fluid is a hyaluronic acid or the like.

In one embodiment the implantable medical device is adapted to lubricate at least one artificial contacting surface carrying weight in a joint, when implanted in said human or mammal body, said artificial contacting surface replacing at least the surface of at least one of a mammal's joint at least two contacting surfaces, said medical device further comprising, at least one outlet adapted to receive lubricating fluid from said a reservoir, and wherein said medical device is adapted to be operable by an artificial operation device to distribute lubricated fluid from said reservoir and transport it to said at least one artificial contacting surface.

The implantable medical device may have said reservoir and the joint spaced apart, comprising a conduit for fluid connection between said reservoir and the joint.

The implantable medical device may have the reservoir adapted to be placed subcutaneously or in a cavity in the body in a region of the patient selected from a group of regions consisting of:
 a. the abdominal region,
 b. the inguinal region,
 c. the pelvic region, and
 d. the thigh region.

The implantable medical device may thus be placed in the abdomen.

The refill injection port may be adapted to be implanted subcutaneously or in connection with bone.

The implantable medical device may be adapted to lubricate one artificial contacting surface and an opposite contacting surface of the hip or knee joint of a human or mammal patient.

The knee joint having a medial and lateral contacting weight carrying surface, wherein said implantable medical device may be adapted to lubricate said artificial contacting surface on the medial side of the knee joint of a human or mammal patient.

The knee joint having a medial and lateral contacting weight carrying surface, wherein said implantable medical device may be adapted to lubricate said artificial contacting surface of the lateral side on the knee joint of a human or mammal patient.

A mammal joint having at least two contacting surfaces. The medical device is adapted to lubricate at least one artificial contacting surface which has replaced at least the surface of at least one of the mammal's joint contacting surfaces in said joint. Furthermore the medical device comprises at least one inlet adapted to receive a lubricating fluid from a reservoir.

Normally at least one channel is at least partly integrated in the artificial contacting surface in connection with the at least one inlet for distributing the lubricating fluid to the surface of the artificial contacting surface. The medical device could be adapted to be operable by an operation device to distribute lubricated fluid from a reservoir. The possibility to inject a lubricating fluid intermittently or when needed reduces the friction in the joint and enables an optimal level of lubrication in the joint.

According to one embodiment of the implantable medical device, it could be adapted to distribute the lubricating fluid to the surface of the artificial contacting surface on two or more portions of the artificial contacting surface for lubricating the artificial contacting surface. The distribution in more than one portion could enable a more even distribution of the lubricating fluid.

According to another embodiment the medical device the reservoir adapted to hold the lubricating fluid could be an implantable reservoir placed in a cavity of the body, subcutaneously or in connection with bone.

The implantable medical device could further comprise an operation device adapted to transport a lubricating fluid from said reservoir to the artificial contacting surface for lubricating the artificial contacting surface.

According to one embodiment a reservoir could be adapted to hold the lubricating fluid and the operation device according to any of the embodiments herein could be adapted to transport the lubricating fluid from the reservoir to the artificial contacting surface for lubricating the artificial contacting surface. The operation device could be powered and could comprise a pump adapted to pump fluid from the reservoir to the artificial contacting surface for lubricating the artificial contacting surface.

The operation device, according to any of the embodiments herein could comprise a reservoir, pre-loaded with pressurized lubrication fluid.

According to another embodiment, the implantable medical device could further comprise an implantable injection port adapted to allow, by injection into the injection port, to pre-load the reservoir with pressurized lubricating fluid.

The implantable medical device could, according to one embodiment, further comprise a valve adapted to close the connection between the reservoir and the artificial contacting surface. The reservoir could be adapted to be placed in a unit separate from the artificial contacting surface and adapted to be connected to the artificial contacting surface with a conduit. The reservoir could comprise a moveable wall portion adapted to move and change the volume of the reservoir, the wall portion could be a powered wall portion which could comprise a motor.

According to another embodiment, the implantable medical device could comprise at least one outlet and at least one further channel at least partly integrated in the artificial contacting surface. The medical device could be adapted to allow circulation of a lubricating fluid; out from the artificial contacting surface through the outlet and in to the artificial contacting surface through the inlet. The circling of the fluid could be performed by means of an operation device adapted to circulate the lubricating fluid. The circling system could comprise a reservoir adapted to add fluid to the circulating lubricating fluid, and/or a filter to clean the circulating lubricating fluid.

The operation device according to any of the embodiments could be adapted to intermittently transport a lubricating fluid to the artificial contacting surface.

The implantable medical device could according to one embodiment comprise a sensor adapted to sense a physical parameter inside the joint, or a pressure or volume of the lubricating fluid, or a functional parameter of the operation device to control the operation device to adjust the flow of lubricating fluid to the artificial contacting surface.

The reservoir according to any of the embodiments could be connected to the artificial contacting surface through a conduit. The inlet could comprise a connection part, for connecting the conduit to any part of the medical device. The conduit, according to any of the embodiments could comprise a plurality of portions, which could be adapted to be connected to each other through an inter-connecting part. A first portion of the conduit could be in connection with the medical device, and the second portion of the conduit could be in connection with the reservoir. The conduit could according to one embodiment be adapted to pass through a bone of the body for long-term keeping a passage way open through the bone, allowing the lubricating fluid to reach the artificial contacting surface. According to another embodiment the conduit is adapted to pass through a joint capsule of the body for long-term keeping a passage way open through the joint capsule, allowing the lubricating fluid to reach the artificial contacting surface and according to yet another embodiment the conduit is adapted to pass through the pelvic bone from the opposite said of the acetabulum and into the hip joint.

The implantable medical device could be adapted to lubricate a hip joint of a patient, in which case the artificial contacting surface of the medical device could be adapted to at least partly replace a contacting surface of the Acetabulum, and/or the Caput femur.

The implantable medical device could according to one embodiment lubricate a second artificial contacting surface. According to one embodiment the first artificial contacting surface comprises a convex shape towards a centre of the hip joint and the second artificial contacting surface comprises a concave shape towards the centre of the hip joint. The first artificial contacting surface is according to this opposite embodiment adapted to be fixated to the pelvic bone of the human patient, and the second artificial contacting surface is adapted to be fixated to the femoral bone of the human patient. The artificial contacting surface could be adapted to be introduced into the hip joint through a hole in the pelvic bone, from the abdominal side of the pelvic bone, an operational method which allows the hip joint capsule to be kept intact.

The reservoir could according to one embodiment be adapted to be placed inside, or at least partly inside of a bone of the patient, the bone could for example be the femoral bone, the pelvic bone or the collum femur of the patient.

According to another embodiment, the reservoir could be adapted to be placed subcutaneously or in a cavity in the body, which could be a cavity in a region selected from a group of regions consisting of: the abdominal region, the inguinal region, the pelvic region, and the thigh region.

The implantable medical device could according to one embodiment comprise an injection port for filling of the reservoir. The injection port could comprise a self sealing membrane, which for example could be a Parylene coated silicone membrane. The injection port could be adapted to be implanted subcutaneously, in connection with bone or in a cavity of the body.

The reservoir could be adapted to place the lubrication fluid under pressure. For achieving the pressure the reservoir could be adapted to be spring loaded, comprise a chamber adapted to hold a compressed gas or comprise an elastic wall adapted to create the pressure. According to one embodiment the reservoir comprises a Parylene coated silicone elastic wall.

According to another embodiment, the implantable medical device is adapted to lubricate a knee joint of a patient. The artificial contacting surface to be lubricated could according to one embodiment be adapted to at least partly replace a contacting surface of the femoral bone, which could be a contacting surface of the Tibia bone and/or the femoral bone.

According to one embodiment the medical device is adapted to lubricate at least one of the medial or lateral part of the contacting surface of tibia of the knee joint and according to another embodiment the implantable medical device is adapted to lubricate at least one of the medial or lateral part of the contacting surface of the femoral bone of the knee joint. In yet another embodiment the medical device is adapted to lubricate both the contacting surface of the femoral bone of the knee joint and the contacting surface of the tibia bone of the knee joint.

According to one embodiment the reservoir according to any of the embodiments is adapted to be refilled from outside of the human body, the refilling could be performed through an implantable injection port.

According to one embodiment, the reservoir is adapted to hold a pressure, which is possible to increase through injection of a lubricating fluid through the injection port.

The implantable medical device according to any of the embodiments could be adapted to be a part of a system, which further could comprise at least one switch implantable in the patient for manually and non-invasively controlling the implantable medical device. The energized system enables an operation device to operate the lubrication performed by the medical device.

The system could according to one embodiment further comprise a hydraulic device having an implantable hydraulic reservoir, which could be hydraulically connected to the implantable medical device. The implantable medical device could be adapted to be non-invasively regulated by manually pressing the hydraulic reservoir.

According to another embodiment, the system could further comprise a wireless remote control for non-invasively controlling the implantable medical device. The wireless remote control could comprise at least one external signal transmitter and/or receiver, further comprising an internal signal receiver and/or transmitter implantable in the patient for receiving signals transmitted by the external signal transmitter or transmitting signals to the external signal receiver. The wireless remote control could further be adapted to transmit at least one wireless control signal for controlling the implantable medical device. The wireless control signal could comprise a frequency, amplitude, or phase modulated signal or a combination thereof. The wireless remote control could further be adapted to transmit an electromagnetic carrier wave signal for carrying the control signal.

According to another embodiment the system could comprise a wireless energy-transmission device for non-invasively energizing the implantable energy consuming components of the implantable medical device with wireless energy. The wireless energy could comprise a wave signal, selected from the following: a sound wave signal, an ultrasound wave signal, an electromagnetic wave signal, an infrared light signal, a visible light signal, an ultra violet light signal, a laser light signal, a micro wave signal, a radio wave signal, an x-ray radiation signal, gamma radiation signal, an electric field, a magnetic field, a combined electric and magnetic field.

A control signal in the system could comprise an electric field, a magnetic field, a combined electric and magnetic field. The signal could comprise an analogue signal, a digital signal, or a combination of an analogue and digital signal. For powering the energy consuming components of the implantable medical device, the implantable system could comprise an implantable internal energy source. According to another embodiment the system comprises an external energy source for transferring energy in a wireless mode, wherein the internal energy source is chargeable by the energy transferred in the wireless mode.

According to a further embodiment the system could further comprise a sensor or a measuring device sensing or measuring a functional parameter correlated to the transfer of energy for charging the internal energy source, and a feedback device for sending feedback information from inside the patient's body to the outside thereof, the feedback information could be related to the functional parameter sensed by the sensor or measured by the measuring device.

According to yet another embodiment, the system could further comprise a feedback device for sending feedback information from inside the patient's body to the outside thereof, the feedback information being related to at least one of a physical parameter of the patient and a functional parameter related to the implantable medical device.

The system could according to one embodiment further comprise a sensor and/or a measuring device and an implantable internal control unit for controlling the implantable medical device in response to information being related to at least one of a physical parameter of the patient sensed by the sensor or measured by the measuring device and a functional parameter related to the implantable medical device sensed by the sensor or measured by the measuring device. The physical parameter could according to one embodiment be a pressure or a motility movement.

The system could according to one embodiment comprise an external data communicator and an implantable internal data communicator communicating with the external data communicator, the internal communicator feeds data related to the implantable medical device or the patient to the external data communicator and/or the external data communicator feeds data to the internal data communicator.

The system according to any of the embodiments herein, could further comprise a motor or a pump for operating the implantable medical device, or a hydraulic operation device for operating the implantable medical device. The operation device could comprise a servo designed to decrease the force needed for the operation device to operate the implantable medical device instead the operation device acting a longer way, increasing the time for a determined action.

According to one embodiment the system could further comprise an operation device for operating the implantable medical device. The wireless energy could be used in its wireless state to directly power the operation device to create kinetic energy for the operation of the implantable medical device, as the wireless energy is being transmitted by the energy-transmission device. The system could also comprise an energy-transforming device for transforming the wireless energy transmitted by the energy-transmission device from a first form into a second form energy.

The energy-transforming device could be adapted to directly power implantable energy consuming components of the implantable medical device with the second form energy, as the energy-transforming device transforms the first form energy transmitted by the energy-transmission device into the second form energy. The second form energy could comprise at least one of a direct current, pulsating direct current and an alternating current. The energy of the first or second form could comprise at least one of magnetic energy, kinetic energy, sound energy, chemical energy, radiant energy, electromagnetic energy, photo energy, nuclear energy thermal energy, non-magnetic energy, non-kinetic energy, non-chemical energy, non-sonic energy, non-nuclear energy and non-thermal energy.

For protecting the system or the parts of the system, the system could further comprise an implantable electrical component including at least one voltage level guard and/or at least one constant current guard. A control device could be arranged to control the transmission of wireless energy from the energy-transmission device, and an implantable internal energy receiver for receiving the transmitted wireless energy, the internal energy receiver could be connected to implantable energy consuming components of the implantable medical device for directly or indirectly supplying received energy thereto, the system could further comprise a determination device adapted to determine an energy balance between the energy received by the internal energy receiver and the energy used for the implantable energy consuming components of the implantable medical device, the control device could be adapted to control the transmission of wireless energy from the external energy-transmission device, based on the energy balance determined by the determination device.

The determination device could be adapted to detect a change in the energy balance, the control device could be adapted to control the transmission of wireless energy based on the detected energy balance change. The determination device could in turn be adapted to detect a difference between energy received by the internal energy receiver and energy used for the implantable energy consuming components of the implantable medical device, and the control device could be adapted to control the transmission of wireless energy based on the detected energy difference.

The energy-transmission device could comprise a coil placed externally to the human body, which in turn could further comprise an implantable energy receiver to be placed internally in the human body and an electric circuit connected to power the external coil with electrical pulses to transmit the wireless energy, the electrical pulses having leading and trailing edges, the electric circuit adapted to vary first time intervals between successive leading and trailing edges and/or second time intervals between successive trailing and leading edges of the electrical pulses to vary the power of the transmitted wireless energy, the energy receiver receiving the transmitted wireless energy having a varied power. The electric circuit could be adapted to deliver the electrical pulses to remain unchanged except varying the first and/or second time intervals.

The system could according to one embodiment have an electric circuit having a time constant which is adapted to vary the first and second time intervals only in the range of the first time constant, so that when the lengths of the first and/or second time intervals are varied, the transmitted power over the coil is varied.

The implantable internal energy receiver for receiving wireless energy could comprise an internal first coil and a first electronic circuit connected to the first coil, and an external energy transmitter for transmitting wireless energy, the energy transmitter having an external second coil and a second electronic circuit connected to the second coil, wherein the external second coil of the energy transmitter transmits wireless energy which is received by the first coil of the energy receiver, the system further comprising a power switch for switching the connection of the internal first coil to the first electronic circuit on and off, such that feedback information related to the charging of the first coil is received by the external energy transmitter in the form of an impedance variation in the load of the external second coil, when the power switch switches the connection of the internal first coil to the first electronic circuit on and off.

The system could also comprise an implantable internal energy receiver for receiving wireless energy, the energy receiver having an internal first coil and a first electronic circuit connected to the first coil, and an external energy transmitter for transmitting wireless energy, the energy transmitter having an external second coil and a second electronic circuit connected to the second coil, wherein the external second coil of the energy transmitter transmits wireless energy which is received by the first coil of the energy receiver, the system further comprising a feedback device for communicating out the amount of energy received in the first coil as a feedback information, and wherein the second electronic circuit includes a determination device for receiving the feedback information and for comparing the amount of transferred energy by the second coil with the feedback information related to the amount of energy received in the first coil to obtain the coupling factors between the first and second coils.

In the embodiments in which the system comprises an external second coil, the external second coil could be adapted to be moved in relation to the internal first coil to establish the optimal placement of the second coil, in which the coupling factor is maximized. The external second coil could also be adapted to calibrate the amount of transferred energy to achieve the feedback information in the determination device, before the coupling factor is maximized.

According to a second aspect, a method of implanting the medical device according to any of the embodiments herein is further provided. The method comprises the steps of: creating an opening reaching from outside of the human body into a joint, providing the artificial contacting surface to the joint, fixating the artificial contacting surface to the joint, implanting the reservoir in the human body, and lubricating the artificial contacting surface with use of a lubricating fluid contained in the reservoir.

The step of lubricating the joint contacting surface or the artificial contacting surface with use of a lubricating fluid contained in the reservoir could comprise implanting an operation device adapted to transport the fluid from the reservoir to the artificial contacting surface. According to another embodiment the step of lubricating the artificial contacting surface with use of a lubricating fluid contained in the reservoir comprises providing an energy source for powering the operation device.

According to yet another embodiment the step of lubricating the joint contacting surface or artificial contacting surface with use of a lubricating fluid contained in the reservoir could comprise powering the operation device using the energy source.

The step of implanting a reservoir in the human body could, according to one embodiment, comprise the step of implanting an operation device being integrated in the reservoir, allowing the step of lubricating the artificial contacting surface with use of a lubricating fluid contained in the reservoir, using the operation device transporting the fluid from the reservoir to the artificial contacting surface.

Implanting the reservoir, according to any of the embodiments could comprise the step of implanting the reservoir at least partially inside of a bone of the patient, which could be the femoral bone of the patient, the tibia bone of the patient and/or the pelvic bone of the patient.

The step of providing the artificial contacting surface could comprise the step of providing the artificial contacting surface from the abdominal side of the pelvic bone.

The step of implanting the reservoir in the human body could comprise the step of implanting the reservoir subcutaneously. Placing the reservoir subcutaneously allows simple access to the reservoir and eliminates the need for a long conduit between an injection port and the reservoir.

The step of implanting the reservoir subcutaneously could comprise the step of implanting the reservoir in at least one of the regions of the patient selected from a group of regions consisting of: the abdominal region, the inguinal region, the pelvic region, the thigh region, and the calf region.

A further step of implanting an injection port for filling of the reservoir could be performed. The implantation of an injection port could comprise the step of implanting the injection port in connection with bone.

According to one embodiment, the medical device comprises an artificial contacting surface adapted to carry weight in a joint of a patient, the artificial contacting surface could comprise at least one channel for transporting a lubricating fluid, the method comprises the steps of: implanting the medical device in a joint of the human patient, implanting a conduit adapted to be connected to the medical device, implanting an operation device for transporting a lubricating fluid inside the conduit, implanting a reservoir adapted to hold a lubricating fluid, and at least postoperatively transporting, by the operation device, the lubricating fluid from the reservoir to the artificial contacting surface in the conduit and further through the channel in the artificial contacting surface, thereby applying the lubricating fluid to the artificial contacting surface.

Generally, the lubrication device may be implanted during a conventional surgery or by endoscopic or laparoscopic methods. Further, one has to differentiate between methods for implanting a lubrication device having an infusion needle for intermittent introduction of lubricating fluid and methods for implanting a lubrication device having an infusion tube for continuous introduction of lubricating fluid.

In a method of treating a human or mammal joint, e.g. a human hip or knee joint osteoarthritis, by providing a lubricating fluid to the joint by means of the implantable lubrication device, a proper location including an area of the joint is dissected free in the patient's body by surgery, which may especially include cutting the patient's skin and dissecting a suitable place for a reservoir to store the lubricating fluid. Then, the lubrication device is placed at the dissected-free proper location in such a way that the fluid connection may post-operatively introduce lubricating fluid into the joint. For this purpose, a hole is created in the joint capsule at the dissected-free area of the joint and an infusion tube is introduced into the hole such that an open end of the infusion tube is placed in continuous communication with the joint in order to post-operatively inject lubricating fluid stored in the reservoir into the joint on a continuous basis. That is, the infusion tube is inserted in the hole such that, firstly, the opening end of the infusion tube is kept in permanent communication with the joint to be lubricated and, secondly, the infusion tube is in contact with the fluid connection device and thus with the reservoir. After placement of the lubrication device, the patient's body is closed such that the lubrication device is entirely implanted in the patient's body. This process may preferably be performed in layers and by means of sutures or staples or adhesives or the like. Finally, after the implantation process, the lubricating fluid is post-operatively introduced into the reservoir such that by operation of the implanted lubrication device the joint is adequately lubricated.

Alternatively, if the fluid connection comprises an intermittently operating infusion needle as the infusion member, the placement of the lubrication device at the dissected-free proper location and the area of the joint is realized by placing the infusion needle in such a close relation to the dissected area of the joint that a drive mechanism of the infusion needle may introduce and retract the infusion needle intermittently into/out of the joint such that lubricating fluid stored in the reservoir is intermittently injected into the joint. That is, the infusion needle is placed in close relation to the dissected-free area of the joint such that it may by intermittently introduced into the joint for lubricating the joint and retracted thereafter by an appropriate drive mechanism connected to a drive mechanism or the like.

Another method of treating a human or mammal patient by means of the implantable lubrication device utilizes endoscopic or laparoscopic techniques for creating an area of the joint via which lubricating fluid may be injected into the joint by the infusion member. This area of the joint is provided by, first, expanding a cavity in close relation to the joint by inserting a needle-like or a tube-like instrument in the patient's body and introducing a gas through the needle/tube-like instrument to fill gas into the tissue and thereby expand the cavity near the joint. Thereafter, at least two laparoscopic/endoscopic trocars are placed in the cavity and a camera and at least one dissecting tool are inserted through the laparoscopic trocars. The area of the joint is then dissected with the inserted dissecting tool. Also, a proper location for the remaining components of the lubrication device is dissected free, e.g. the reservoir, a pump or motor, or the like. The lubrication device is then placed at the proper location, whereas the fluid connection with the infusion member is arranged at the laparoscopically dissected area of the joint such that lubricating fluid is introduced into the joint. After placement of the lubrication device, the patient's body is closed with the effect that the lubrication device is entirely implanted in the patient's body. Thereafter, the lubricating fluid can be post-operatively introduced into the reservoir such that said joint is adequately lubricated through the fluid connection device and the infusion member.

Using the laparoscopic approach, again, a lubrication device having either an infusion tube or an infusion needle may be implanted. In the former case, the reservoir is placed at the proper location and a hole is created in the joint capsule at the laparoscopically dissected area of the joint and the infusion tube is inserted into the hole such that that an open end of the tube is placed in continuous communication with the joint and the stored lubricating fluid may continuously be injected into the joint. In the latter case, after placing the reservoir at the proper location, an infusion needle and a drive mechanism are placed in close relation to the laparoscopically dissected area of the joint such that the drive mechanism may intermittently introduce (and retract)

the infusion needle into (and out of) the joint in order to allow the stored lubricating fluid to be intermittently injected into the joint.

Closing the patient's body, or particularly the skin, may for instance include suturing, taping and other suitable techniques. The lubrication device may be placed subcutaneously in the patient's body or within fat tissue or intramuscularly. If appropriate, the lubrication device may also be placed within or adjacent the patient's gastro-intestinal or urinary tract. When it is placed adjacent the tract, it may be secured to the gastro-intestinal or urinary tract by means of a holder connected to the lubrication device. As a further alternative, the lubrication device may be placed in the patient's thorax or in the patient's abdomen. For instance, a reservoir may be placed in the abdomen or thorax cavity. Alternatively, the lubrication device or part thereof, such as a reservoir, may be implanted by open surgery, in which case the thorax or abdominal wall is opened for placing the lubrication device at the proper location within the patient's thorax or abdomen and, afterwards, the skin and other layers of tissue are closed, such as by suturing, being preferably sutured in layers. Replenishing of the reservoir preferably comprises the step of injecting a volume of lubrication liquid through the injection port connected to and/or integrated in the periphery of the reservoir, e.g. a reservoir.

Functional hip movements are to be understood as movements of the hip that at least partly correspond to the natural movements of the hip. On some occasions the natural movements of the hip joint might be somewhat limited or altered after hip joint surgery, which makes the functional hip movements of a hip joint with artificial surfaces somewhat different than the functional hip movements of a natural hip joint.

The functional position of an implantable medical hip device or prosthesis is the position in which the hip joint can perform functional hip movements. The final position is to be understood as a functional position in which the medical device needs no further position change.

Functional knee movements are to be understood as movements of the knee that at least partly correspond to the natural movements of the knee. On some occasions the natural movements of the knee joint might be somewhat limited or altered after knee joint surgery, which makes the functional knee movements of a knee joint with artificial surfaces somewhat different than the functional knee movements of a natural knee joint.

The functional position of an implantable medical knee device or prosthesis is the position in which the knee joint can perform functional knee movements.

Functional knee joint is a knee joint that can perform functional knee movements either with or without an implanted medical device or prosthesis.

Full functional size is to be understood as the size of the medical knee device when said medical device is implanted in the knee joint.

Arthroscopy is to be understood as key hole surgery performed in a joint, since the arthroscopic procedure could be performed in the abdomen of the patient some of the steps of this arthroscopic procedure is more laparoscopic, however for the purpose of this invention the two terms arthroscopy and laparoscopy is used synonymously and for the purpose of this invention the main purpose of these methods are is that they are minimally invasive.

The medical device according to any of the embodiments could comprise at least one material selected from a group consisting of: polytetrafluoroethylene (PTFE), perfluoroalkoxy (PFA) and fluorinated ethylene propylene (FEP). It is furthermore conceivable that the material comprises a metal alloy, such as cobalt-chromium-molybdenum or titanium or stainless steel, or polyethylene, such as cross-linked polyethylene or gas sterilized polyethylene. The use of ceramic material is also conceivable, in the artificial contacting surfaces or the entire medical device such as zirconium or zirconium dioxide ceramics or alumina ceramics. The part of the medical device in contact with human bone for fixation of the medical device to human bone could comprise a poorhouse structure which could be a porous micro or nano-structure adapted to promote the growth-in of human bone in the medical device for fixating the medical device. The porous structure could be achieved by applying a hydroxy-apatite (HA) coating, or a rough open-pored titanium coating, which could be produced by air plasma spraying, a combination comprising a rough open-pored titanium coating and a HA top layer is also conceivable. The contacting parts could be made of a self lubricated material such as a waxy polymer, such as PTFE, PFA, FEP, PE or UHMWPE, or a powder metallurgy material which could be infused with a lubricant, which preferably is a biocompatible lubricant such as a Hyaluronic acid derivate. It is also conceivable that the material of contacting parts or surfaces of the medical device herein is adapted to be constantly or intermittently lubricated. According to some embodiments the parts or portions of the medical device could comprise a combination of metal materials and/or carbon fibers and/or boron, a combination of metal and plastic materials, a combination of metal and carbon based material, a combination of carbon and plastic based material, a combination of flexible and stiff materials, a combination of elastic and less elastic materials, Corian or acrylic polymers.

Please note that any embodiment or part of embodiment as well as any method or part of method could be combined in any way. All examples herein should be seen as part of the general description and therefore possible to combine in any way in general terms. Please note that the description in general should be seen as describing both of an apparatus and a method.

The various aforementioned features of the embodiments may be combined in any way if such combination is not clearly contradictory. Embodiments will now be described in more detail in reference to the accompanying drawings. Again, individual features of the various embodiments may be combined or exchanged unless such combination or exchange is clearly contradictory to the overall function of the device.

BRIEF DESCRIPTION OF THE DRAWINGS

FIG. 2A shows an implanted lubrication device with an infusion needle and a drive mechanism.

FIG. 2B shows the lubrication device of FIG. 2A diagrammatically with some modifications.

FIG. 10 shows the hip joint is section when a medical device connected to an implantable lubrication system is being provided.

FIGS. 11a-c show a surgical instrument for use in a method of providing a medical device according to any of the embodiments herein.

FIG. 12 shows the hip joint in section when a medical device has been implanted and connected to an implantable reservoir.

FIG. 20 shows a frontal view of a knee joint of a human patient, when a medical device has been provided.

FIG. 21 shows an implantable lubricating system.

FIG. 34 illustrates a system for treating a disease, wherein the system includes an apparatus of the invention implanted in a patient.

FIGS. 35-49 schematically show various embodiments of the system for wirelessly powering the apparatus shown in FIG. 34.

FIG. 50 is a schematic block diagram illustrating an arrangement for supplying an accurate amount of energy used for the operation of the apparatus shown in FIG. 34.

DETAILED DESCRIPTION

Figure 1:
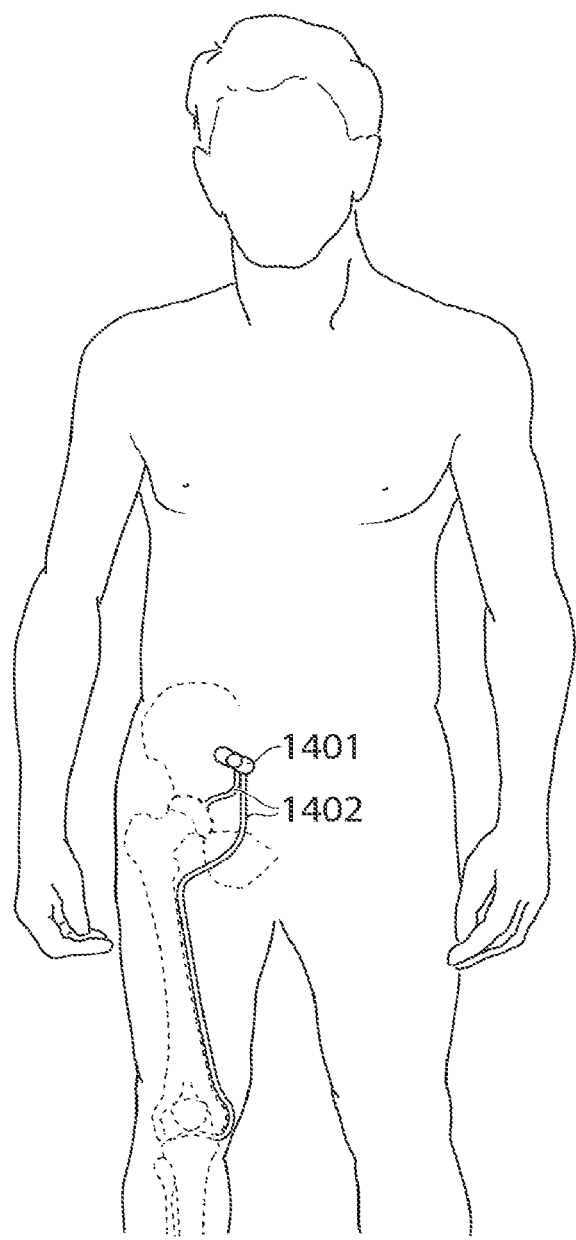
FIG. 1 shows a patient's body with an implanted lubrication device for lubrication of a hip joint and/or a knee joint.

In the following a detailed description of preferred embodiments will be given. In the drawing figures, like reference numerals designate identical or corresponding elements throughout the several figures. It will be appreciated that these figures are for illustration only and are not in any way restricting the scope. Thus, any references to direction, such as "up" or "down", are only referring to the directions shown in the figures. Also, any dimensions etc. shown in the figures are for illustration purposes.

Please note that any embodiment or part of embodiment as well as any method or part of method could be combined in any way. All examples herein should be seen as part of the general description and therefore possible to combine in any way in general terms.

FIG. 1 shows a patient's body with an implanted lubrication device consisting of a main body 1401 and two fluid connection tubes 1402 that transport a lubricating fluid stored in a reservoir into the joints to be lubricated, here a hip joint and a knee joint. For this reason, the main body 1401 comprises a reservoir for storing the lubricating fluid and may also comprise further components, such as a pump, a motor, a control unit or the like. The lubrication device, i.e. all its components, is fully implantable into the patient's body such that the joint can be appropriately lubricated post-operatively independently of any extracorporeal components or injections, which significantly reduces the infection risk for the patient. Depending on the type of joint and on the severity of the damage to the joint, a joint may be lubricated intermittently/periodically, continuously, or as required, e.g. depending on a lubricating fluid level within the joint. Generally, the main body 1401 of the lubrication device may be implanted subcutaneously so that it is easily accessible, e.g. for refilling the reservoir or setting up functionalities or modes of operation via a wireless control unit or the like.

Figure 1A:
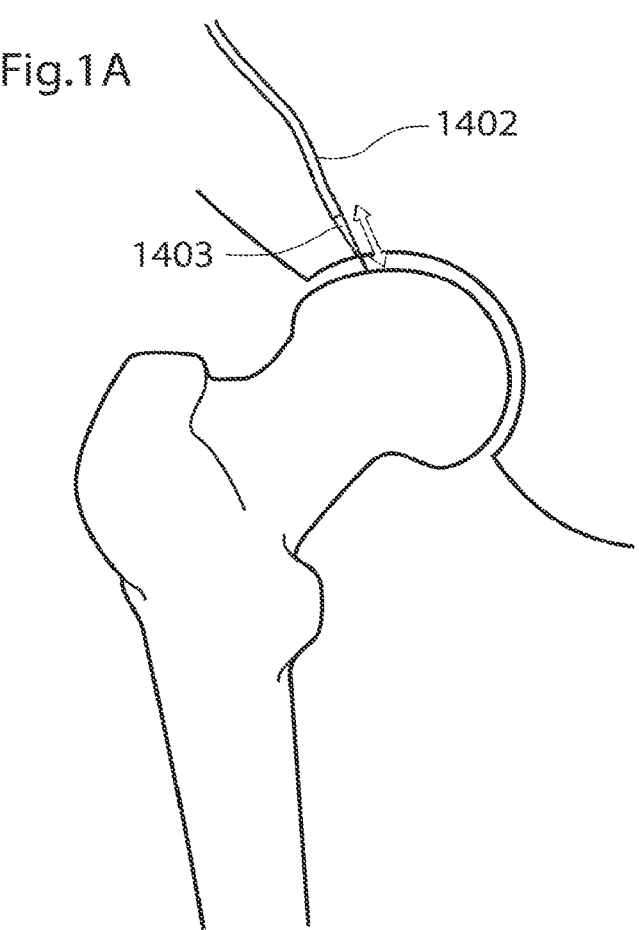
FIGS. 1A and 1B illustrate the hip joint and the knee joint of FIG. 1, respectively, having an infusion member of the implanted lubrication device inserted therein.
Figure 1B:
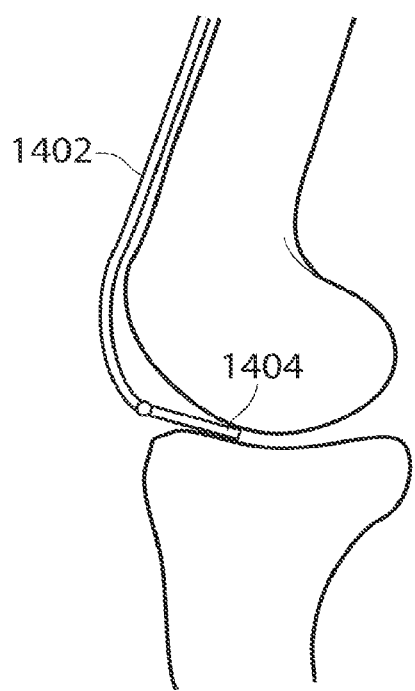

In FIGS. 1A and 1B the two lubricated joints shown in FIG. 1, the hip joint and the knee joint, are illustrated respectively in greater detail. In FIGS. 1A and 1B it can be seen that the fluid connection tube 1402 has at its end an infusion member being inserted into the joint space which finally brings the lubricating fluid into the joint. FIG. 1A shows an infusion needle 1403 which is injected through the joint capsule into the joint space of the hip joint. The infusion needle 1403 may, in connection with a drive mechanism (not shown), be advanced into the joint space and retracted from it in order to intermittently lubricate the joint. Alternatively, in FIG. 1B, the infusion member is an infusion tube 1404 that is permanently placed in the joint space such that a continuous flow of lubricating fluid reaches the joint. The material of the infusion tube 1404 may be a soft material not or only minimally disturbing the joint in its regular operation. A drive mechanism is not required for the infusion tube 1404 of FIG. 1B.

Generally, there are two basic methods for implanting the lubrication device, a conventional method in which an area of the joint is dissected free and the infusion needle 1403 or infusion tube 1404 is arranged at the free-dissected area, and a laparoscopic method in which a cavity at the joint is expanded laparoscopically and the infusion needle 1403 or infusion tube 1404 is placed in the cavity through laparoscopic trocars. If the fluid connection tube 1402 ends in an infusion needle 1403, as shown in FIG. 1A, the infusion needle 1403 is placed in close relation to the joint capsule or into a hole in the capsule in such a way that a drive mechanism of the needle may introduce and retract the infusion needle 1403 intermittently into and out of the joint space such that lubricating fluid stored in the reservoir is intermittently injected. If, alternatively, the fluid connection tube 1402 ends in an infusion tube 1404, as shown in FIG. 1B, a permanent hole is created in the joint capsule in which the tube is continuously placed such that the lubricating fluid may be continuously injected into the joint.

Figure 1C:
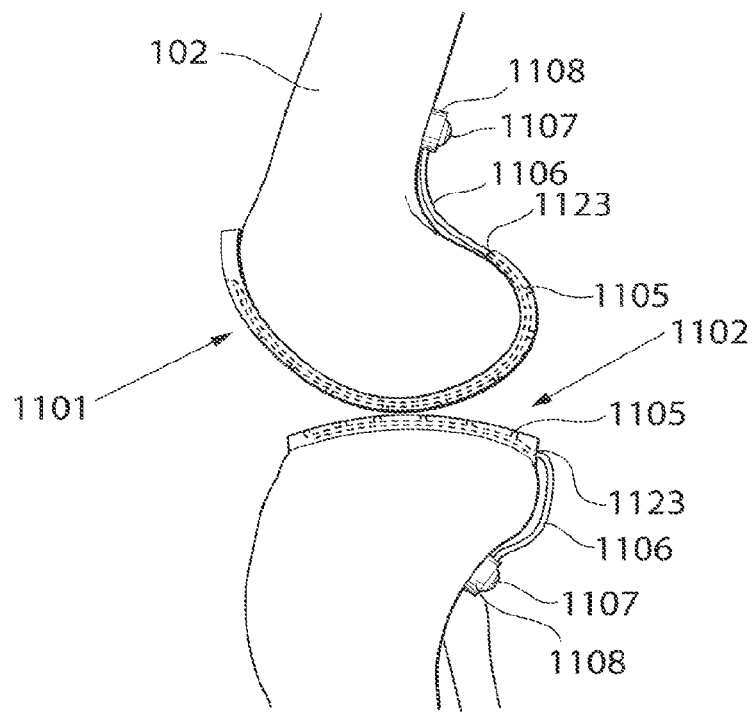
FIG. 1C shows a lateral view of a knee joint when a medical device has been provided.

FIG. 1C shows a medical device according to an embodiment in which the medical device comprises a first artificial contacting surface 1101 adapted to replace the distal surface of the femoral bone 102, being part of the knee joint. The first artificial contacting surface 1101 could be adapted to replace the surface of the lateral condyle, the medial condyle or both the lateral and medial condyles. The medical device of FIG. 1C further comprises a second artificial contacting surface 1102 being adapted to replace the contacting surface of the tibia bone being the other contacting surface of the knee joint. The implantable medical device comprises an inlet 1104 adapted to receive a lubricating fluid from a reservoir 1108, which according to this embodiment is placed on the rear side of the tibia bone 102 and the rear side of the femoral bone 102, respectively. The reservoir 1108 is according to this embodiment adapted to be refilled by means of an injection port 1107 being placed in fluid contact with the reservoir 1108. The reservoir 1108 supplies the inlet 1104; 1123 with a lubricating fluid through a conduit 1106 which supplies a fluid connection between the medical device and the reservoir 1108. The reservoir is according to this embodiment adapted to be placed under pressure through said injection port 1108 comprising chamber for pressurized gas which is further compressed when the reservoir 1108 is being filled through the injection port 1107. The inlet 1104; 1123 transports the lubricating fluid to a channel 1105 which is at least partly integrated in said artificial contacting surfaces 1101,1102. According to the embodiment of FIG. 1 the channel 1105 is fully integrated in the medical device. The channel 1105 distributes the lubricating fluid over the artificial contacting surfaces 1101, 1102 and thereby lubricates the artificial contacting surfaces 1101,1102 and improves the function thereof by reducing the friction. The implantable medical device could just as well be adapted to be implanted in the knee joint of another mammal, such as a horse.

Figure 1D:
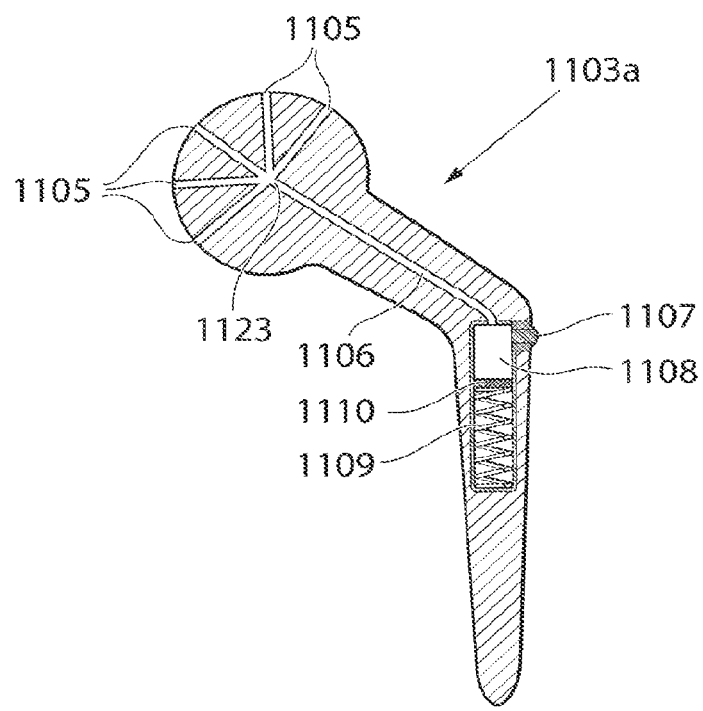
FIG. 1D shows the medical device according to one embodiment, in section.

FIG. 1D shows the implantable medical device according to an embodiment where the medical device is adapted to replace parts of the hip joint. The medical device comprises a plurality of channels 1105 adapted to lubricate the artificial contacting surface of the hip joint by a lubricating fluid being injected to the channel through a conduit 1106 placed centrally in the implantable medical device. The conduit 1106 places the plurality of channels 1105 in fluid connection with a reservoir 1108 which is located in the stem part, adapted for fixation in the femoral bone of a human patient, of said medical device. The conduit 1106 transports lubricating fluid to the inlet 1123 for further distribution to the channels 1105. The reservoir 1108 according to the embodiment of FIG. 1D is spring loaded by a spring 1109 which pushes a movable wall portion in the shape of a piston 1110 for placing said lubricating fluid under pressure. The reservoir 1108 is adapted to be refilled through the injection port 1107, which is placed on the lateral side of the medical device. The injecting of lubricating fluid through the injection port 1107 compresses the spring 1109 which thereby places the lubricating fluid under pressure, which pressure presses the lubricating fluid through the conduit 1106 and to the channels 1105 for lubricating the hip joint of a human patient. The spring loaded reservoir 1108 could be replaced by other types of reservoirs adapted to place a pressure on the lubricating fluid, such as a reservoir 1108 comprising a chamber filled with a pressurized gas which is further pressurized by the injecting of a lubricating fluid through an injection port, it is furthermore conceivable that the reservoir 1108 is an elastic reservoir in which case the elastic properties of the elastic reservoir pressurized the lubricating fluid.

Figure 1E:
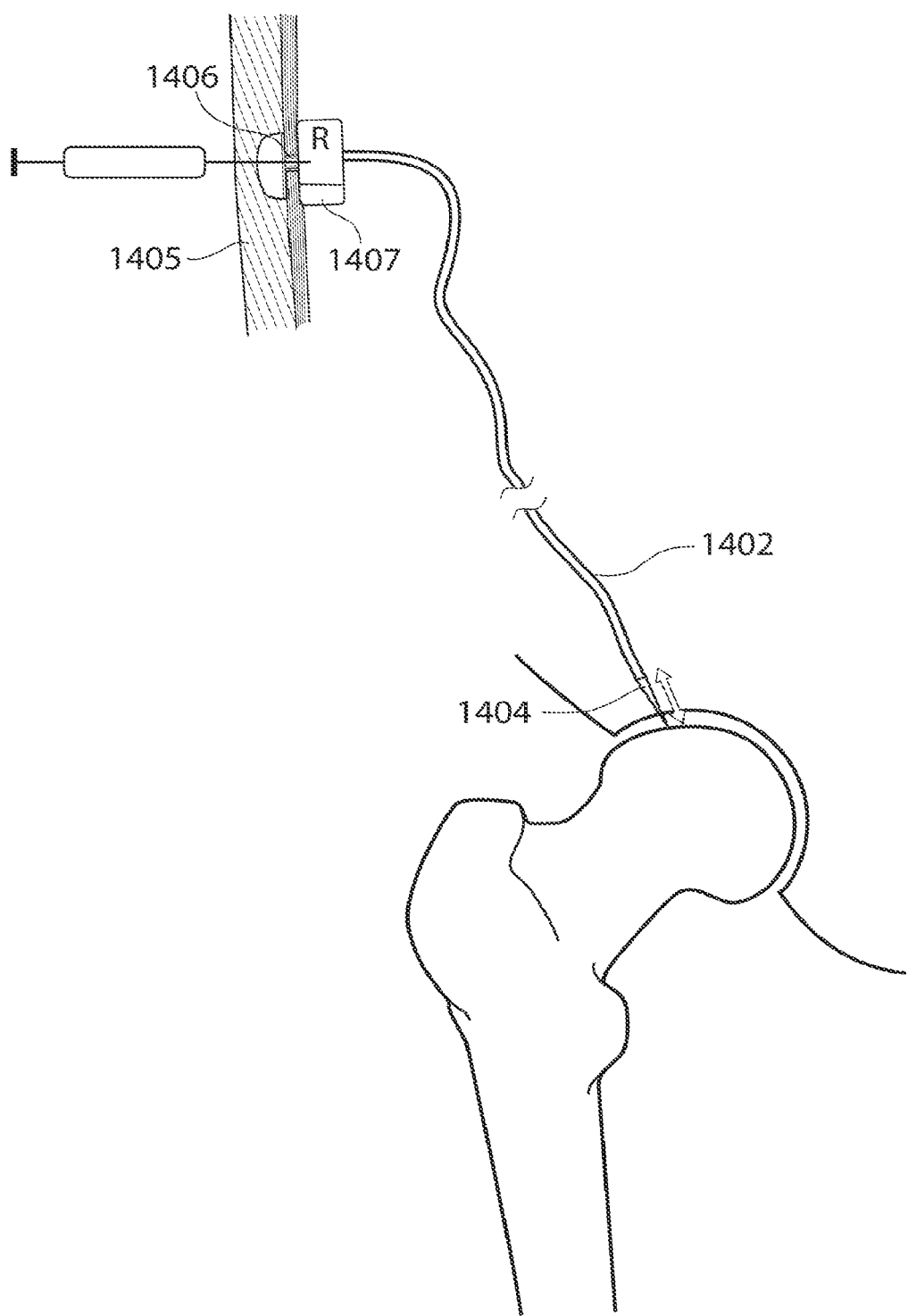
FIG. 1E illustrates the main components of an implanted lubrication device.

FIG. 1E illustrates an implanted lubrication device and its main components. The lubrication device of FIG. 1E comprises a reservoir R for storing the lubricating fluid and a fluid connection tube 1402 that connects the reservoir R with a infusion tube 1404 placed with its open end permanently within a joint space. In order to create an appropriate pressure for forcing the lubricating fluid from the reservoir R through the fluid connection tube 1402 and the injection tube 1404 into the joint, a gas chamber 1407 is arranged within the reservoir R that may produce the required pressure upon expanding its volume. Further, the reservoir is subcutaneously implanted such that a refill injection port 1406 arranged in the outer wall of the reservoir R is accessible through the patient's skin 1405 such that lubricating fluid can be replenished into the reservoir R by a syringe injected through the patient's skin 1405. The refill injection port 1406 may thus be made of an appropriate membrane, e.g. a polymer material, which is self-sealing with respect to the penetration of an injection syringe.

Figure 1F:
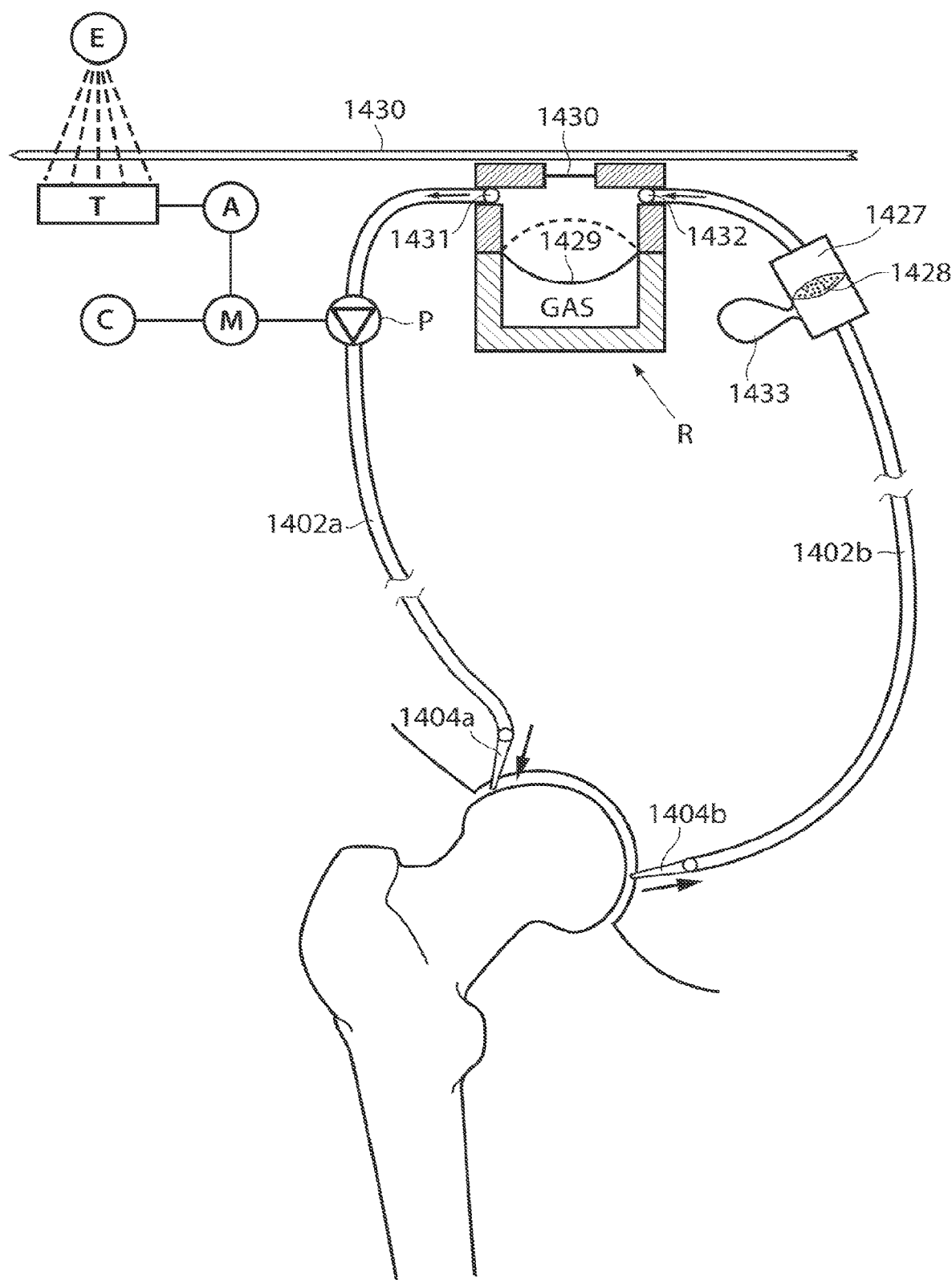
FIG. 1F shows a motor-driven implanted lubrication device establishing a circular flow path.

FIG. 1F shows another embodiment of the lubrication device according to the present invention. A pump P driven by a motor M connects a reservoir R with a circular fluid connection tube 1402 consisting of two tube portions 1402*a*, 1402*b* that form a full circular flow path for the lubricating fluid via the reservoir R and the lubricated joint. Each of the two tube portions 1402*a*, 1402*b* comprises an individual infusion tube 1404*a*, 1404*b* inserted into the joint space, whereas the lubricating fluid stored in the reservoir is introduced into the joint space via the tube portion 1402*a* with the infusion tube 1404*a*, while the used lubricating fluid is led from the joint back to the reservoir via the tube portion 1402*b* with the infusion tube 1404*b* via a filter device 1427 with a filter 1428 placed within the flow path partially defined by tube portion 1402*b*. Under the pressure created by the pump P the lubricating fluid is circulated continuously within the circular flow path formed by the fluid connection tube portions 1402*a*, 1402*b*, such that the lubricating fluid may be at least partly re-used after passing the joint. However, in order to enable re-usage of the lubricating fluid flowing out of the joint and into infusion tube 1404*b*, possible soiling and impurities or other foreign particles which have been added to the lubricating fluid on its way through the joint are removed by the filtering device 1427 in order to secure the quality and desired effects of the lubricating fluid upon re-usage. The filtering device 1427 has a filter 1428 which is placed within the flow path such that the complete lubricating fluid passes through the filter. The filtering device 1427 is adapted to regularly clean the filter 1428 by removing the filtered particles from the filter 1428 and depositing them in a sealed deposition space 1433. Alternatively, the removed particles can also be given back to the patient's body, e.g. into a blood vessel or the like.

Although the embodiment shown in FIG. 1F may comprise a great variety of reservoir types, a particular reservoir type will be described below. The volume of reservoir R shown in FIG. 1F is divided into two sections by means of a membrane 1429. One section is filled with gas, whereas the other section is filled with lubricating fluid. A refill injection port 1430 allows for refilling reservoir R with infusion liquid by means of a replenishing needle through the patient's skin 1405. When reservoir R is in its full state, the gas section is at ambient pressure or over-pressurized. As lubricating fluid is drawn from reservoir R upon each lubrication cycle, the pressure in the gas section will decrease below ambient pressure, i.e. to a negative relative value. Depending upon the particular type of pump P, it may be advantageous to provide an active ball valve 1431 to prevent any back-flow from pump P to reservoir R and another active ball valve 1432 to prevent any back-flow from the reservoir R into the fluid connection conduit 1402*b*.

Motor M is wirelessly controlled by a control unit C implanted in the patient's body as well. However, it is also possible to place the control unit C outside the patient's body and establish a wireless communication between control unit C and motor M or provide galvanic contacts through the patient's skin. Preferably, the control unit C is implanted along with motor M, in which case control unit C is preferably programmable from outside the patient's body, either wirelessly or through galvanic contacts, so as to allow proper configuration of the control unit according to changing demands. Control unit C determines the time period between the infusion cycles as well as the amount of lubricating fluid to be injected into the space upon each infusion cycle. In addition to or instead of control unit C, a pressure sensitive switch for activating motor M may be arranged subcutaneously.

There are various ways of providing motor M with energy. For instance, energy may be supplied from outside the patient's body e.g. for charging an accumulator A, such as a rechargeable battery and/or a capacitor. In the embodiment shown in FIG. 1F, an extracorporeal primary energy source E transmits energy of a first form through the patient's skin 1405 to an energy transforming device T which transforms the energy of the first form into energy of a second form, such as electric energy. The electric energy is used to recharge accumulator A which provides secondary energy to motor M upon demand.

In general, external energy source E may be adapted to create an external field, such as an electromagnetic field, magnetic field or electric field, or create a wave signal, such as an electromagnetic wave or sound wave signal. For instance, energy transforming device T as shown in FIG. 1F may act as a solar cell, but be adapted to the particular type of wave signal of primary energy source E. Energy transforming device T may also be adapted to transform temperature changes into electric energy. Instead of an external primary energy source E, an implantable primary energy source E may be used, such as a regular long-life battery instead of accumulator A. The energy signal can also be used to transmit a control signal of the control unit C by appropriate modulation of the energy signal, regardless of whether the energy is transmitted wirelessly or by wire, the energy signal thereby serving as a carrier wave signal for the digital or analog control signal. More particularly, the control signal may be a frequency, phase and/or amplitude modulated signal.

FIG. 2A shows in further detail an implanted lubrication device comprising an infusion needle 1403 having a tip end 1408. Tip end 1402 is closed at its distal end and has a lateral lubricating fluid delivery exit port 1409. Needle 1403 is arranged for longitudinal displacement within an open-ended fluid connection tube 1402 upon activation by a drive mechanism D.

The fluid connection tube 1402 is attached to an implanted pump P. Pump P is schematically shown and can be designed in many ways. In FIG. 2A, reservoir R holding the lubricating fluid to be injected into a patent's joint space is part of pump P. Alternatively, reservoir R could be separate from pump P and connected thereto, e.g. as basically shown in FIG. 2B. In FIG. 2A, however, a movable or flexible wall 1410 of a pump P, which may be realized as a piston or the like, is electrically (or manually) displaceable so as to intermittently pump lubricating fluid from reservoir R through fluid connection tube 1402 towards infusion needle 1403. The pump P could e.g. be motor-driven, and the motor could be automatically controlled so as to intermittently inject a certain amount of lubricating fluid at certain time intervals via the infusion needle 1403 into the joint space. Reservoir R, pump P and/or other components of the implanted lubrication device, such as the aforementioned motor, an automatic control for the motor, etc., are preferably implanted along with infusion needle 1403 and drive mechanism D. Of course, other appropriate modifications are possible, as will become apparent upon further consideration of other embodiments of the present invention.

In the lubrication device shown in FIG. 2A, as the pressure is increased in reservoir R by actuation of the movable/flexible wall 1410 this will result in a displacement of infusion needle 3 against the force of a spring 1411 of drive mechanism D. Thus, tip end 1408 of infusion needle 1403 will penetrate into the joint space to be lubricated. When return spring 1411 is completely compressed and the pressure exerted on the lubricating fluid by means of the moving/flexible wall 1410 is further increased, a ball valve 1412 will be displaced against a second return spring 1413 which is stronger than the first return spring 1411. That way, as long as the pressure is held at a sufficiently high level, lubricating fluid will be pumped from reservoir R through fluid connection tube 1402, hollow infusion needle 1403 and the needle's exit port 1409 into the patient's joint space. Upon pressure release, ball valve 1412 will close due to return springs 1411 and 1413, and then infusion needle 1403 will be retracted to its initial position as shown in FIG. 2A. This process will be periodically repeated depending on the condition and type of the joint to be lubricated such that an intermittent lubrication of the particular joint is achieved.

It should be noted that the force acting on infusion needle 1403 to advance the same may be calculated as the product of the actual pressure and the cross section of needle 1403. Since the cross section of a typical infusion needle is relatively small, high pressure will have to be exerted in order to penetrate into the joint space and to overcome the counteracting forces of return springs 1411 and 1413. It is therefore advantageous to construct drive mechanism D such that two strictly separated chambers are formed in front of and behind the drive mechanism. Thus, when the chamber behind drive mechanism D is kept at low pressure, such as ambient pressure, the force acting on infusion needle 1403 would correspond to the product of the actual pressure and the entire cross section of drive mechanism D and, thus, be substantially higher.

This is shown in FIG. 2B. Drive mechanism D comprises a piston 1414 to which infusion needle 1403 is attached as shown in FIG. 3. Piston 1414 separates a first chamber 1415a in front of piston 1414 and a second chamber 1415b behind piston 1414. While the pressure in first chamber 1415a corresponds to the pressure exerted by pump P, the pressure in second chamber 1415b can be kept at a lower value. For instance, chamber 1415b could be filled with a compressible gas. In that case, return spring 1411 could be dispensed with as the compressed air would already create a needle retraction force.

It is difficult to securely seal a gas chamber, however. Therefore, second chamber 1415b is instead filled with fluid, such as the lubricating fluid, and the liquid may be urged into a flexible volume 1416. The flexible volume 1416 could be of simple balloon type so as to fill up without exerting any strong counterforce. Alternatively, the flexible volume 1416 may comprise a gas chamber separated from the fluid of second chamber 1415b by a flexible membrane. Again, return spring 1411 could be dispensed with in this case.

Instead of the flexible volume 1416, a conduit 1417 (acting as fluid connection tube 1402) may connect second chamber 1415b with reservoir R. Thus, when infusion needle 1403 is advanced, fluid will be expelled from second chamber 1415b through conduit 1417 into reservoir R, and as infusion needle 1403 is retracted by means of return spring 1411, fluid will be drawn from reservoir R through conduit 1417 back into second chamber 1415b. Pump P and reservoir R are be implanted into the patient's body along with drive mechanism D and needle 1403, either remote thereof or as a single unit, if desired.

Figure 2C:
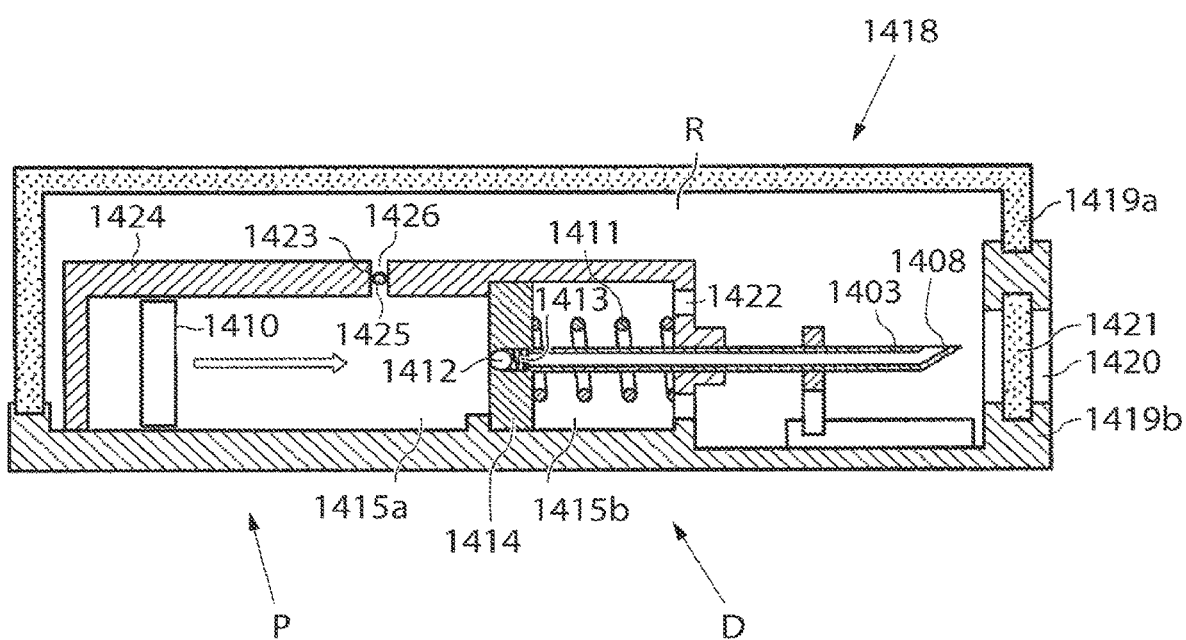
FIG. 2C shows a cross sectional view of a compact embodiment of the implantable infusion device.
Figure 3:
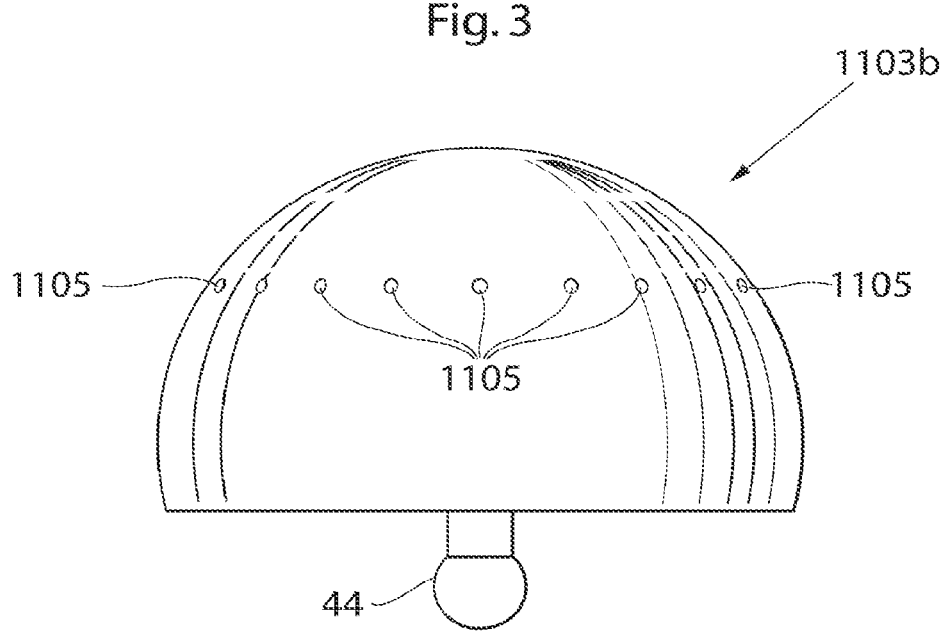
FIG. 3 shows the medical device according to one embodiment comprising an artificial contacting surface.

FIG. 2C shows a very compact lubrication device to be implanted subcutaneously and in close vicinity and in an appropriate relative position to the joint to be lubricated, such that the needle 1403 may intermittently advance into the joint upon activation by the drive mechanism D. The individual components of the device are contained within a unitary body 1418 comprising an outer wall 1419a, 1419b. The volume defined by outer wall 1419a, 1419b is completely filled with lubricating fluid. A wall portion 1419a is flexible so as to allow for volume changes occurring with each injection and refill. Wall portion 1419a is made from a polymer material which is self-sealing with respect to the penetration of an infusion needle 1403. The lubrication device can thus be refilled with lubricating fluid through the polymer wall portion 1419a while being implanted subcutaneously.

The other wall portion 1419b is rigid to provide some stability for the individual components contained within body 1418. A window area 1420 is formed in rigid wall portion 1419b and a penetration membrane 1421 is sealingly press fitted in window area 1420. Penetration membrane 1421 is made from a self-sealing material in respect of penetrations resulting from infusion needle 1403, which infusion needle is arranged for penetrating window area 1420 and thereby penetrating into the joint space to be lubricated.

Needle 1403 is connected to a piston 1414 separating a first chamber 1415a in front of piston 1414 and a second chamber 1415b behind piston 1414, as discussed above in reference to FIG. 2B. A return spring 1411 and a ball valve 1412 with a return spring 1413 are also provided. Openings 1422 are provided to connect second chamber 1415b to reservoir R so that when the pressure is raised in first chamber 1415a piston 1414 may expel lubricating fluid from second chamber 1415b through openings 1422 into reservoir R, which reservoir R is approximately at ambient pressure.

The pressure in first chamber 1415a is increased by means of a pump P comprising a movable/flexible wall 1410 moved forth and back by an appropriate drive mechanism, motor or the like. A flow passage 1423 is formed in a housing 1424 in which piston 1410 is slidably arranged. The flow passage has a flow constriction 1425 and an exit opening 1426 within the housing 1424.

The infusion device shown in FIG. 2C functions as follows. When the movable/flexible wall 1410 is actuated (i.e. moved in the direction of the arrow), the lubricating fluid contained in first chamber 1415a will not flow back into reservoir R through flow passage 1423, due to flow constriction 1425 in flow passage 1423, but will urge piston 1412 with needle 1403 towards window area 1420 while expelling lubricating fluid from second chamber 1415b through openings 1422 into reservoir R. When piston 1412 is in its end position and the movable/flexible wall 1410 is further moved in arrow direction, the pressure in first chamber 1415a will eventually rise to a level sufficiently high to overcome the spring force of return spring 1413, thereby opening ball valve 1412 and allowing lubricating fluid to be discharged through hollow needle 1403, the tip end 1408 of which has meanwhile penetrated membrane 1418 and the joint at which the body 1418 of the lubrication device is appropriately positioned. Upon a release of the pressure in the first chamber 1415a due to backward sliding of movable/flexible wall 1410, ball valve 1412 will immediately close and piston 1412 with infusion needle 1403 will be simultaneously drawn back into its retracted position. The flow passage 1423 is needed to allow movable/flexible wall 1410 to move further backwardly even after piston 1412 has reached its starting position, thereby drawing additional lubricating fluid from reservoir R into first chamber 1415a, which additional lubricating fluid compensates the amount of lubrication liquid delivered to the patient during the intermittent injection cycles. In addition to the intermittent advancing and retracting capabilities of drive mechanism D, the drive mechanism of the lubrication device shown in FIG. 2C may further comprise means for laterally displacing the tip end 1408 of infusion needle 1403 as to prevent fibrosis or the like.

The lubrication device shown in FIG. 2C provides several advantages such as not involving any gas chambers and not requiring any particular sealing of movable/flexible wall 1410 and piston element 1412. It should be noted that all components of the infusion device shown in FIG. 2B may be made from polymer material, although it is preferable that at least infusion needle 1403 and return springs 1411, 1413 be made from an inert metal.

Figure 2D:
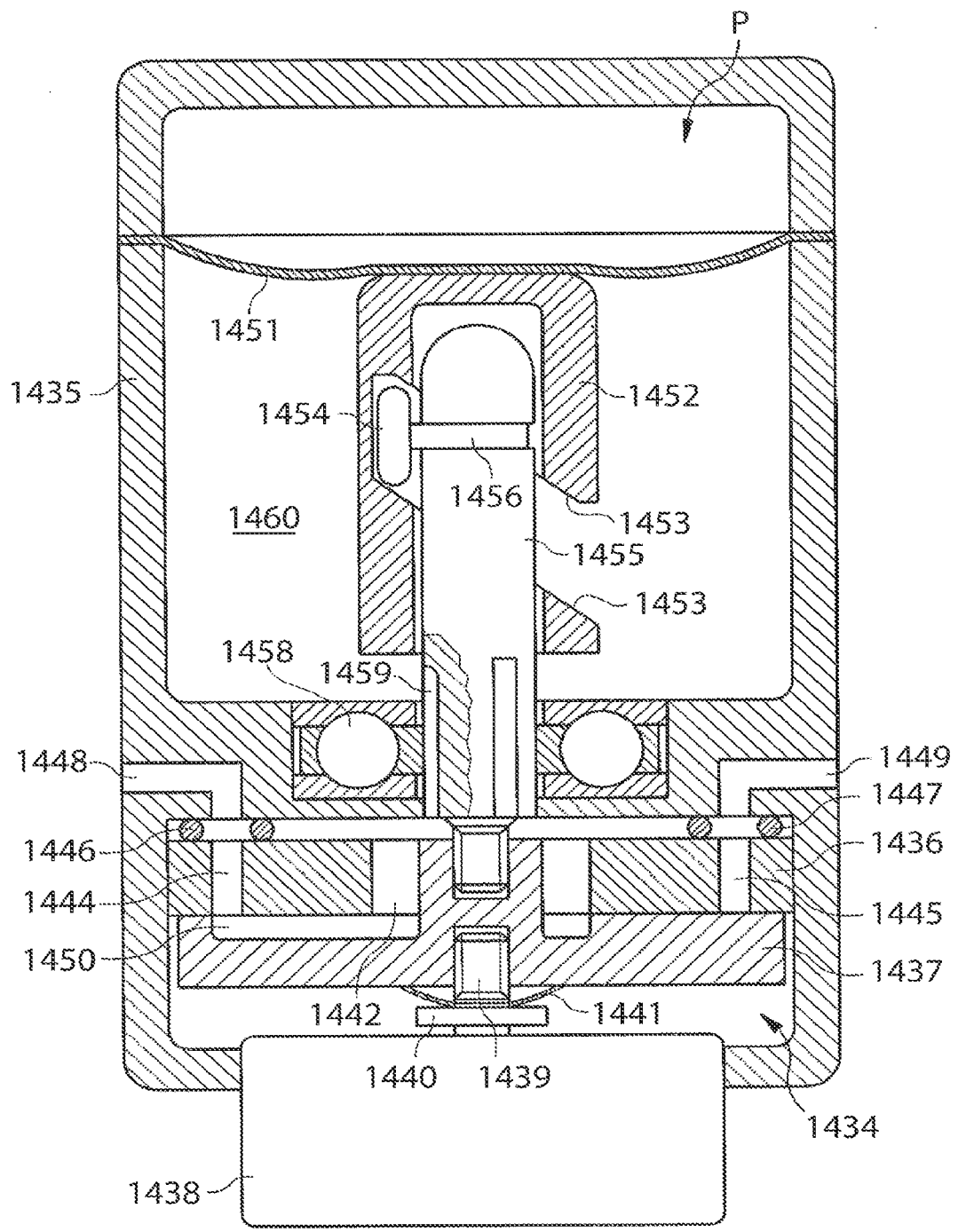
FIG. 2D shows a motor-driven pump unit suitable for use in connection with the embodiment shown in FIG. 1F.

FIG. 2D shows a cross-sectional view of a motor-pump unit that could be used in connection with the arrangement shown in FIG. 1F. This motor-pump unit is extensively described in WO 2004/012806 A1 and the other pump units disclosed therein may be employed in connection with the present invention as well. The motor-pump unit comprises a valve pump assembly, wherein a membrane pump P and a valve pump device 1434 constitute two main elements of the assembly mounted in a cylindrical housing 1435. Valve device 1434 includes a first valve member in the form of a ceramic disc 1436 stationary mounted on and fixed to housing 1435, and a second valve member in the form of a ceramic disc 1437 facing and touching ceramic disc 1436 and rotatable relative to stationary disc 1436. A motor 1438 is mounted on housing 1435 enclosing ceramic discs 1436 and 1437. Motor 1438 includes a splined motor shaft coupled to corresponding splines in a lower central hole in rotatable disc 1437 to allow disc 1437 to move somewhat in an axial direction relative to motor shaft 1439, although disc 1437 follows the rotation of motor 1435. On motor shaft 1439 there are mounted a stop member 1440 and a spring washer 1441 that exerts a slight amount of pressure against disc 1437 to urge it against stationary disc 1436.

Pump P includes a pump membrane 1451 that can be any kind of membrane. Preferably, membrane 1451 is a metal membrane, for example a titanium membrane, or a type of coated plastic material for achieving long life and avoiding diffusion of liquid through membrane 1451 over time. An operation device, which in this embodiment is incorporated in the valve pump assembly, includes a cam sleeve 1452 which has a cut-out groove with two opposite cam surfaces 1453, a cam wheel 1454, which rotates in the cut-out groove pushing against cam surfaces 1453, and a pump shaft 1455 connected to rotary disc 1437. Cam wheel 1454 is mounted via a cam wheel shaft 1456 onto pump shaft 1455. Pump shaft 1455 rotates because it is connected to rotating disc 1437 via a splined shaft 1461 that is coupled to corresponding splines in an upper central hole 1461 in rotatable disc 1437. The described spline coupling allows disc 1437 to move somewhat in an axial direction relative to pump shaft 1455. Pump shaft 1455 is mounted in an encapsulated ball-bearing 1458 and is stationary in an axial direction with respect to ball-bearing 1458. Several elongated grooves 1459 on pump shaft 1455 extend past ball-bearing 1458 and serve as liquid flow passages between first channel 1442 of stationary disc 1436 and a pump chamber 1460 under membrane 1451.

When motor 1438 is rotating, membrane 1451 moves up and down. As membrane 1451 moves up and down, rotatable disc 1437 connects first channel 1442 alternately to second and third channels 1444 and 1445 so that liquid is either transmitted from second channel 1444 or third channel 1445 to pump chamber 1460 or received from pump chamber 1456 by second channel 1444 or third channel 1445. In FIG. 2D, first channel 1442 is shown as being connected to second channel via opened channel 1450 so that second channel 1444 receives liquid through first channel 1442 from chamber 1460.

The particular material selected for discs 1436 and 1437 is important because the selected material must be able to function using very fine tolerances without such discs sticking to one another over time. There are several materials available on the market that are suitable for this purpose, e.g. ceramic or ceramic mixed with other materials, such as carbon fiber.

FIG. 3 shows the medical device according to an embodiment in which the medical device is adapted to replace the contacting surface of the caput femur of the femoral bone of a human patient. The medical device according to this embodiment the artificial contacting surface 1103*b* of the medical device comprises a plurality of channels adapted to lubricate the hip joint of a human patient with a lubricating fluid. The medical device further comprises a fixating portion 44 for fixating the medical device to the caput femur and/or the collum femur of the femoral bone.

Figure 4:
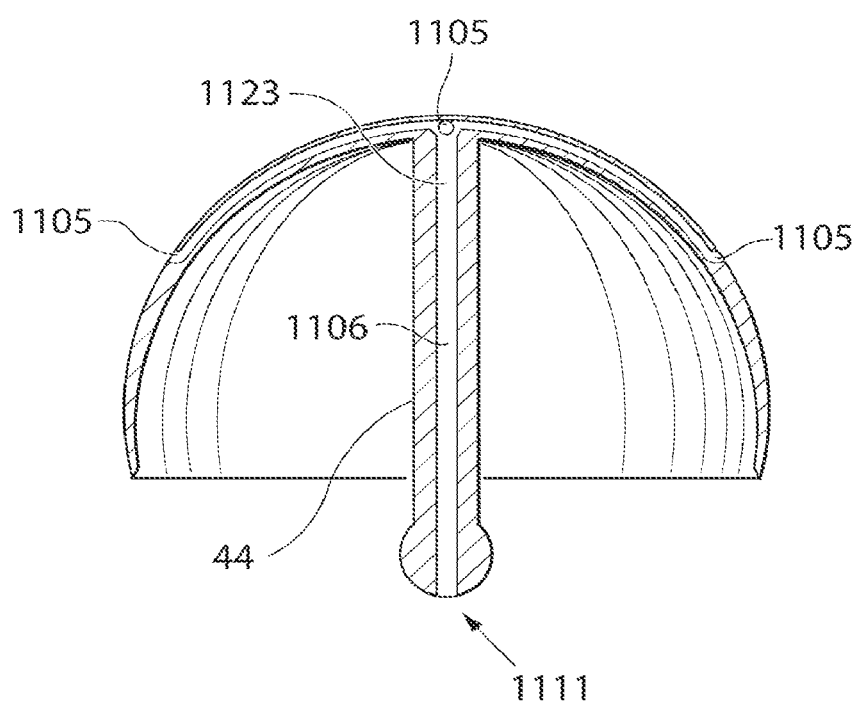
FIG. 4 shows the medical device according to one embodiment comprising an artificial contacting surface, in section.

FIG. 4 shows the medical device according to FIG. 3 in section, showing the medical device comprising a plurality of channels in fluid connection with a reservoir (not shown) through a conduit 1106 placed centrally in the fixating portion 44, the channels 1105 being fully integrated in the medical device. The conduit 1106 transports lubricating fluid to the inlet 1123 for further distribution to the channels 1105. The conduit ends up in a connecting section 1111 which is adapted to connect the conduit to a second conduit 1106 or a reservoir, or additional channels.

Figure 5:
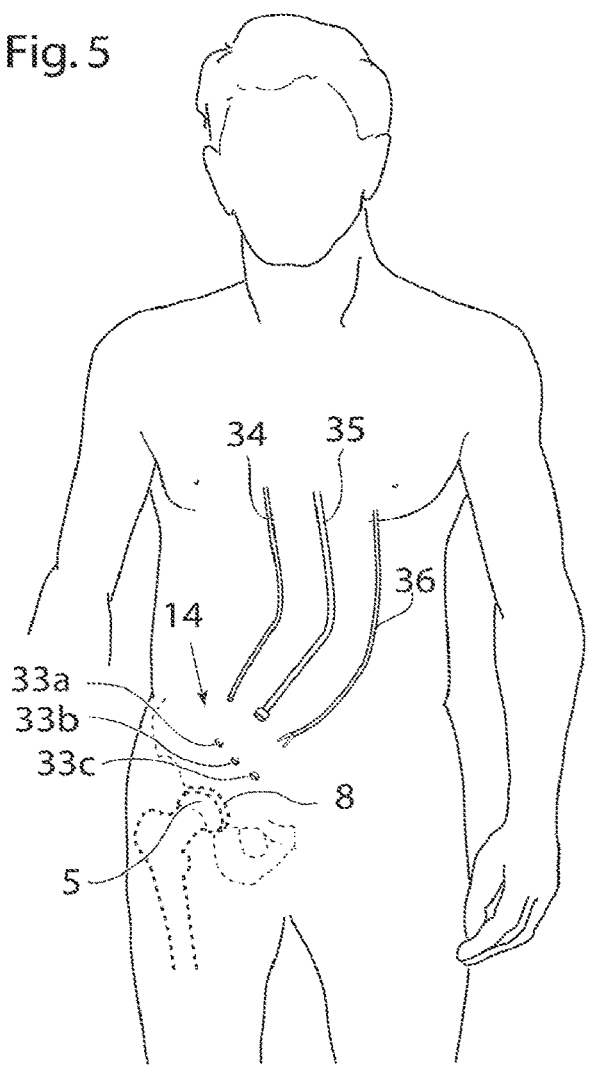
FIG. 5 shows a frontal view of a human patient displaying the hip joint.

FIG. 5 shows a frontal view of the body of a human patient, illustrating a laparoscopic/arthroscopic method of operating the hip joint to provide a medical device according to any of the embodiments herein from the opposite side from acetabulum 8. The hip joint comprises the acetabulum 8 and the caput femur 5. The small incisions 14 in the abdominal wall of the human patient allows the insertion of laparoscopic/arthroscopic trocars 33*a,b,c* into the body of the patients. Whereafter one or more camera 34, a surgical instrument adapted to create a hole in the pelvic bone 35, or instruments 36 for introducing, placing, connecting, attaching, creating or filling an implantable medical device, can be inserted into the body through said laparoscopic/arthroscopic trocars 33*a,b,c*.

Figure 6:
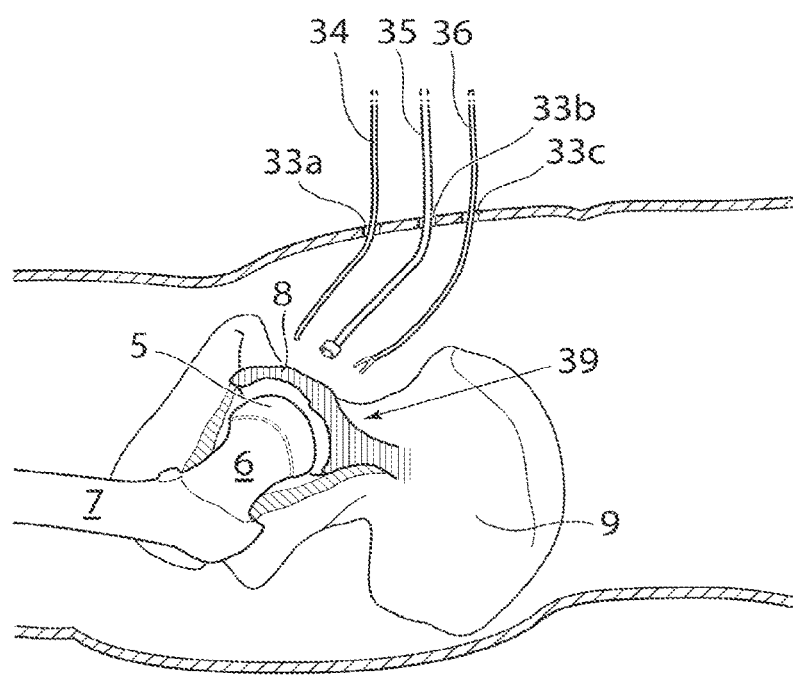
FIG. 6 shows a lateral view of a human patient, in section, when a laparoscopic/arthroscopic procedure is being performed.

FIG. 6 shows a lateral view of the body of a human patient, with the hip joint shown in section. The hip joint comprises a caput femur 5 placed at the very top of collum femur 6 which is the top part of the femur bone 7. The caput femur 5 is in connection with the acetabulum 8 which is a bowl shaped part of the pelvic bone 9. Laparoscopic/arthroscopic trocars 33*a,b,c* is being used to reach the hip joint 39 with one or more camera 34, a surgical instrument 35 adapted to create a hole in the pelvic bone 9, or instruments 36 for introducing, placing, connecting, attaching, creating or filling an implantable medical device.

Figure 7:
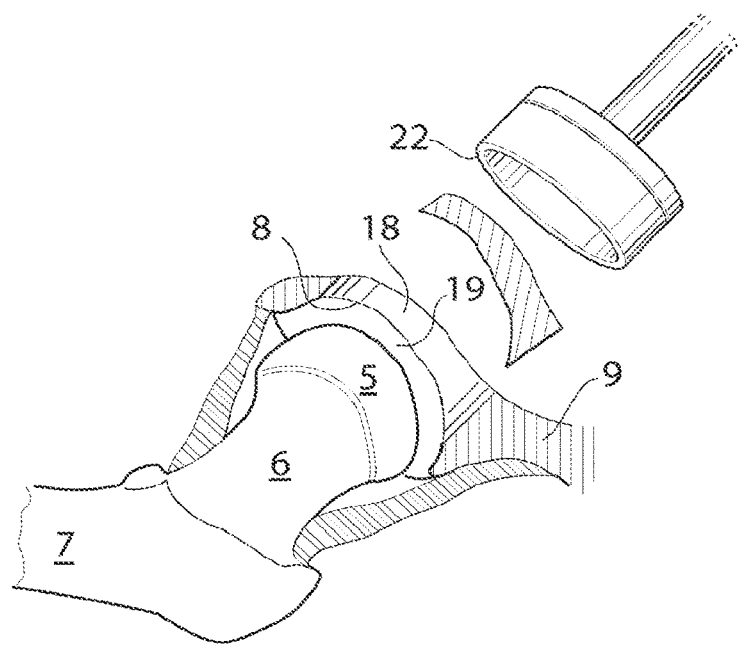
FIG. 7 shows the hip joint in section when a hole in the pelvic bone is being created.

FIG. 7 shows the creation of a hole 18 in the pelvic bone 9, after the pelvic bone 9 has been dissected. The hole 18 is created from the abdominal side of the pelvic bone 9 through repetitive or continuous movement of a hole creating device 22 placed into the human patient from the abdominal side of the pelvic bone 9. The hole 18 passes through the pelvic bone 9 from the opposite side from acetabulum 8 and into the hip joint 19. According to a first embodiment the hole 18 is large which allows an implantable medical device to pass through the hole 18 in its full functional size.

Figure 8A:
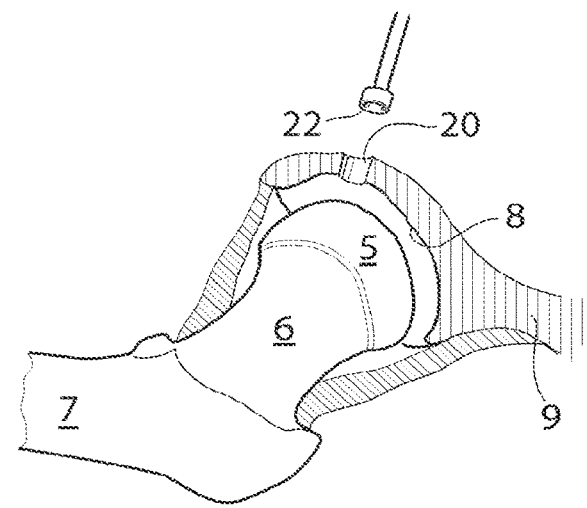
FIG. 8a shows the hip joint in section when a small hole in the pelvic bone is being created.

FIG. 8*a* shows a second embodiment in which the hole 20 created in a surgical or laparoscopic/arthroscopic method is much smaller as shown in FIG. 8*a* allowing the hole creating device 22 creating the hole 20 to be smaller, and thus also the incision and dissection performed in the human body.

Figure 8B:
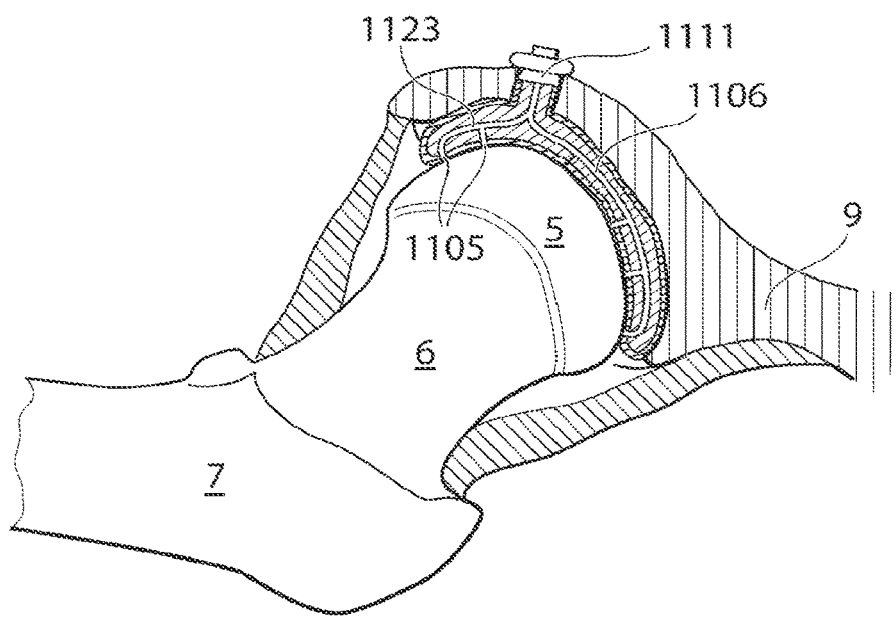
FIG. 8b shows the hip joint in section when a medical device has been provided through a hole in the pelvic bone.

FIG. 8*b* shows the hip joint in section when a medical device has been provided between the caput femur 5 and the acetabulum. The medical device according to this embodiment comprises multiple channels 1105 connected to a conduit 1106 which in turn is connected to a connecting portion placed in the hole in the pelvic bone 9. The conduit 1106 transports lubricating fluid to the inlet 1123 for further distribution to the channels 1105. For insertion through a hole 18 in the pelvic bone 9 being smaller than the medical device the medical device could be rolled or compressed, or according to another embodiment, moulded in place either in a mould adapted to be resorbed by the human body, melt or serve as the surface of the medical device. The medical device could be adapted to be fixated using adhesive or a mechanical fixating element.

Figure 9A:
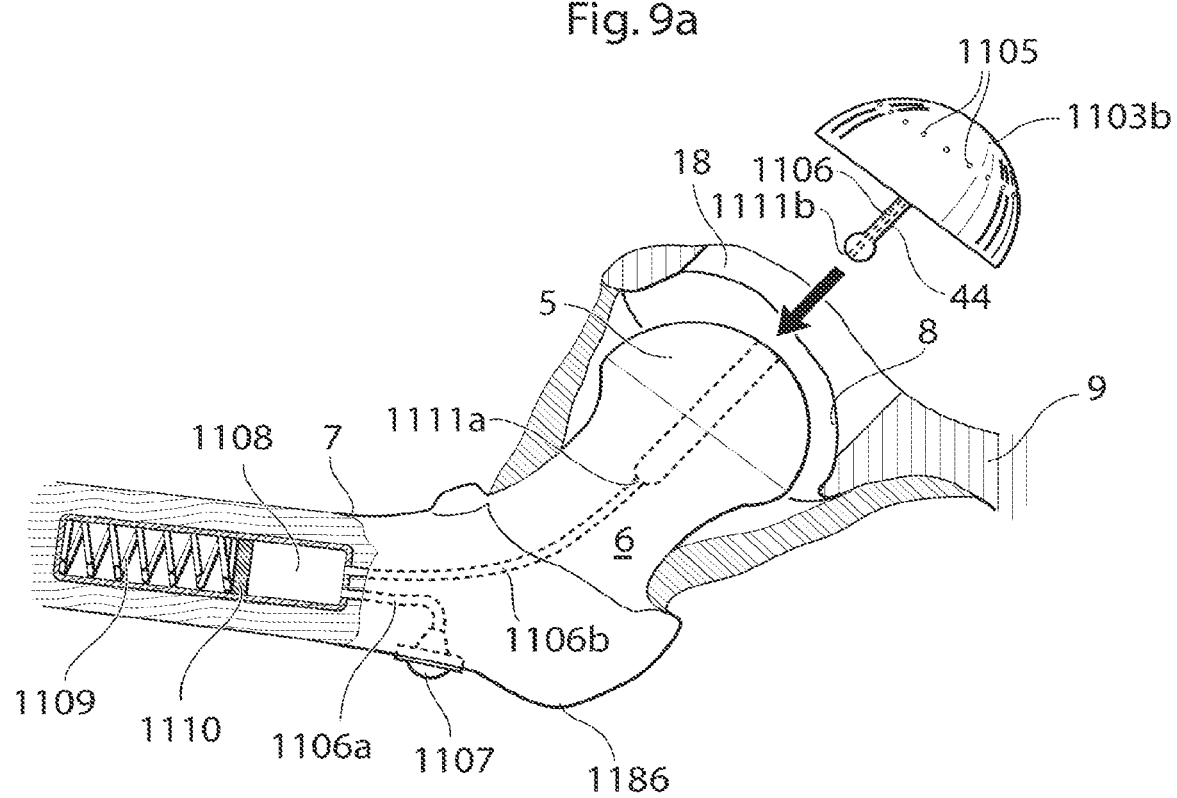
FIG. 9a shows the hip joint in section when a medical device is being provided through a hole in the pelvic bone.

FIG. 9*a* shows a hip joint in section when a medical device is being provided, through a hole 18 in the pelvic bone 9 for replacing the contacting surface of the caput femur 5. The medical device comprises an artificial contacting surface 1103*b* and a fixating portion 44 placed centrally in the medical device and adapted to fixate the medical device to the caput femur 5. The medical device comprises a plurality of channels 1105 which exits at the artificial contacting surface for lubricating the hip joint. The channels are in fluid connection with a conduit 1106 which in turn is connected to an interconnecting part 1111*b* adapted to connect the conduit to a second conduit 1106*b* or a second portion of the conduit 1106*b*, which in turn is in fluid connection with a reservoir 1108 placed in the femoral bone 7 of the human patient. The reservoir 1108 is placed in the femoral bone 7 and is adapted to hold a pressurized lubricating fluid, which according to the embodiment shown in FIG. 9*a* is pressurized by means of said reservoir 1108 being spring loaded by means of a spring 1109 in connection with a movable wall portion in the form of a piston 1110 pressurizing the lubricating fluid. The reservoir 1108 is furthermore connected to an injection port 1107 which is positioned in connection with the femoral bone 7 below the greater trochanter 1186, however, any other suitable placement is also conceivable, in connection with bone, in a cavity or subcutaneously. The medical device is according to the embodiment of FIG. 9*a* operable using a pressurized reservoir, however according to other embodiments the medical device is operable by a powered operating device, such as an implantable pump, which could be powered by direct propulsion, such as inductive or magnetic propulsion, or by an accumulated energy source, such as a battery. The channels or conduits could according to one embodiment (not shown) comprise a valve for closing the flow of lubricating fluid through the conduit 1106 or channel 1105, thereby closing the connection between the reservoir and the artificial contacting surface. The valve could be powered and adapted to be controlled form outside of the human body by means of for example a remote control.

Figure 9B:
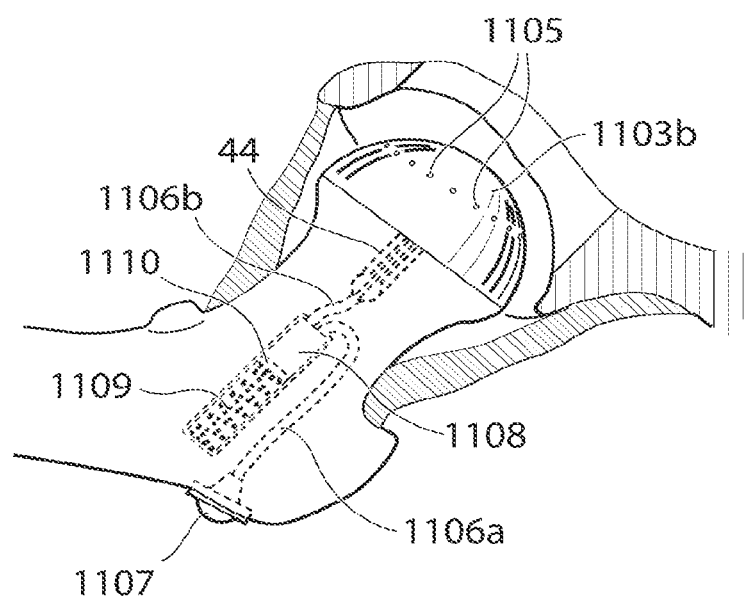
FIG. 9b shows the hip joint in section when a medical device has been provided through a hole in the pelvic bone.

FIG. 9*b* shows the hip joint in section when a medical device according to another embodiment has been provided to the hip joint, replacing the contacting surface of the caput femur. The medical device comprises an artificial contacting surface 1103*b* comprising a plurality of channels 1105 which are connected to a conduit 1106, 1106*b* placed in fixating part of the medical device. The conduit is in turn in fluid connection with a reservoir 1108 placed inside of the femoral bone, preferably in the cancellous parts of the femoral bone, the reservoir is thereby in fluid connection with the channels of the medical device for lubricating the artificial contacting surface 1103*b* of the medical device.

FIG. 10 shows the hip joint in section when an implantable medical device adapted to replace the acetabulum contacting surface is being provided. The medical device comprises an artificial acetabulum surface 65 comprising a plurality of channels connected to a conduit 1106 by an inter-connecting part 1111. The medical device is according to the embodiment shown in FIG. 10 adapted to be placed in a hole 18 in the pelvic bone 9 for replacing the acetabulum contacting surface 65. FIG. 10 furthermore shows a unit to which the conduit 1106 is connected, according to one embodiment the unit comprises a reservoir 1108 and two pressure creating devices 1113*a*, 1113*b* adapted to create a pressure for pressurizing the lubricating fluid for pressing said lubricating fluid through the conduit 1106 and further through the plurality of channels 1105 for lubricating the implantable medical device. The conduit 1106 transports lubricating fluid to the inlet 1123 for further distribution to the channels 1105. The pressure creating devices could be spring loaded or comprise of a pressurized gas filled element which is further pressurized by the injecting of a lubricating fluid into the reservoir 1108. The unit further comprises an injection port 1107 which comprises a self sealing membrane 1112, which preferably is a Parylene coated silicone membrane. According to another embodiment the unit comprises a powered operation device such as a pump housed in the container 1113*a* which pumps the lubricating fluid from the reservoir 1108 through the conduit 1106 to the plurality of channels 1105. According to one embodiment the pump is powered by a battery housed in the compartment 1113*b*.

FIG. 11*a* shows a surgical instrument adapted to insert a medical device according to any of the embodiments herein, or a mould for creating a medical device, according to a first embodiment. The surgical instrument comprises a gripping portion 76 and a handling portion 77. According to the embodiments shown in FIGS. 11*a,b,c* the instrument further comprises a rotation element 78 that enables the gripping part 76 to rotate in relation to the handling part 77, however it is equally conceivable that the surgical instrument lacks this rotation element 78.

FIG. 11*b* shows the surgical instrument adapted to insert a prosthesis, prosthetic parts or parts needed to create or provide a hip joint surface, according to a second embodiment. According to this embodiment the surgical instrument further comprises a parallel displaced section 79, which increases the reach of the instrument and facilitates the reaching of the hip joint through a hole in the pelvic bone from the opposite side from acetabulum.

FIG. 11*c* shows the surgical instrument adapted to insert a prosthesis, prosthetic parts or parts needed to create or provide a hip joint surface, according to a third embodiment. According to this embodiment the surgical instrument further comprises two angle adjusting members 80*a,b*. The angle adjusting members could be adjustable for varying the angle of said gripping part 76 in relation to the handling portion 77, or fixed in an angle suitable for creating operating in a hip joint through a hole in the pelvic bone from the opposite side from acetabulum 8.

FIG. 12 shows the hip joint in section when a medical device has been provided. The implantable medical device is adapted to replace the acetabulum surface and is inserted through a hole 18 in the pelvic bone 9, however, in other embodiments it is equally conceivable that the medical device is adapted to be inserted through a hole in the femoral 7 bone or the hip joint capsule. The medical device comprises a plurality of channels 1105 interconnected through a conduit 1106 which places the channels 1105 in fluid connection with each other. The conduit 1106 transports lubricating fluid to the inlet 1123 for further distribution to the channels 1105. The conduit 1106 is further connected to a first portion of an interconnecting part 1111 which is adapted to be connected to a second portion of an interconnecting part 1111b. The interconnecting part 1111 connects a first portion of the conduit 1106 to a second portion of the conduit 1106, enabling a first portion of the conduit 1106 to be inserted from the acetabulum side of the pelvic bone 9 and a second portion of the conduit 1106 to be inserted from the pelvic side, or opposite acetabulum side of the pelvic bone 9. The connection of two portions of the conduit 1106 is particularly beneficial when the medical device has been inserted through a hole 18 in the femoral bone 7 or the hip joint capsule and the reservoir 1108 is implanted in the abdominal region of the human patient, or in another area on the abdominal side of the pelvic bone 9. The conduit 1106 is then further connected to the reservoir 1108 and adapted to transport a lubricating fluid from the reservoir 1108 to an area of the hip joint. The reservoir 1108 is according to the embodiment shown in FIG. 12 adapted to place the lubricating fluid under pressure by means of a spring 1109 exerting a force on a movable wall portion in the form of a piston 1110 pressing the lubricating fluid through the conduit 1106 and further through the channels 1105. The reservoir 1108 further comprises an injection port 1107 placed in the top part of the reservoir 1108 for refilling the reservoir 1108 and in the same event increasing the pressure of the lubricating fluid.

Figure 13A:
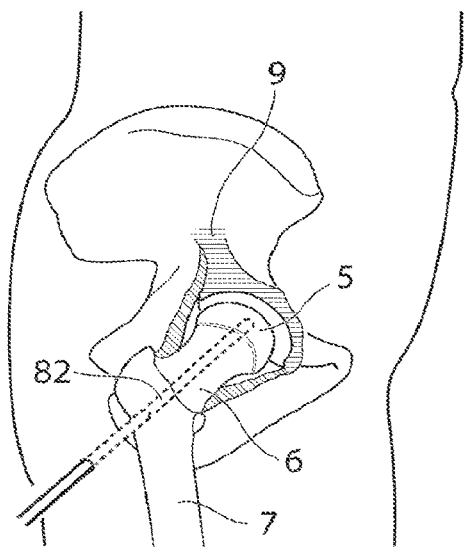
FIG. 13a shows the lateral view of a hip joint ion section when a hole is being created through the femoral bone.

FIG. 13a shows a human patient in a lateral view showing the hip joint in section. The femoral bone 7 has a proximal part comprising the collum femur 6 and most proximal the caput femur 5. In FIG. 13a a hole 82 is being created from an incision made in the thigh, the hole travels into the femoral bone 7, following the collum femur 6 and exiting through the caput femur 5 and thus into the hip joint. The hole is used to provide the hip joint with a medical device which preferably is possible to roll or bend for insertion through said hole 82.

Figure 13B:
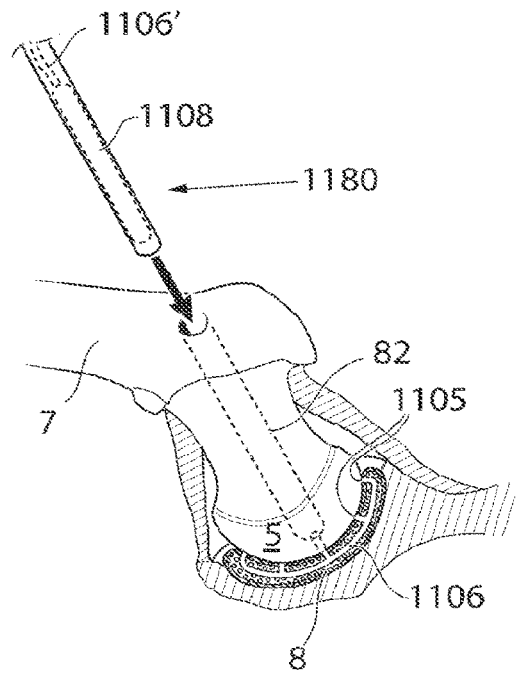
FIG. 13b shows a hip joint in section when a medical device is being provided through a hole in the femoral bone.

FIG. 13b shows the hip joint in section when the medical device has been provided through the hole 82 in the femoral bone 7 and fixated in the acetabulum bowl 8. The medical device comprises a plurality of channels 1105 connected to each other by a conduit 1106. According to other embodiments, the medical device could be provided through the hip joint capsule, or a hole in the pelvic bone 9. After the medical device has been provided, a tool 1180 housing a reservoir 1108 connected to a conduit 1106' is used to provide the reservoir 1108 to the hole 82 in the femoral bone 7 and to connect the reservoir to the conduit 1106 of the medical device.

Figure 13C:
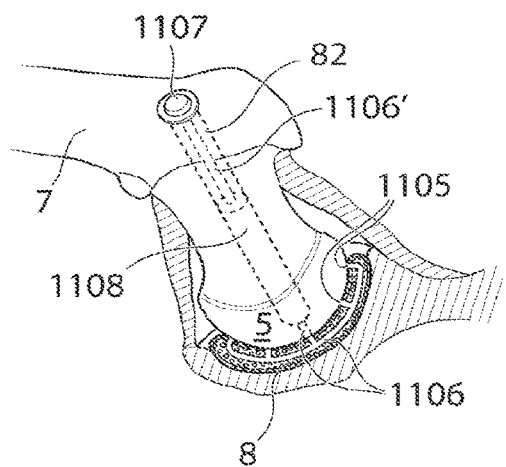
FIG. 13c shows a hip joint in section when a medical device has been provided through a hole in the femoral bone.

FIG. 13c shows the hip joint in section when the reservoir 1108, placed in the hole 82 in the femoral bone 7 has been connected to the medical device. Furthermore a conduit 1106' reaching from the reservoir 1108 to an injection port 1107 for refilling and/or pressurizing the reservoir 1108.

Figure 13D:
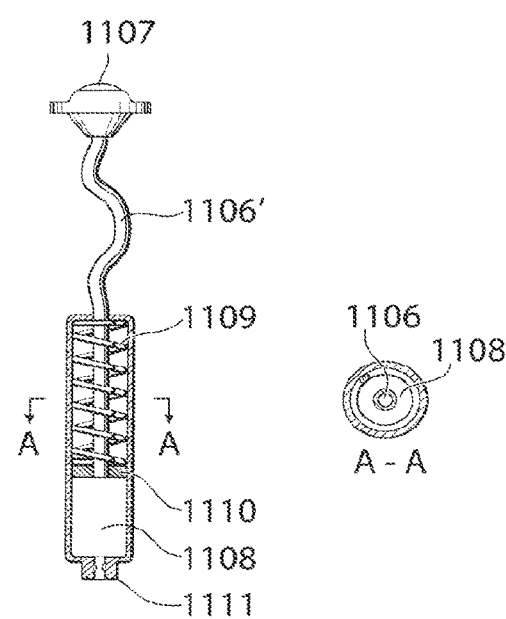
FIG. 13d shows a reservoir adapted to be connected to a medical device, in further detail.

FIG. 13d shows the reservoir unit in further detail, the reservoir unit comprises an inter-connecting portion 1111 placed at the end part of the reservoir unit, a pressurized reservoir 1108, which according to the embodiment of FIG. 13d is pressurized by means of a spring 1109 pushing a movable wall portion 1110 in the form of a piston 1110. The reservoir unit further comprises a conduit 1106' in connection with the reservoir, and in connection with an injection port 1107, for filling the and/or pressurizing the reservoir 1108 comprising the lubricating fluid. The injection port 1107 comprises a self sealing membrane, which could be a self sealing Parylene coated silicone membrane, to inhibit cell migration on the surface of the injection port. The section A-A shows the centrally placed conduit 1106 in the center of the reservoir 1108 for filling and/or pressurizing the reservoir 1108.

Figure 14:
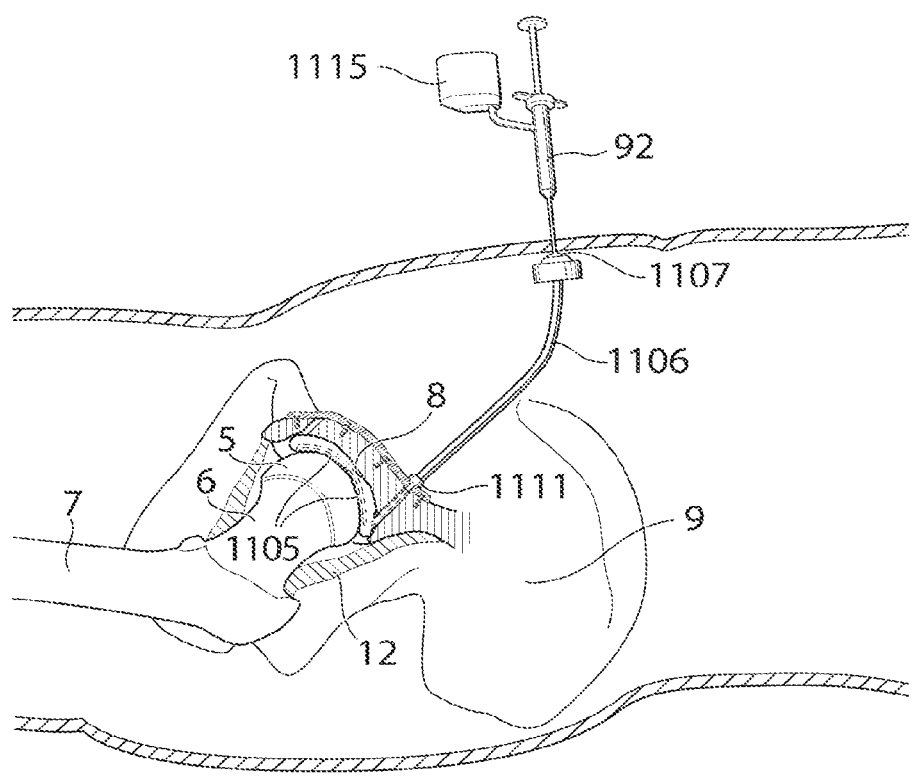
FIG. 14 shows the injection of a lubricating fluid into an implantable injection port.

FIG. 14 shows a lateral view of a human patient in section, when a lubricating fluid is being injected into an injection port 1107, by means of an injecting member 92 comprising a container 1115 adapted to contain the lubricating fluid to be injected. The injection port is connected to an implantable medical device placed in the hip joint through a conduit 1106 adapted to supply the fluid connection between the injection port and the medical device. The medical device in turn comprises a plurality of channels 1105 for lubricating the artificial contacting surfaces and thereby lubricating the hip joint. According to the embodiment shown in FIG. 14 the medical device has been supplied from the abdominal side of the pelvic bone 9 through a hole made in the pelvic bone which afterwards has been refilled with the removed bone plug and sealed and fixated with a mechanical fixating part attached with screws. According to other embodiments the medical device is provided from the hip joint side of the pelvic bone 9 through the hip joint capsule 12 or the femoral bone 7 and thereafter connected to the conduit 1106 on the abdominal side of the pelvic bone 9 through an interconnecting part 1111. This enables the placing of the injection port 1107 in the abdominal region, subcutaneously, in a cavity and/or supported by the muscular or fascia tissue.

Figure 15:
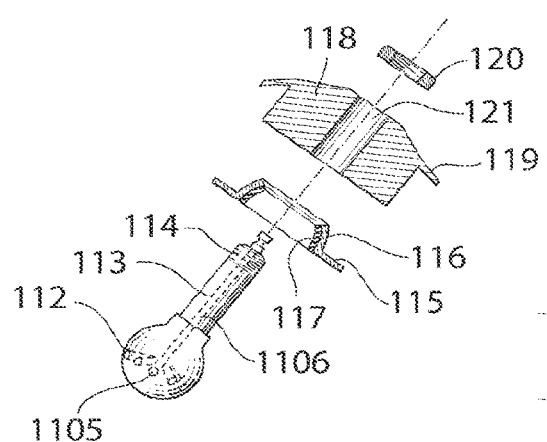
FIG. 15 shows an implantable medical device in an opposite embodiment.

FIG. 15 shows the medical device in an opposite embodiment where the medical device comprises a first artificial contacting surface 112 comprising a convex shape towards a centre of the hip joint. The first artificial contacting surface 112 is adapted to be fixated to the pelvic bone 9 of the human patient. The artificial convex hip joint surface 112 is adapted to be fixated to the pelvic bone 9, and is adapted to be inserted through a hole 18 in the pelvic bone 9. The medical device comprises a nut 120, comprising threads for securely fixating the medical device to the pelvic bone 9. The medical device further comprises a prosthetic part 118 adapted to occupy the hole 18 created in the pelvic bone 9 after the medical device has been implanted in the patient. The prosthetic part 118 comprises supporting members 119 adapted to be in contact with the pelvic bone 9 and assist in the carrying of the load placed on the medical device from the weight of the human patient in normal use. Normal use is defined as the same as a person would use a natural hip joint. Further the medical device comprises a locking element 116 comprising a surface 117 adapted to be in contact with the artificial convex hip joint surface 112. The locking element 116 further comprises fixating members 115 which are adapted to assist in the fixation of the locking member 116 to the caput femur 5 or collum femur 6, which in turns fixates the artificial convex hip joint surface 112. The artificial convex hip joint surface 112 is fixated to a attachment rod 113 comprising a thread 114 that corresponds to the thread of the nut 120 in connection with the prosthetic part 118. The medical device comprises a plurality of channels 1105 adapted to lubricate the artificial contacting surface 112. The plurality of channels 1105 are connected to each other through a conduit 1106 adapted to transport a lubricating fluid from a reservoir 1108 to the plurality of channels

1105 which are fully integrated in the artificial contacting surface 112 of the medical device for lubricating the artificial contacting surface 112 and thereby lubricating the hip joint.

Figure 16:
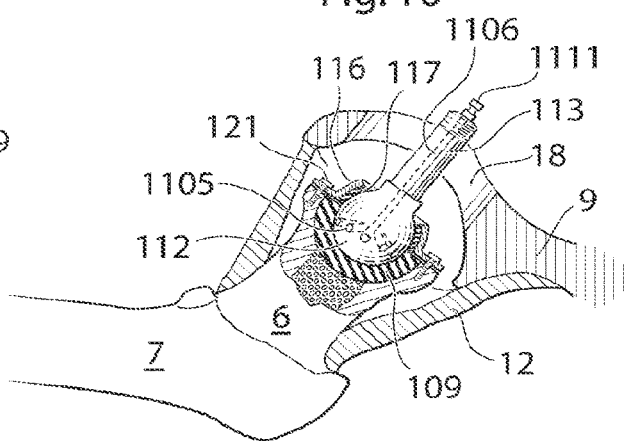
FIG. 16 shows a hip joint in section, when an implantable medical device in an opposite embodiment has been placed.

FIG. 16 shows the medical device according to FIG. 15 when said medical device is placed inside of the hip joint. The first artificial contacting surface 112 comprising a convex shape towards a centre of the hip joint is positioned in a second artificial contacting surface 109 comprising a concave shape towards the centre of the hip joint. The second artificial contacting surface 109 is placed and fixated in the caput 5 and collum femur 6 of the femoral bone an secured by a locking element 116 comprising a surface 117 facing the first artificial convex contacting surface 112. The medical device comprises a plurality of channels 1105 which are connected to a conduit 1106 placed centrally in the medical device for providing a lubricating fluid to the medical device and lubricate the artificial contacting surface 112 and thereby the hip joint.

Figure 17:
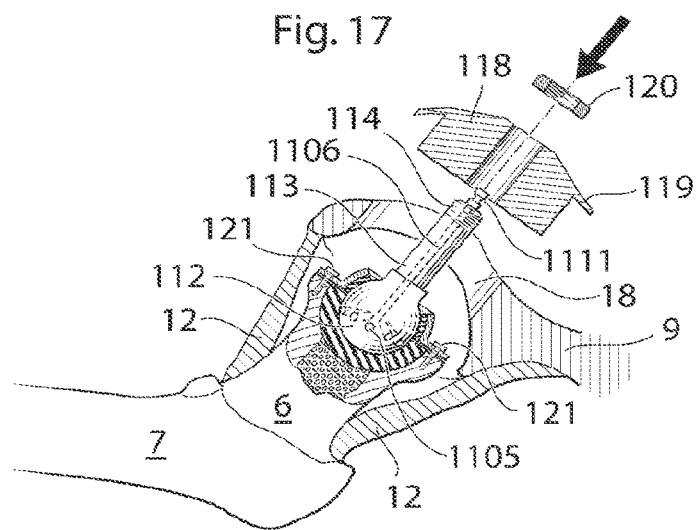
FIG. 17 shows a hip joint in section, when an implantable medical device in an opposite embodiment has been placed.

FIG. 17 shows the providing of a prosthetic part 118 to the hole 18 in the pelvic bone 9. The prosthetic part 118 comprises supporting members 119 adapted to be in contact with the pelvic bone 9 and assist in the carrying of the load placed on the medical device from the weight of the human patient in normal use.

Figure 18:
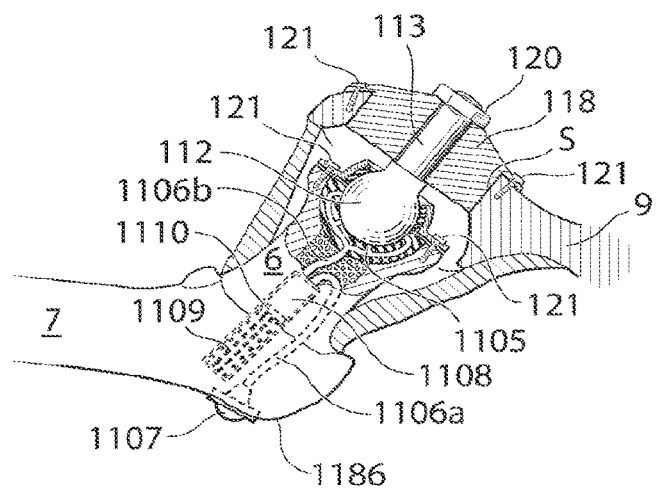
FIG. 18 shows a hip joint in section, when an implantable medical device in an opposite embodiment has been placed and connected to a reservoir.

FIG. 18 shows an alternative embodiment of the medical device in the opposite embodiment in which the part of the medical device comprising an artificial concave hip joint surface placed in the caput 5 and collum femur 6 comprises a plurality of lubricating channels 1105 which are connected to a conduit 1106*b* establishing a fluid connection between the medical device and the reservoir located in the cancellous bone of the collum femur 6. The reservoir is adapted to be refilled through an injection port 1107 which according to the embodiment of FIG. 18 is placed in connection with the femoral bone 7 and situated below the greater trochanter 1186. The reservoir unit, and the function thereof, is described in further detail with reference to FIGS. 9*a* and 9*b*. FIG. 18 furthermore shows the prosthetic part 118, when fixated to the pelvic bone 9 using screws 121. The screws could be assisted or replaced by an adhesive which could be applied in connection to the screws or at the surface S between the prosthetic part and the pelvic bone 9.

Figure 19:
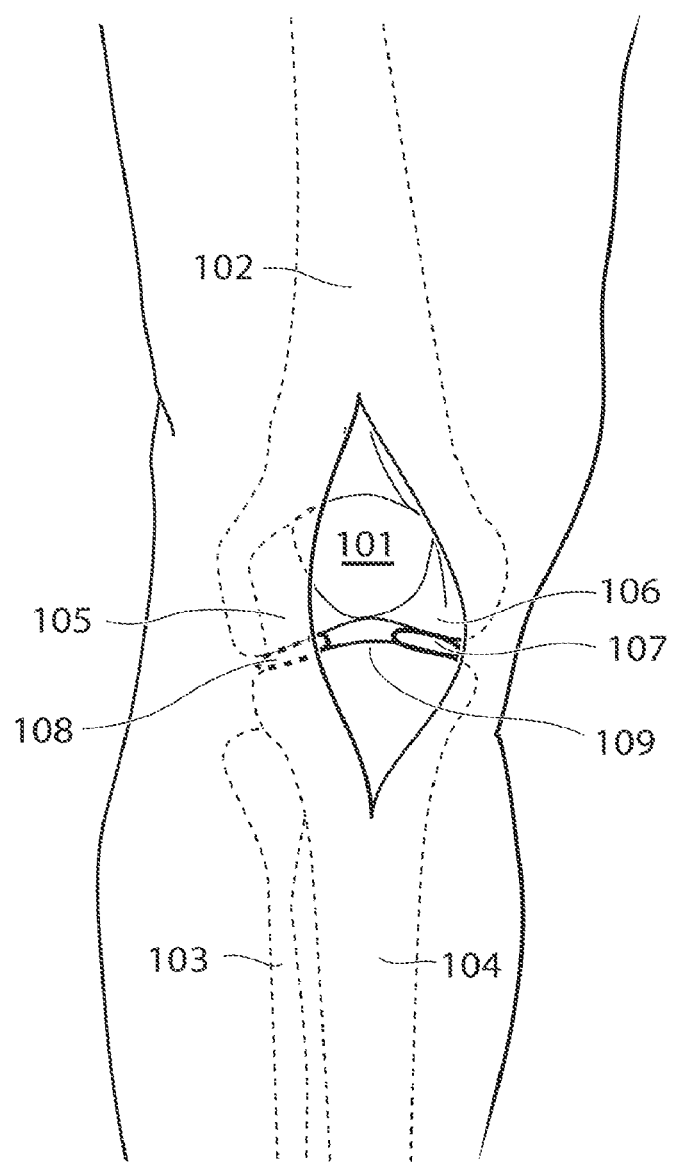
FIG. 19 shows a frontal view of a knee joint of a human patient.

FIG. 19 shows the right leg of a human patient. The femoral bone 102 having a distal part comprising the lateral condyle 105, the medial condyle 106 and an area between said lateral and said medial condyle. The sections of the distal part of the femoral bone 102 comprise contacting surfaces of the knee joint. The knee joint furthermore comprises the patella 101, which is a triangular bone which articulates with the femur 102 and covers and protects the knee joint. The knee joint also comprises the minisci 107, 108 which are cartilaginous elements within the knee joint which serve as articulating surfaces to protect the ends of the bones from rubbing on each other. The minisci 107, 108 also acts as shock absorbers in the knee joint, to absorb the shocks from the movement of the human patient. There are two minisci 107,108 in each knee, the medial meniscus 107 and the lateral meniscus 108. In patients with osteoarthritis the minisci 107, 108 which acts as articulating surfaces i.e. weight carrying surfaces are worn away and, in extreme cases, bone can be exposed in the joint. The knee joint is protected by the knee joint capsule also known as the articular capsule of the knee joint or the capsular ligament of the knee joint. The knee joint capsule is wide and lax; thin in front and at the side; and contains the patella 101, ligaments, minisci 107,108, and bursae, which are small fluid-filled sacs made of white fibrous tissue. The knee joint capsule consists of a synovial and a fibrous membrane separated by fatty deposits anteriorly and posteriorly.

FIG. 20 shows the knee joint when artificial knee joint surfaces 130, 116*a* has been provided to the distal part of the femoral bone 102 and the proximal part of the tibia bone 104. A lateral and medial channel 125*a,b* supplies the contacting surfaces and thereby the knee joint with lubricating fluid for reducing the friction of the knee joint.

FIG. 21 shows the body of a human patient in a frontal view where a reservoir unit 127 is implanted subcutaneously in the abdominal region of the human patient. The reservoir unit according to this embodiment comprises an operating device in the form of a pump 130 which is powered by a battery 128 for pumping a fluid from the reservoir 129 through a conduit to a channel 125 supplying the artificial contacting surfaces of the knee joint with a lubricating fluid. The reservoir unit is fixated to the muscular or fascia tissue 1181 of the abdominal wall through the muscular or fascia 1181 tissue being clamped between the reservoir unit and the injection port 1107 arranged at the outside of the muscular or fascia tissue 1181.

Figure 22A:
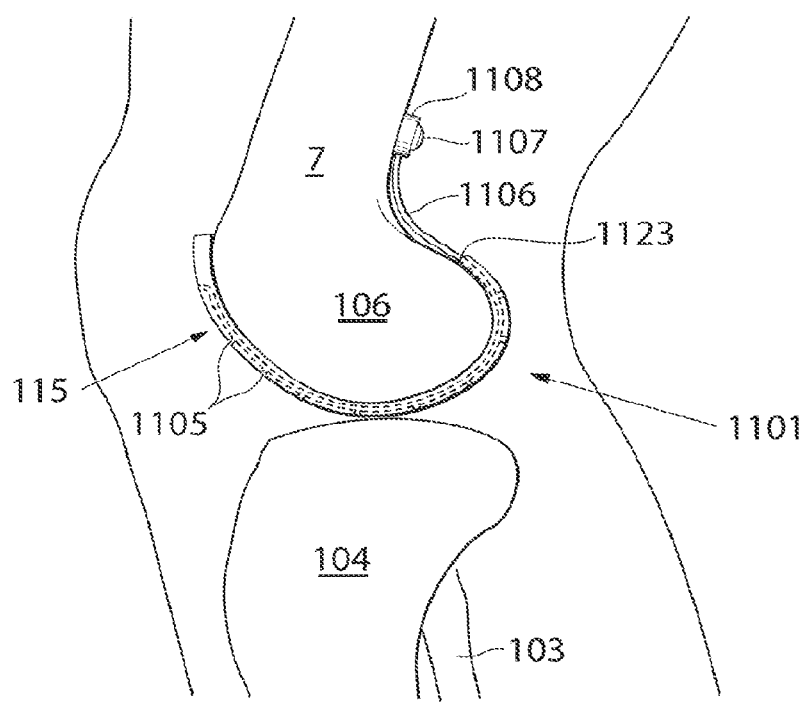
FIG. 22a shows a lateral view of a knee joint when a medical device has been provided to the femoral bone.

FIG. 22*a* shows an embodiment where the medical device comprises an artificial knee joint 115 surface clamps the medial, lateral or both the medial and lateral condyle 106 of the knee joint, being the distal portion of the femoral bone 7. The medical device, according to this embodiment comprises a plurality of channels 1105 for lubricating the artificial contacting surfaces, the plurality of channels are in fluid connection with each other through a conduit 1106 which in turn is in fluid connection with a reservoir 1108 comprising an injection port 1107 for refilling the reservoir or pressurizing the lubricating fluid contained in said reservoir 1108. The conduit 1106 transports lubricating fluid to the inlet 1123 for further distribution to the channels 1105.

Figure 22B:
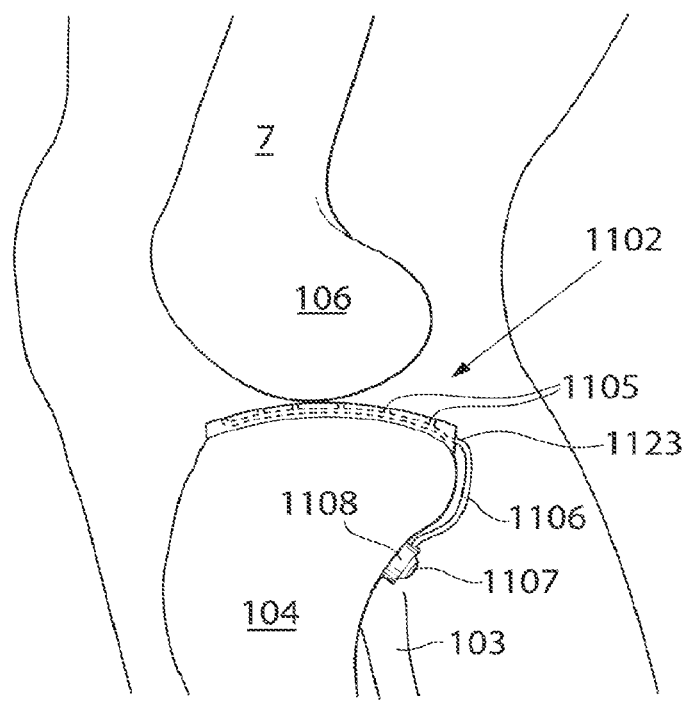
FIG. 22b shows a lateral view of a knee joint when a medical device has been provided to the tibia bone.

FIG. 22*b* shows the knee joint in a lateral view when a medical device comprising an artificial contacting surface 1102 has been provided to the proximal part of the tibia bone 104, which together with the fibula bone 103 makes up the lower part of the leg. The artificial knee joint surface comprises a plurality of channels 1105 which are in fluid connection with a conduit 1106 adapted to transport lubricating fluid from a reservoir 1108. The reservoir 1108 is according to the embodiment of FIG. 22*b* placed at the rear side of the tibia bone 104 and fixated to the tibia bone 104 and comprises an injection port 1107 for injecting a lubricating fluid into the reservoir 1108 and/or pressurizing a lubricating fluid contained in the reservoir 1108. The conduit 1106 transports lubricating fluid to the inlet 1123 for further distribution to the channels 1105.

Figure 23:
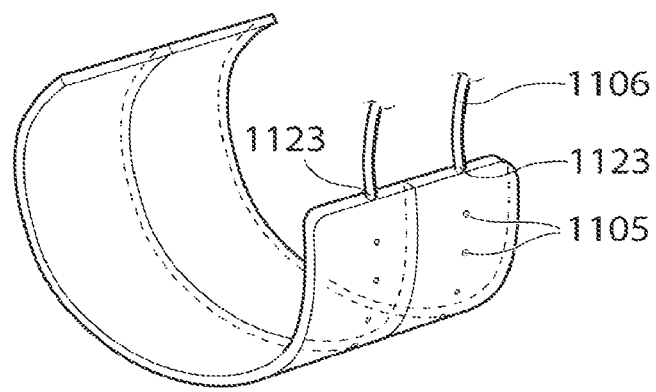
FIG. 23 shows a medical device comprising an artificial knee joint surface.

FIG. 23 shows the medical device for implantation in a knee joint in further detail. The medical device comprises a plurality of channels 1105 placed along the artificial contacting surface of the medical device, for lubricating the contacting surface of the medical device. The channels 1105 are connected to a conduit 1106 for transport of the lubricating fluid along the artificial contacting surface 1101 of the medical device. The conduit 1106 transports lubricating fluid to the inlets 1123 for further distribution to the channels 1105.

Figure 24:
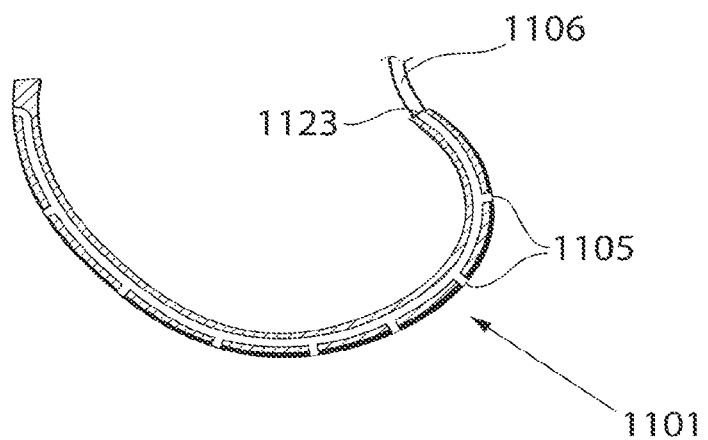
FIG. 24 shows a medical device comprising an artificial knee joint surface in section.

FIG. 24 shows a sectional side-view of the medical device displaying the channels 1105 being fully integrated in the artificial contacting surface and connected to each other, the conduit 1106 supplies the 1105 channels with lubricating fluid for lubricating the artificial contacting surface of the medical device. The conduit 1106 transports lubricating fluid to the inlet 1123 for further distribution to the channels 1105.

Figure 25A:
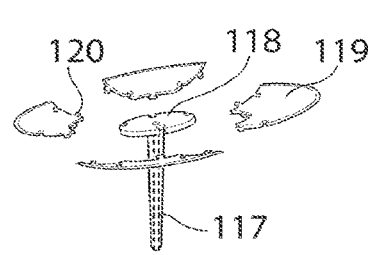
FIG. 25a shows a medical device comprising multiple medical device parts.

FIG. 25a shows a medical device for implantation in a knee joint of a human patient, the medical device comprises a several medical device parts 119 adapted to be connected to each other and to a medical device base part 118 by means of mechanical fixation elements 120 supplying a form fitting between the plurality of medical device parts 119 and the base part 118. The medical device base part 118 furthermore comprises a fixation portion 117 which is adapted to supply mechanical fixation of the medical device to a human bone, such as the proximal part of the tibia bone. The medical device base part 118 furthermore comprises a channel for supplying a lubricating fluid to the artificial contacting surface of the knee joint.

Figure 25B:
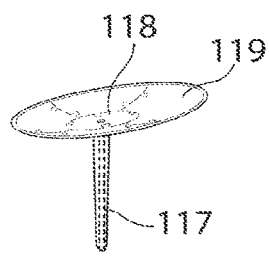
FIG. 25b shows a medical device comprising multiple medical device parts, when assembled.

FIG. 25b shows the medical device according to FIG. 25a, when assembled.

Figure 26:
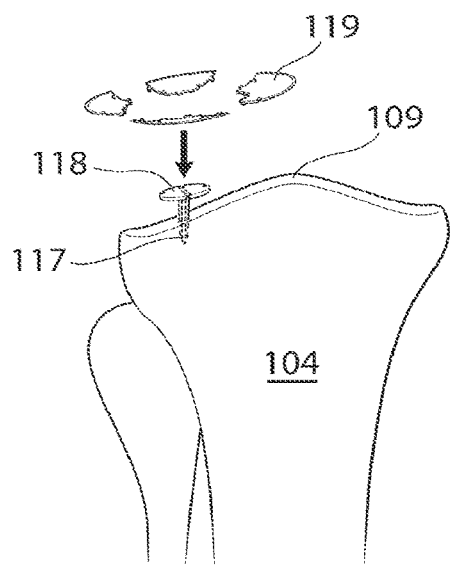
FIG. 26 shows the placing of a medical device comprising multiple medical device parts, when being fixated to the tibia bone.

FIG. 26 shows the medical device according to FIGS. 25a and 25b when the medical device is being fixated to the tibia bone 104.

Figure 27:
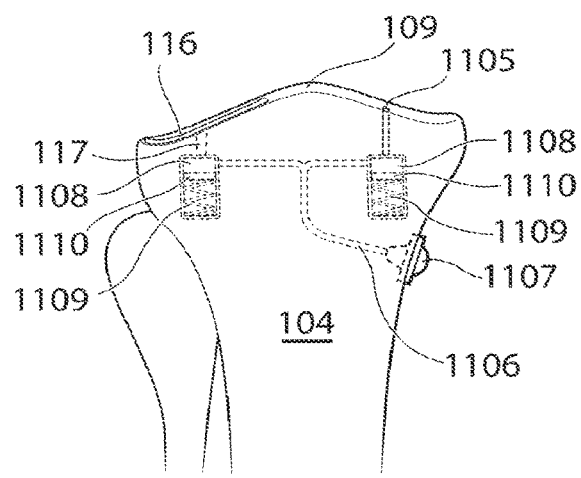
FIG. 27 shows the implantable medical device according to an embodiment, when fixated to the tibia bone and connected to a reservoir and an injection port.

FIG. 27 shows the proximal part of the tibia bone when a medical device comprising an artificial contacting surface 116 has been fixated to the tibia bone 104. The channel 1105 of the artificial contacting surface is connected to a conduit 1106 which supplies a fluid connection between the channel 1105 of the medical device and a first and second reservoir 1108 placed inside of the tibia bone 1104 on the medial and lateral side. The conduit further connects the first and second reservoir to an injection port 1107 placed on the medial side of the pelvic bone for refilling and/or pressurizing the reservoirs 1108. The reservoirs 1108, according to the embodiment shown in FIG. 27 are adapted to place the lubricating fluid under pressure, thereby pressing the lubricating fluid out of the channels 1105 onto the artificial contacting surface, for lubricating the knee joint. For this purpose, the reservoir 1108 comprises a spring 1109 which is in connection with a movable wall portion in the form of a piston 1110, for pressing the lubricating fluid.

Figure 28:
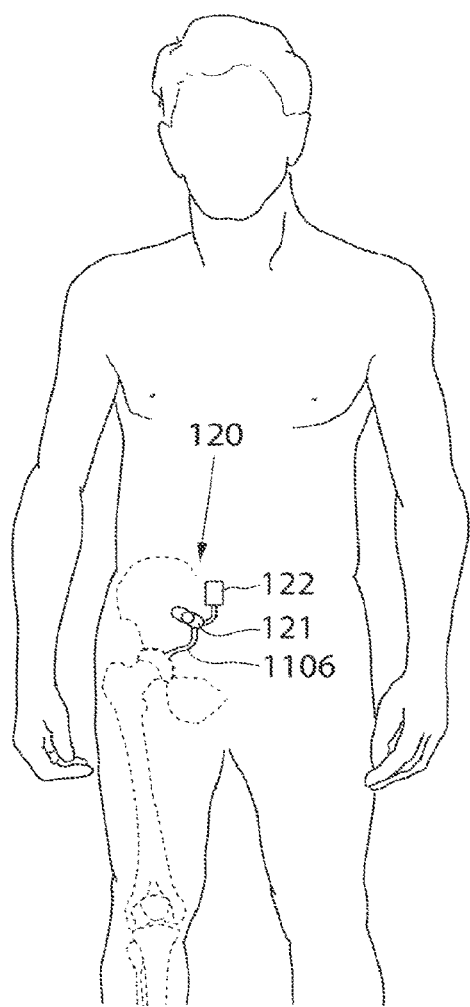
FIG. 28 shows a frontal view of a human patient when an implantable lubricating system has been provided.

FIG. 28 shows the human patient in a frontal view when an implantable lubrication system 120 has been implanted. The implantable lubrication system 120 is adapted to inject a lubricating fluid continuously, intermittently or when needed into said hip joint. According to the embodiment shown in FIG. 61 the implantable lubrication system comprises two interconnected units 121, 122. The two interconnected units are placed in the abdominal region of the human patient and is in connection with the hip joint through a conduit 1106.

Figure 29:
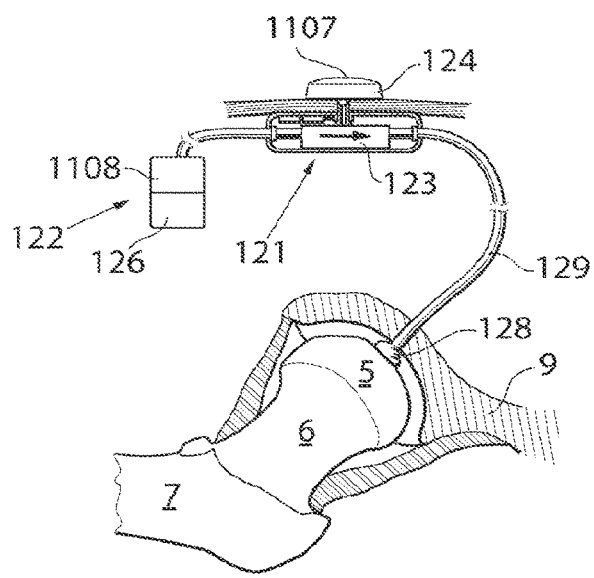
FIG. 29 shows an implantable lubrication system in further detail.

FIG. 29 shows the implantable lubricating system 120, which could be used in combination with any of the medical devices described herein, in further detail. According to the embodiment shown, the implantable lubricating system comprises a first unit 121 comprising a pumping member 123 adapted to pump the lubricating fluid from a reservoir 1108 to an area of the hip joint. The first unit 121 furthermore comprises an injection port 1107 for filling the reservoir 1108 from outside of the human body without having to perform a surgical procedure. The injection port 1107 comprises a self-sealing membrane which is penetratable with a needle attached to a syringe. The first unit 121 further comprises a receiver of wireless energy 124 preferably comprising a coil. Said receiver of wireless energy is used to charge a battery 126. According to this embodiment the implantable lubrication system 120 further comprises a second unit 122 which in turn comprises a battery 126 and a fluid reservoir 1108. The lubricating fluid 128 is pumped from the reservoir 1108, through the first unit 121 with the pumping device, through the conduit 1106 and into the area of the hip joint where it helps lubricating the hip joint surfaces or the artificial contacting surfaces of the implantable medical device. The lubricating fluid is preferably a biocompatible lubricating fluid such as hyaluronic acid.

Figure 30:
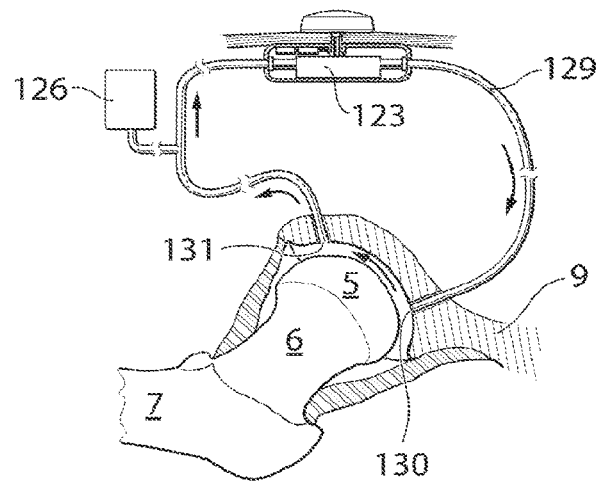
FIG. 30 shows an implantable circling lubrication system in further detail.

FIG. 30 shows the implantable lubricating system adapted to be used with any of the medical device herein, according to an embodiment wherein the implantable lubricating system is a circulating lubricating system comprising one inlet 130 into the joint to be lubricated and one outlet 131. Preferably this system is a system for continuous lubrication where the pumping member 123 continuously circulates the lubricating fluid 128 inside of the hip joint.

Figure 31:
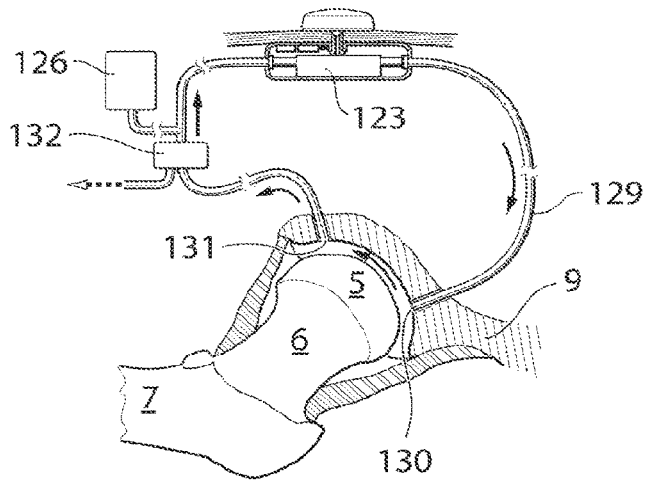
FIG. 31 shows an implantable circling lubrication system comprising a filter, in further detail.

FIG. 31 shows an implantable lubricating system for circulating lubrication adapted to be used with any of the medical device herein, wherein the lubricating system further comprises a filtering member 132 for filtering the lubricating fluid. The filter is adapted to be self cleaning and the out filtered matter is disposed through the disposal channel 133, either into the abdomen of the human patient, or into a container attached to the disposal channel 133. Through the filtering of the lubricating fluid 128 the circulating lubricating system can operate for long periods without the need of any surgical procedures.

Figure 32:
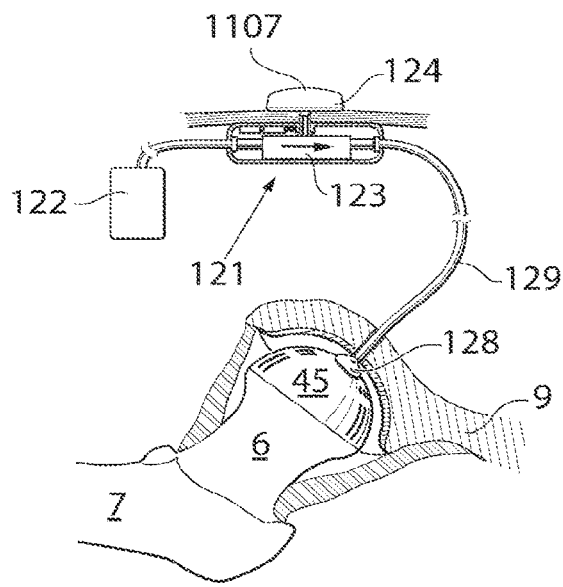
FIG. 32 shows an implantable lubrication system, when lubricating an artificial hip joint surface.

FIG. 32 shows the lubricating fluid of FIG. 29, when lubricating an implantable medical device comprising an artificial contacting surface 45 by providing a lubricating fluid 128.

Figure 33A:
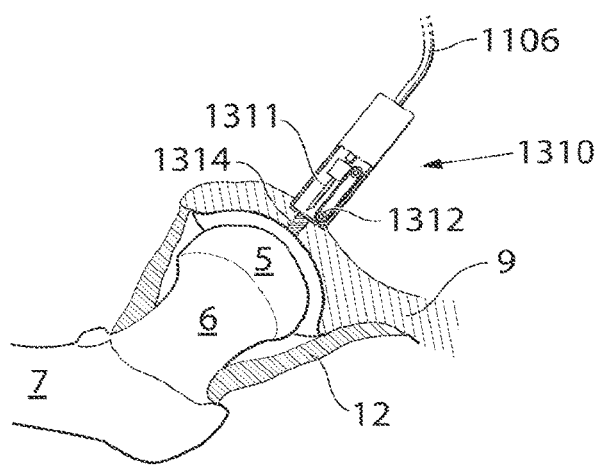
FIG. 33a shows an implantable lubrication system comprising a retractable needle, in a first state.

FIG. 33a shows a lubricating system, which could be adapted to be used in combination with any of the medical devices herein, according to another embodiment wherein the lubricating system comprises a unit 1310 comprising a retractable needle 1311 fixated to an operating system for operating said retractable needle 1311. The needle is adapted to penetrate a self sealing membrane 1314 placed in the pelvic bone 9 for injecting a lubricating fluid into the hip joint. A conduit 1106 is adapted to supply the unit 1310 with a lubricating fluid from an injection port and/or from an additional reservoir which could be implanted subcutaneously or in a cavity of the body.

Figure 33B:
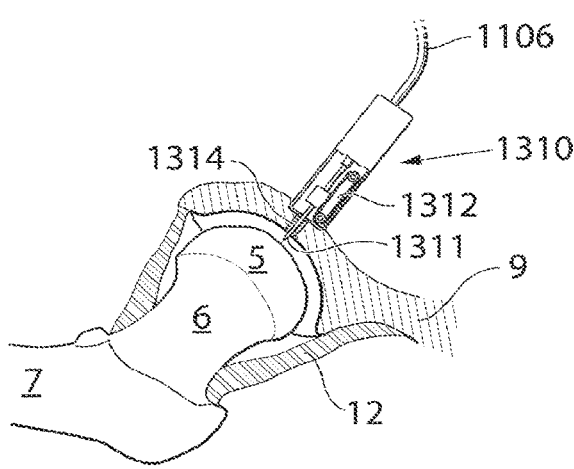
FIG. 33b shows an implantable lubrication system comprising a retractable needle, in a second state.

FIG. 33b shows the lubricating system in a state in which the retractable needle 1311 is in its advanced position by the operating device having operated the retractable needle 1311. The needle thereby penetrates the self sealing membrane 1314 and is placed in a position in which injection of a lubricating fluid is possible.

FIG. 34 illustrates a system for treating a disease comprising an apparatus 10 of the present invention placed in the abdomen of a patient. An implanted energy-transforming device 1002 is adapted to supply energy consuming components of the apparatus with energy via a power supply line 1003. An external energy-transmission device 1004 for non-invasively energizing the apparatus 10 transmits energy by at least one wireless energy signal. The implanted energy-transforming device 1002 transforms energy from the wireless energy signal into electric energy which is supplied via the power supply line 1003.

The implanted energy-transforming device 1002 may also comprise other components, such as: a coil for reception and/or transmission of signals and energy, an antenna for reception and/or transmission of signals, a microcontroller, a charge control unit, optionally comprising an energy storage, such as a capacitor, one or more sensors, such as temperature sensor, pressure sensor, position sensor, motion sensor etc., a transceiver, a motor, optionally including a motor controller, a pump, and other parts for controlling the operation of a medical implant.

The wireless energy signal may include a wave signal selected from the following: a sound wave signal, an ultrasound wave signal, an electromagnetic wave signal, an infrared light signal, a visible light signal, an ultra violet light signal, a laser light signal, a micro wave signal, a radio wave signal, an x-ray radiation signal and a gamma radiation signal. Alternatively, the wireless energy signal may include an electric or magnetic field, or a combined electric and magnetic field.

The wireless energy-transmission device 1004 may transmit a carrier signal for carrying the wireless energy signal. Such a carrier signal may include digital, analogue or a combination of digital and analogue signals. In this case, the wireless energy signal includes an analogue or a digital signal, or a combination of an analogue and digital signal.

Generally speaking, the energy-transforming device 1002 is provided for transforming wireless energy of a first form transmitted by the energy-transmission device 1004 into energy of a second form, which typically is different from the energy of the first form. The implanted apparatus 10 is operable in response to the energy of the second form. The energy-transforming device 1002 may directly power the apparatus with the second form energy, as the energy-transforming device 1002 transforms the first form energy transmitted by the energy-transmission device 1004 into the second form energy. The system may further include an implantable accumulator, wherein the second form energy is used at least partly to charge the accumulator.

Alternatively, the wireless energy transmitted by the energy-transmission device 1004 may be used to directly power the apparatus, as the wireless energy is being transmitted by the energy-transmission device 1004. Where the system comprises an operation device for operating the apparatus, as will be described below, the wireless energy transmitted by the energy-transmission device 1004 may be used to directly power the operation device to create kinetic energy for the operation of the apparatus.

The wireless energy of the first form may comprise sound waves and the energy-transforming device 1002 may include a piezo-electric element for transforming the sound waves into electric energy. The energy of the second form may comprise electric energy in the form of a direct current or pulsating direct current, or a combination of a direct current and pulsating direct current, or an alternating current or a combination of a direct and alternating current. Normally, the apparatus comprises electric components that are energized with electrical energy. Other implantable electric components of the system may be at least one voltage level guard or at least one constant current guard connected with the electric components of the apparatus.

Optionally, one of the energy of the first form and the energy of the second form may comprise magnetic energy, kinetic energy, sound energy, chemical energy, radiant energy, electromagnetic energy, photo energy, nuclear energy or thermal energy. Preferably, one of the energy of the first form and the energy of the second form is non-magnetic, non-kinetic, non-chemical, non-sonic, non-nuclear or non-thermal.

The energy-transmission device may be controlled from outside the patient's body to release electromagnetic wireless energy, and the released electromagnetic wireless energy is used for operating the apparatus. Alternatively, the energy-transmission device is controlled from outside the patient's body to release non-magnetic wireless energy, and the released non-magnetic wireless energy is used for operating the apparatus.

The external energy-transmission device 1004 also includes a wireless remote control having an external signal transmitter for transmitting a wireless control signal for non-invasively controlling the apparatus. The control signal is received by an implanted signal receiver which may be incorporated in the implanted energy-transforming device 1002 or be separate there from.

The wireless control signal may include a frequency, amplitude, or phase modulated signal or a combination thereof. Alternatively, the wireless control signal includes an analogue or a digital signal, or a combination of an analogue and digital signal. Alternatively, the wireless control signal comprises an electric or magnetic field, or a combined electric and magnetic field.

The wireless remote control may transmit a carrier signal for carrying the wireless control signal. Such a carrier signal may include digital, analogue or a combination of digital and analogue signals. Where the control signal includes an analogue or a digital signal, or a combination of an analogue and digital signal, the wireless remote control preferably transmits an electromagnetic carrier wave signal for carrying the digital or analogue control signals.

FIG. 35 illustrates the system of FIG. 34 in the form of a more generalized block diagram showing the apparatus 10, the energy-transforming device 1002 powering the apparatus 10 via power supply line 1003, and the external energy-transmission device 1004, The patient's skin 1005, generally shown by a vertical line, separates the interior of the patient to the right of the line from the exterior to the left of the line.

FIG. 36 shows an embodiment of the invention identical to that of FIG. 35, except that a reversing device in the form of an electric switch 1006 operable for example by polarized energy also is implanted in the patient for reversing the apparatus 10. When the switch is operated by polarized energy the wireless remote control of the external energy-transmission device 1004 transmits a wireless signal that carries polarized energy and the implanted energy-transforming device 1002 transforms the wireless polarized energy into a polarized current for operating the electric switch 1006. When the polarity of the current is shifted by the implanted energy-transforming device 1002 the electric switch 1006 reverses the function performed by the apparatus 10.

FIG. 37 shows an embodiment of the invention identical to that of FIG. 35, except that an operation device 1007 implanted in the patient for operating the apparatus 10 is provided between the implanted energy-transforming device 1002 and the apparatus 10. This operation device can be in the form of a motor 1007, such as an electric servomotor. The motor 1007 is powered with energy from the implanted energy-transforming device 1002, as the remote control of the external energy-transmission device 1004 transmits a wireless signal to the receiver of the implanted energy-transforming device 1002.

FIG. 38 shows an embodiment of the invention identical to that of FIG. 35, except that it also comprises an operation device in the form of an assembly 1008 including a motor/pump unit 1009 and a fluid reservoir 1010 is implanted in the patient. In this case the apparatus 10 is hydraulically operated, i.e. hydraulic fluid is pumped by the motor/pump unit 1009 from the fluid reservoir 1010 through a conduit 1011 to the apparatus 10 to operate the apparatus, and hydraulic fluid is pumped by the motor/pump unit 1009 back from the apparatus 10 to the fluid reservoir 1010 to return the apparatus to a starting position. The implanted energy-transforming device 1002 transforms wireless energy into a current, for example a polarized current, for powering the motor/pump unit 1009 via an electric power supply line 1012.

Instead of a hydraulically operated apparatus 10, it is also envisaged that the operation device comprises a pneumatic operation device. In this case, the hydraulic fluid can be pressurized air to be used for regulation and the fluid reservoir is replaced by an air chamber.

In all of these embodiments the energy-transforming device 1002 may include a rechargeable accumulator like a battery or a capacitor to be charged by the wireless energy and supplies energy for any energy consuming part of the system.

As an alternative, the wireless remote control described above may be replaced by manual control of any implanted part to make contact with by the patient's hand most likely indirect, for example a press button placed under the skin.

Figure 39:
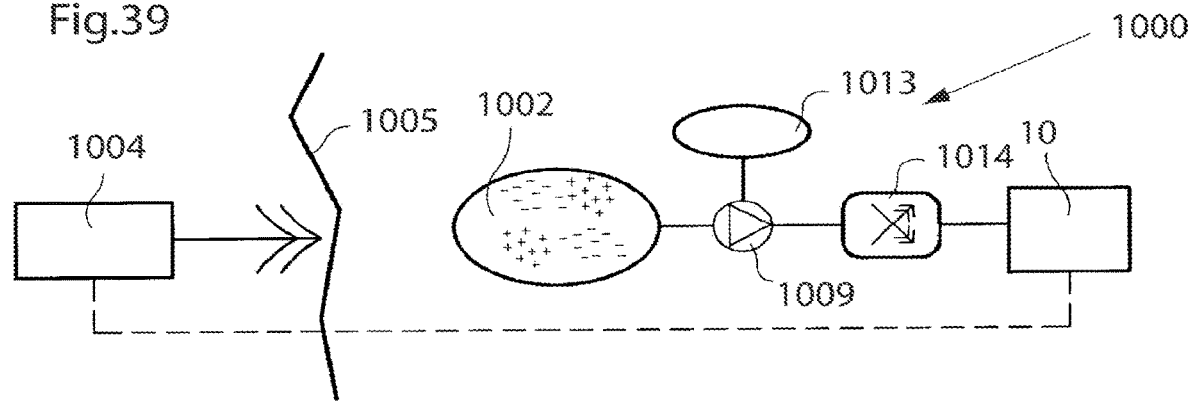

FIG. 39 shows an embodiment of the invention comprising the external energy-transmission device 1004 with its wireless remote control, the apparatus 10, in this case hydraulically operated, and the implanted energy-transforming device 1002, and further comprising a hydraulic fluid reservoir 1013, a motor/pump unit 1009 and an reversing device in the form of a hydraulic valve shifting device 1014, all implanted in the patient. Of course the hydraulic operation could easily be performed by just changing the pumping direction and the hydraulic valve may therefore be omitted. The remote control may be a device separated from the external energy-transmission device or included in the same. The motor of the motor/pump unit 1009 is an electric motor. In response to a control signal from the wireless remote control of the external energy-transmission device 1004, the implanted energy-transforming device 1002 powers the motor/pump unit 1009 with energy from the energy carried by the control signal, whereby the motor/pump unit 1009 distributes hydraulic fluid between the hydraulic fluid reservoir 1013 and the apparatus 10. The remote control of the external energy-transmission device 1004 controls the hydraulic valve shifting device 1014 to shift the hydraulic fluid flow direction between one direction in which the fluid is pumped by the motor/pump unit 1009 from the hydraulic fluid reservoir 1013 to the apparatus 10 to operate the apparatus, and another opposite direction in which the fluid is pumped by the motor/pump unit 1009 back from the apparatus 10 to the hydraulic fluid reservoir 1013 to return the apparatus to a starting position.

Figure 40:
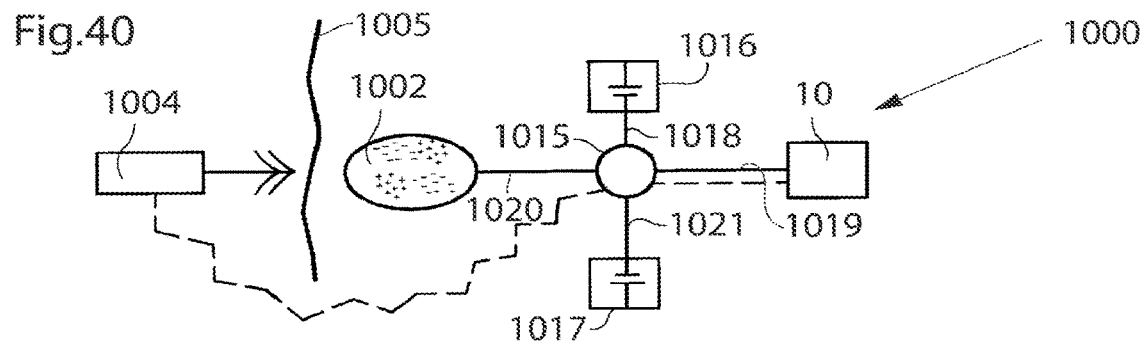

FIG. 40 shows an embodiment of the invention comprising the external energy-transmission device 1004 with its wireless remote control, the apparatus 10, the implanted energy-transforming device 1002, an implanted internal control unit 1015 controlled by the wireless remote control of the external energy-transmission device 1004, an implanted accumulator 1016 and an implanted capacitor 1017. The internal control unit 1015 arranges storage of electric energy received from the implanted energy-transforming device 1002 in the accumulator 1016, which supplies energy to the apparatus 10. In response to a control signal from the wireless remote control of the external energy-transmission device 1004, the internal control unit 1015 either releases electric energy from the accumulator 1016 and transfers the released energy via power lines 1018 and 1019, or directly transfers electric energy from the implanted energy-transforming device 1002 via a power line 1020, the capacitor 1017, which stabilizes the electric current, a power line 1021 and the power line 1019, for the operation of the apparatus 10.

The internal control unit is preferably programmable from outside the patient's body. In a preferred embodiment, the internal control unit is programmed to regulate the apparatus 10 according to a pre-programmed time-schedule or to input from any sensor sensing any possible physical parameter of the patient or any functional parameter of the system.

In accordance with an alternative, the capacitor 1017 in the embodiment of FIG. 40, 10 may be omitted. In accordance with another alternative, the accumulator 1016 in this embodiment may be omitted.

Figure 41:
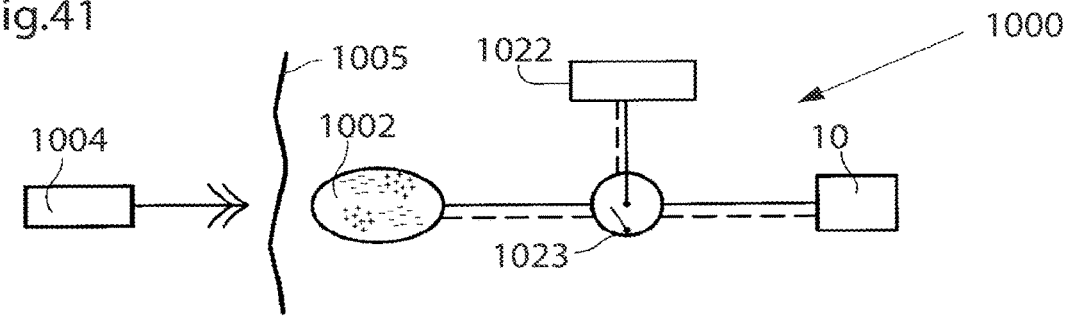

FIG. 41 shows an embodiment of the invention identical to that of FIG. 35, except that a battery 1022 for supplying energy for the operation of the apparatus 10 and an electric switch 1023 for switching the operation of the apparatus 10 also are implanted in the patient. The electric switch 1023 may be controlled by the remote control and may also be operated by the energy supplied by the implanted energy-transforming device 1002 to switch from an off mode, in which the battery 1022 is not in use, to an on mode, in which the battery 1022 supplies energy for the operation of the apparatus 10.

Figure 42:
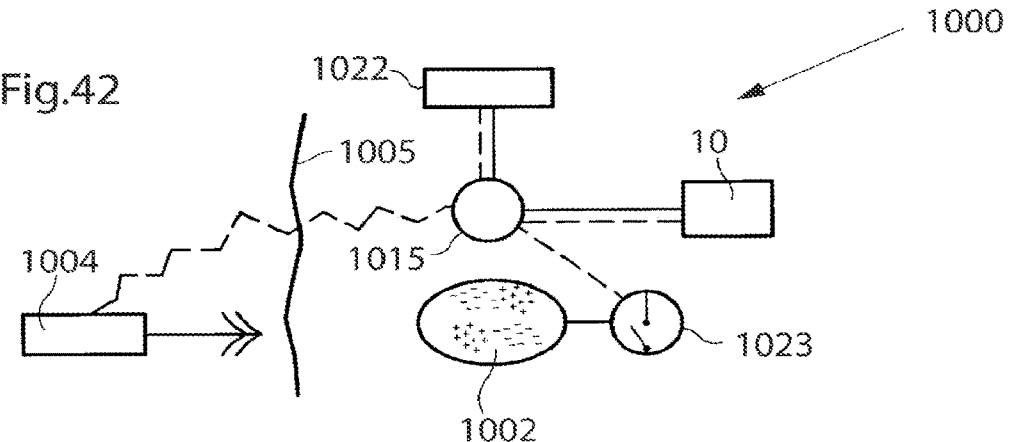

FIG. 42 shows an embodiment of the invention identical to that of FIG. 41, except that an internal control unit 1015 controllable by the wireless remote control of the external energy-transmission device 1004 also is implanted in the patient. In this case, the electric switch 1023 is operated by the energy supplied by the implanted energy-transforming device 1002 to switch from an off mode, in which the wireless remote control is prevented from controlling the internal control unit 1015 and the battery is not in use, to a standby mode, in which the remote control is permitted to control the internal control unit 1015 to release electric energy from the battery 1022 for the operation of the apparatus 10.

Figure 43:
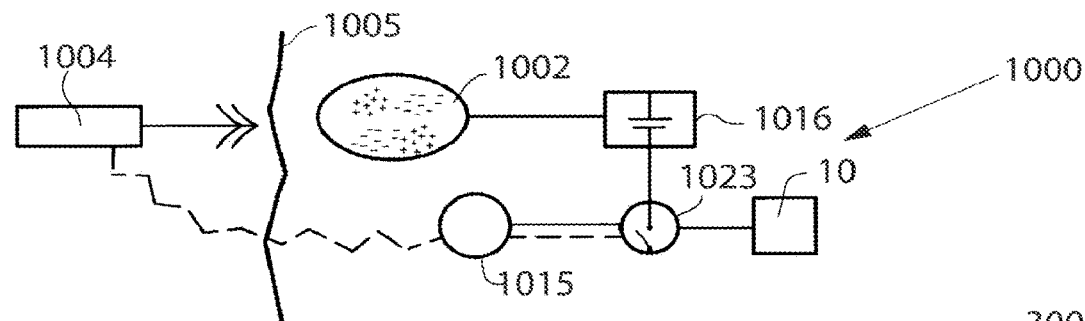

FIG. 43 shows an embodiment of the invention identical to that of FIG. 42, except that an accumulator 1016 is substituted for the battery 1022 and the implanted components are interconnected differently. In this case, the accumulator 1016 stores energy from the implanted energy-transforming device 1002. In response to a control signal from the wireless remote control of the external energy-transmission device 1004, the internal control unit 1015 controls the electric switch 1023 to switch from an off mode, in which the accumulator 1016 is not in use, to an on mode, in which the accumulator 1016 supplies energy for the operation of the apparatus 10. The accumulator may be combined with or replaced by a capacitor.

Figure 44:
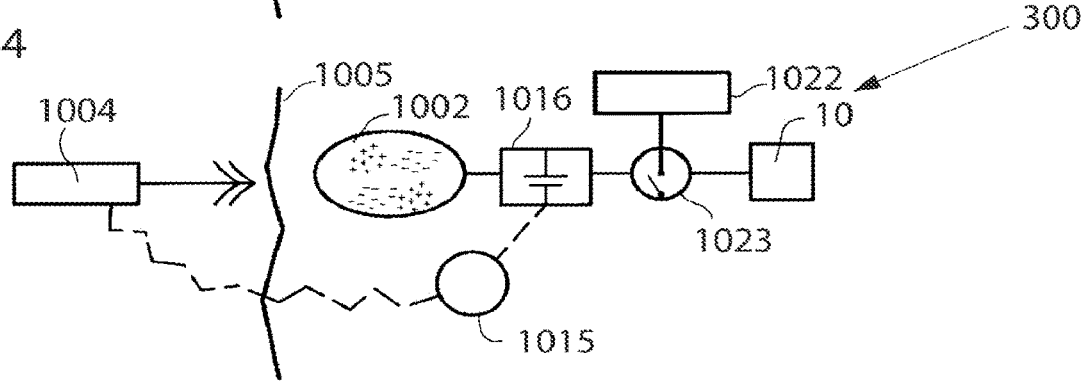

FIG. 44 shows an embodiment of the invention identical to that of FIG. 43, except that a battery 1022 also is implanted in the patient and the implanted components are interconnected differently. In response to a control signal from the wireless remote control of the external energy-transmission device 1004, the internal control unit 1015 controls the accumulator 1016 to deliver energy for operating the electric switch 1023 to switch from an off mode, in which the battery 1022 is not in use, to an on mode, in which the battery 1022 supplies electric energy for the operation of the apparatus 10.

Alternatively, the electric switch 1023 may be operated by energy supplied by the accumulator 1016 to switch from an off mode, in which the wireless remote control is prevented from controlling the battery 1022 to supply electric energy and is not in use, to a standby mode, in which the wireless remote control is permitted to control the battery 1022 to supply electric energy for the operation of the apparatus 10.

It should be understood that the switch 1023 and all other switches in this application should be interpreted in its broadest embodiment. This means a transistor, MCU, MCPU, ASIC, FPGA or a DA converter or any other electronic component or circuit that may switch the power on and off. Preferably the switch is controlled from outside the body, or alternatively by an implanted internal control unit.

Figure 45:
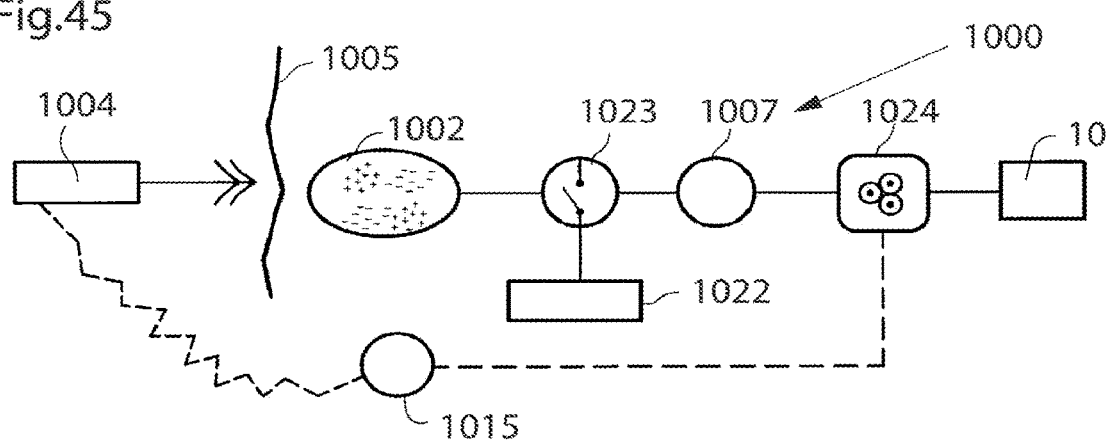

FIG. 45 shows an embodiment of the invention identical to that of FIG. 41, except that a motor 1007, a mechanical reversing device in the form of a gear box 1024, and an internal control unit 1015 for controlling the gear box 1024 also are implanted in the patient. The internal control unit 1015 controls the gear box 1024 to reverse the function performed by the apparatus 10 (mechanically operated). Even simpler is to switch the direction of the motor electronically. The gear box interpreted in its broadest embodiment may stand for a servo arrangement saving force for the operation device in favor of longer stroke to act.

Figure 46:
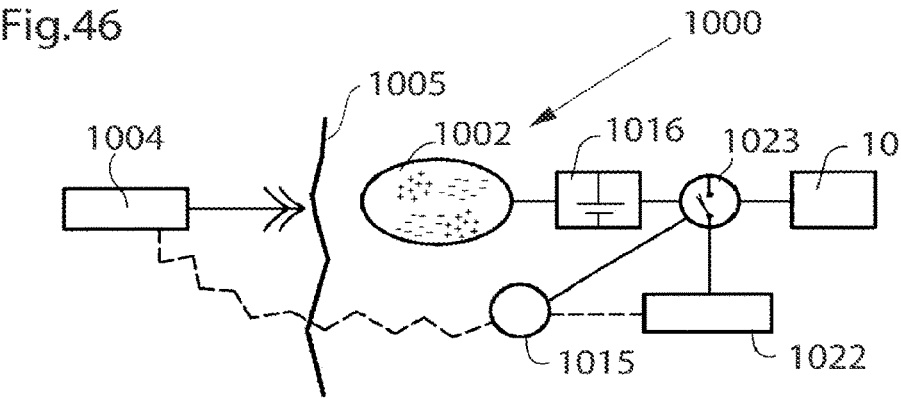
Figure 52:
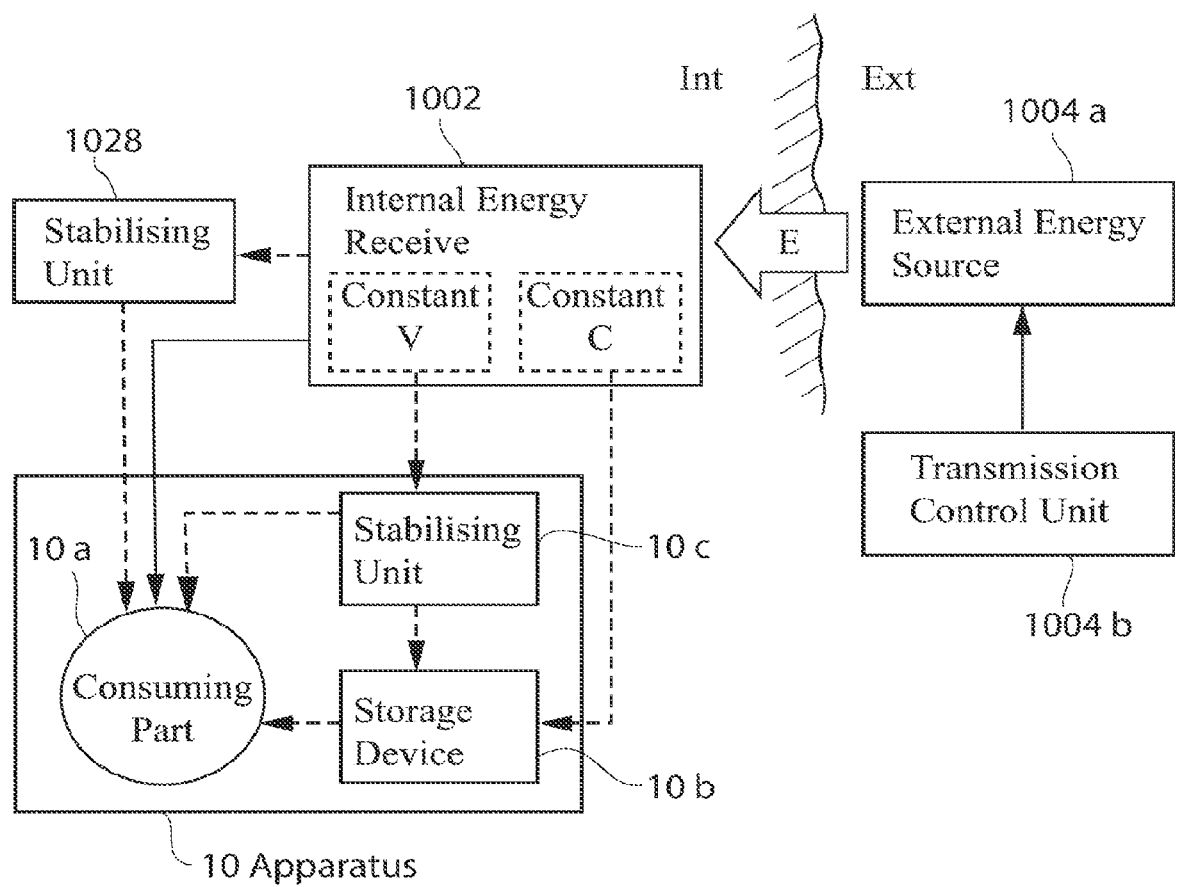
FIG. 52 is a more detailed block diagram of an arrangement for controlling the transmission of wireless energy used for the operation of the apparatus shown in FIG. 34.

FIG. 46 shows an embodiment of the invention identical to that of FIG. 52 except that the implanted components are interconnected differently. Thus, in this case the internal control unit 1015 is powered by the battery 1022 when the accumulator 1016, suitably a capacitor, activates the electric switch 1023 to switch to an on mode. When the electric switch 1023 is in its on mode the internal control unit 1015 is permitted to control the battery 1022 to supply, or not supply, energy for the operation of the apparatus 10.

Figure 47:
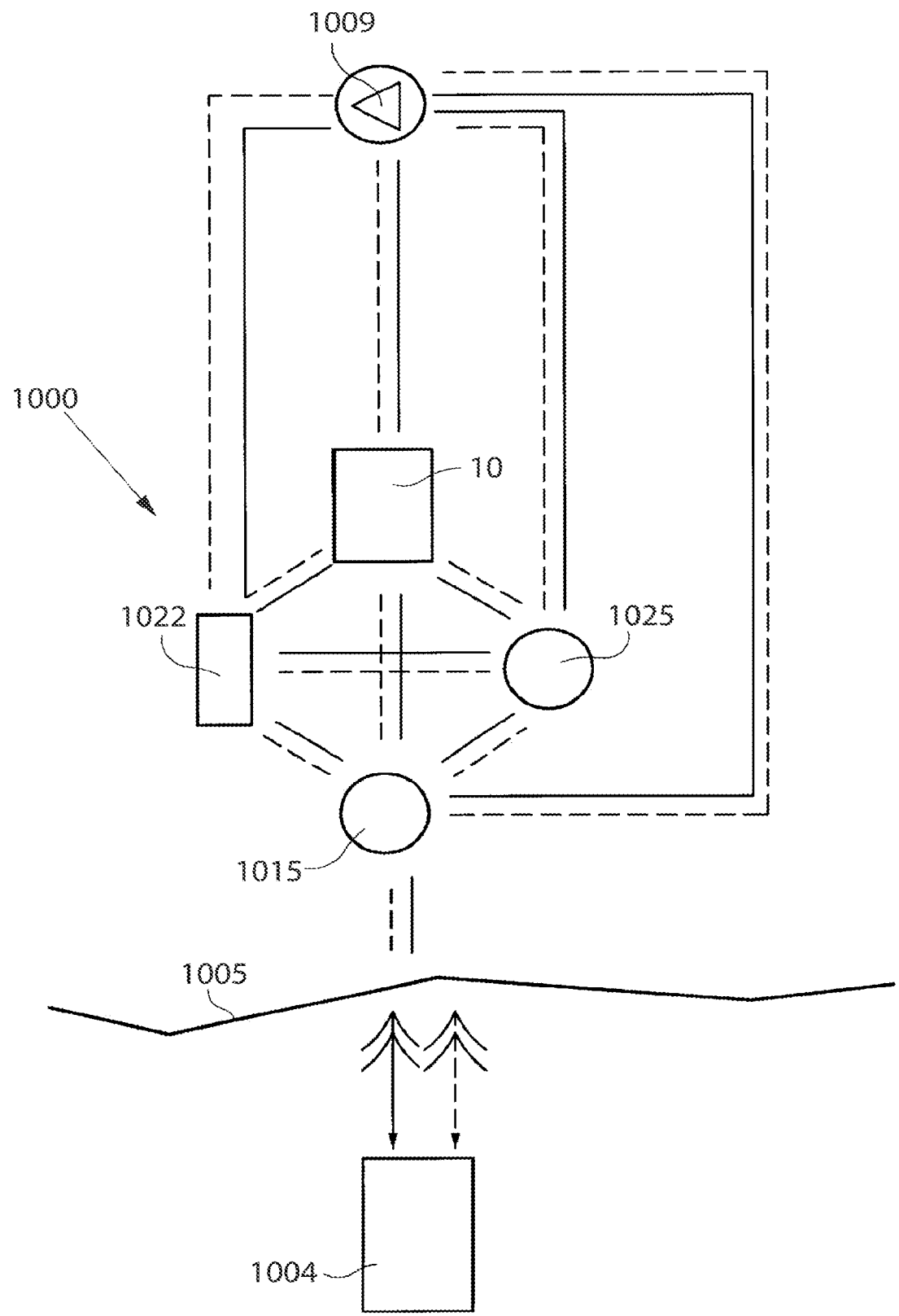

FIG. 47 schematically shows conceivable combinations of implanted components of the apparatus for achieving various communication options. Basically, there are the apparatus 10, the internal control unit 1015, motor or pump unit 1009, and the external energy-transmission device 1004 including the external wireless remote control. As already described above the wireless remote control transmits a control signal which is received by the internal control unit 1015, which in turn controls the various implanted components of the apparatus.

A feedback device, preferably comprising a sensor or measuring device 1025, may be implanted in the patient for sensing a physical parameter of the patient. The physical parameter may be at least one selected from the group consisting of pressure, volume, diameter, stretching, elongation, extension, movement, bending, elasticity, muscle contraction, nerve impulse, body temperature, blood pressure, blood flow, heartbeats and breathing. The sensor may sense any of the above physical parameters. For example, the sensor may be a pressure or motility sensor. Alternatively, the sensor 1025 may be arranged to sense a functional parameter. The functional parameter may be correlated to the transfer of energy for charging an implanted energy source and may further include at least one selected from the group of parameters consisting of; electricity, any electrical parameter, pressure, volume, diameter, stretch, elongation, extension, movement, bending, elasticity, temperature and flow.

The feedback may be sent to the internal control unit or out to an external control unit preferably via the internal control unit. Feedback may be sent out from the body via the energy transfer system or a separate communication system with receiver and transmitters.

The internal control unit 1015, or alternatively the external wireless remote control of the external energy-transmission device 1004, may control the apparatus 10 in response to signals from the sensor 1025. A transceiver may be combined with the sensor 1025 for sending information on the sensed physical parameter to the external wireless remote control. The wireless remote control may comprise a signal transmitter or transceiver and the internal control unit 1015 may comprise a signal receiver or transceiver. Alternatively, the wireless remote control may comprise a signal receiver or transceiver and the internal control unit 1015 may comprise a signal transmitter or transceiver. The above transceivers, transmitters and receivers may be used for sending information or data related to the apparatus 10 from inside the patient's body to the outside thereof.

Where the motor/pump unit 1009 and battery 1022 for powering the motor/pump unit 1009 are implanted, information related to the charging of the battery 1022 may be fed back. To be more precise, when charging a battery or accumulator with energy feed back information related to said charging process is sent and the energy supply is changed accordingly.

FIG. 48 shows an alternative embodiment wherein the apparatus 10 is regulated from outside the patient's body. The system 1000 comprises a battery 1022 connected to the apparatus 10 via a subcutaneous electric switch 1026. Thus, the regulation of the apparatus 10 is performed non-invasively by manually pressing the subcutaneous switch, whereby the operation of the apparatus 10 is switched on and off. It will be appreciated that the shown embodiment is a simplification and that additional components, such as an internal control unit or any other part disclosed in the present application can be added to the system. Two subcutaneous switches may also be used. In the preferred embodiment one implanted switch sends information to the internal control unit to perform a certain pre-determined performance and when the patient press the switch again the performance is reversed.

FIG. 49 shows an alternative embodiment, wherein the system 1000 comprises a hydraulic fluid reservoir 1013 hydraulically connected to the apparatus. Non-invasive regulation is performed by manually pressing the hydraulic reservoir connected to the apparatus. Alternatively, the hydraulic fluid reservoir 1013 is adapted to work with an injection port for the injection of hydraulic fluid, preferably for calibration of hydraulic fluid.

The system may include an external data communicator and an implantable internal data communicator communicating with the external data communicator. The internal communicator feeds data related to the apparatus or the patient to the external data communicator and/or the external data communicator feeds data to the internal data communicator.

FIG. 50 schematically illustrates an arrangement of the system that is capable of sending information from inside the patient's body to the outside thereof to give feedback information related to at least one functional parameter of the apparatus or system, or related to a physical parameter of the patient, in order to supply an accurate amount of energy to an implanted internal energy receiver 1002 connected to implanted energy consuming components of the apparatus 10. Such an energy receiver 1002 may include an energy source and/or an energy-transforming device. Briefly described, wireless energy is transmitted from an external energy source 1004a located outside the patient and is received by the internal energy receiver 1002 located inside the patient. The internal energy receiver is adapted to directly or indirectly supply received energy to the energy consuming components of the apparatus 10 via a switch 1026. An energy balance is determined between the energy received by the internal energy receiver 1002 and the energy used for the apparatus 10, and the transmission of wireless energy is then controlled based on the determined energy balance. The energy balance thus provides an accurate indication of the correct amount of energy needed, which is sufficient to operate the apparatus 10 properly, but without causing undue temperature rise.

In FIG. 50 the patient's skin is indicated by a vertical line 1005. Here, the energy receiver comprises an energy-transforming device 1002 located inside the patient, preferably just beneath the patient's skin 1005. Generally speaking, the implanted energy-transforming device 1002 may be placed in the abdomen, thorax, muscle fascia (e.g. in the abdominal wall), subcutaneously, or at any other suitable location. The implanted energy-transforming device 1002 is adapted to receive wireless energy E transmitted from the external energy-source 1004*a* provided in an external energy-transmission device 1004 located outside the patient's skin 1005 in the vicinity of the implanted energy-transforming device 1002.

As is well known in the art, the wireless energy E may generally be transferred by means of any suitable Transcutaneous Energy Transfer (TET) device, such as a device including a primary coil arranged in the external energy source 1004*a* and an adjacent secondary coil arranged in the implanted energy-transforming device 1002. When an electric current is fed through the primary coil, energy in the form of a voltage is induced in the secondary coil which can be used to power the implanted energy consuming components of the apparatus, e.g. after storing the incoming energy in an implanted energy source, such as a rechargeable battery or a capacitor. However, the present invention is generally not limited to any particular energy transfer technique, TET devices or energy sources, and any kind of wireless energy may be used.

The amount of energy received by the implanted energy receiver may be compared with the energy used by the implanted components of the apparatus. The term "energy used" is then understood to include also energy stored by implanted components of the apparatus. A control device includes an external control unit 1004*b* that controls the external energy source 1004*a* based on the determined energy balance to regulate the amount of transferred energy. In order to transfer the correct amount of energy, the energy balance and the required amount of energy is determined by means of a determination device including an implanted internal control unit 1015 connected between the switch 1026 and the apparatus 10. The internal control unit 1015 may thus be arranged to receive various measurements obtained by suitable sensors or the like, not shown, measuring certain characteristics of the apparatus 10, somehow reflecting the required amount of energy needed for proper operation of the apparatus 10. Moreover, the current condition of the patient may also be detected by means of suitable measuring devices or sensors, in order to provide parameters reflecting the patient's condition. Hence, such characteristics and/or parameters may be related to the current state of the apparatus 10, such as power consumption, operational mode and temperature, as well as the patient's condition reflected by parameters such as; body temperature, blood pressure, heartbeats and breathing. Other kinds of physical parameters of the patient and functional parameters of the device are described elsewhere.

Furthermore, an energy source in the form of an accumulator 1016 may optionally be connected to the implanted energy-transforming device 1002 via the control unit 1015 for accumulating received energy for later use by the apparatus 10. Alternatively or additionally, characteristics of such an accumulator, also reflecting the required amount of energy, may be measured as well. The accumulator may be replaced by a rechargeable battery, and the measured characteristics may be related to the current state of the battery, any electrical parameter such as energy consumption voltage, temperature, etc. In order to provide sufficient voltage and current to the apparatus 10, and also to avoid excessive heating, it is clearly understood that the battery should be charged optimally by receiving a correct amount of energy from the implanted energy-transforming device 1002, i.e. not too little or too much. The accumulator may also be a capacitor with corresponding characteristics.

For example, battery characteristics may be measured on a regular basis to determine the current state of the battery, which then may be stored as state information in a suitable storage means in the internal control unit 1015. Thus, whenever new measurements are made, the stored battery state information can be updated accordingly. In this way, the state of the battery can be "calibrated" by transferring a correct amount of energy, so as to maintain the battery in an optimal condition.

Thus, the internal control unit 1015 of the determination device is adapted to determine the energy balance and/or the currently required amount of energy, (either energy per time unit or accumulated energy) based on measurements made by the above-mentioned sensors or measuring devices of the apparatus 10, or the patient, or an implanted energy source if used, or any combination thereof. The internal control unit 1015 is further connected to an internal signal transmitter 1027, arranged to transmit a control signal reflecting the determined required amount of energy, to an external signal receiver 1004*c* connected to the external control unit 1004*b*. The amount of energy transmitted from the external energy source 1004*a* may then be regulated in response to the received control signal.

Alternatively, the determination device may include the external control unit 1004*b*. In this alternative, sensor measurements can be transmitted directly to the external control unit 1004*b* wherein the energy balance and/or the currently required amount of energy can be determined by the external control unit 1004*b*, thus integrating the above-described function of the internal control unit 1015 in the external control unit 1004*b*. In that case, the internal control unit 1015 can be omitted and the sensor measurements are supplied directly to the internal signal transmitter 1027 which sends the measurements over to the external signal receiver 1004*c* and the external control unit 1004*b*. The energy balance and the currently required amount of energy can then be determined by the external control unit 1004*b* based on those sensor measurements.

Hence, the present solution according to the arrangement of FIG. 50 employs the feed back of information indicating the required energy, which is more efficient than previous solutions because it is based on the actual use of energy that is compared to the received energy, e.g. with respect to the amount of energy, the energy difference, or the energy receiving rate as compared to the energy rate used by implanted energy consuming components of the apparatus. The apparatus may use the received energy either for consuming or for storing the energy in an implanted energy source or the like. The different parameters discussed above would thus be used if relevant and needed and then as a tool for determining the actual energy balance. However, such parameters may also be needed per se for any actions taken internally to specifically operate the apparatus.

The internal signal transmitter 1027 and the external signal receiver 1004*c* may be implemented as separate units using suitable signal transfer means, such as radio, IR (Infrared) or ultrasonic signals. Alternatively, the internal signal transmitter 1027 and the external signal receiver 1004*c* may be integrated in the implanted energy-transforming device 1002 and the external energy source 1004*a*, respectively, so as to convey control signals in a reverse direction relative to the energy transfer, basically using the same transmission technique. The control signals may be modulated with respect to frequency, phase or amplitude.

Thus, the feedback information may be transferred either by a separate communication system including receivers and transmitters or may be integrated in the energy system. In accordance with the present invention, such an integrated information feedback and energy system comprises an implantable internal energy receiver for receiving wireless energy, the energy receiver having an internal first coil and a first electronic circuit connected to the first coil, and an external energy transmitter for transmitting wireless energy, the energy transmitter having an external second coil and a second electronic circuit connected to the second coil. The external second coil of the energy transmitter transmits wireless energy which is received by the first coil of the energy receiver. This system further comprises a power switch for switching the connection of the internal first coil to the first electronic circuit on and off, such that feedback information related to the charging of the first coil is received by the external energy transmitter in the form of an impedance variation in the load of the external second coil, when the power switch switches the connection of the internal first coil to the first electronic circuit on and off. In implementing this system in the arrangement of FIG. 50, the switch 1026 is either separate and controlled by the internal control unit 1015, or integrated in the internal control unit 1015. It should be understood that the switch 1026 should be interpreted in its broadest embodiment. This means a transistor, MCU, MCPU, ASIC FPGA or a DA converter or any other electronic component or circuit that may switch the power on and off.

To conclude, the energy supply arrangement illustrated in FIG. 50 may operate basically in the following manner. The energy balance is first determined by the internal control unit 1015 of the determination device. A control signal reflecting the required amount of energy is also created by the internal control unit 1015, and the control signal is transmitted from the internal signal transmitter 1027 to the external signal receiver 1004*c*. Alternatively, the energy balance can be determined by the external control unit 1004*b* instead depending on the implementation, as mentioned above. In that case, the control signal may carry measurement results from various sensors. The amount of energy emitted from the external energy source 1004*a* can then be regulated by the external control unit 1004*b*, based on the determined energy balance, e.g. in response to the received control signal. This process may be repeated intermittently at certain intervals during ongoing energy transfer, or may be executed on a more or less continuous basis during the energy transfer.

The amount of transferred energy can generally be regulated by adjusting various transmission parameters in the external energy source 1004*a*, such as voltage, current, amplitude, wave frequency and pulse characteristics.

This system may also be used to obtain information about the coupling factors between the coils in a TET system even to calibrate the system both to find an optimal place for the external coil in relation to the internal coil and to optimize energy transfer. Simply comparing in this case the amount of energy transferred with the amount of energy received. For example if the external coil is moved the coupling factor may vary and correctly displayed movements could cause the external coil to find the optimal place for energy transfer. Preferably, the external coil is adapted to calibrate the amount of transferred energy to achieve the feedback information in the determination device, before the coupling factor is maximized.

This coupling factor information may also be used as a feedback during energy transfer. In such a case, the energy system of the present invention comprises an implantable internal energy receiver for receiving wireless energy, the energy receiver having an internal first coil and a first electronic circuit connected to the first coil, and an external energy transmitter for transmitting wireless energy, the energy transmitter having an external second coil and a second electronic circuit connected to the second coil. The external second coil of the energy transmitter transmits wireless energy which is received by the first coil of the energy receiver. This system further comprises a feedback device for communicating out the amount of energy received in the first coil as a feedback information, and wherein the second electronic circuit includes a determination device for receiving the feedback information and for comparing the amount of transferred energy by the second coil with the feedback information related to the amount of energy received in the first coil to obtain the coupling factor between the first and second coils. The energy transmitter may regulate the transmitted energy in response to the obtained coupling factor.

Figure 51:
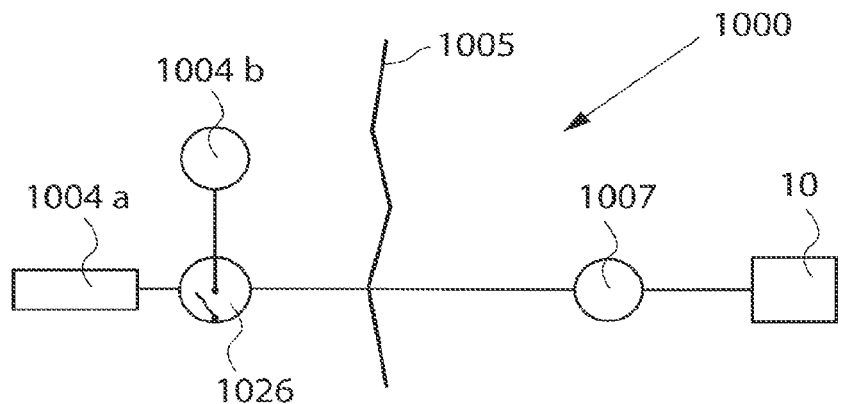
FIG. 51 schematically shows an embodiment of the system, in which the apparatus is operated with wire bound energy.

With reference to FIG. 51, although wireless transfer of energy for operating the apparatus has been described above to enable non-invasive operation, it will be appreciated that the apparatus can be operated with wire bound energy as well. Such an example is shown in FIG. 51, wherein an external switch 1026 is interconnected between the external energy source 1004*a* and an operation device, such as an electric motor 1007 operating the apparatus 10. An external control unit 1004*b* controls the operation of the external switch 1026 to effect proper operation of the apparatus 10.

FIG. 52 illustrates different embodiments for how received energy can be supplied to and used by the apparatus 10. Similar to the example of FIG. 50, an internal energy receiver 1002 receives wireless energy E from an external energy source 1004*a* which is controlled by a transmission control unit 1004*b*. The internal energy receiver 1002 may comprise a constant voltage circuit, indicated as a dashed box "constant V" in the figure, for supplying energy at constant voltage to the apparatus 10. The internal energy receiver 1002 may further comprise a constant current circuit, indicated as a dashed box "constant C" in the figure, for supplying energy at constant current to the apparatus 10.

The apparatus 10 comprises an energy consuming part 10*a*, which may be a motor, pump, restriction device, or any other medical appliance that requires energy for its electrical operation. The apparatus 10 may further comprise an energy storage device 10*b* for storing energy supplied from the internal energy receiver 1002. Thus, the supplied energy may be directly consumed by the energy consuming part 10*a*, or stored by the energy storage device 10*b*, or the supplied energy may be partly consumed and partly stored. The apparatus 10 may further comprise an energy stabilizing unit 10*c* for stabilizing the energy supplied from the internal energy receiver 1002. Thus, the energy may be supplied in a fluctuating manner such that it may be necessary to stabilize the energy before consumed or stored.

The energy supplied from the internal energy receiver 1002 may further be accumulated and/or stabilized by a separate energy stabilizing unit 1028 located outside the apparatus 10, before being consumed and/or stored by the apparatus 10. Alternatively, the energy stabilizing unit 1028 may be integrated in the internal energy receiver 1002. In either case, the energy stabilizing unit 1028 may comprise a constant voltage circuit and/or a constant current circuit.

It should be noted that FIG. 50 and FIG. 52 illustrate some possible but non-limiting implementation options regarding how the various shown functional components and elements can be arranged and connected to each other. However, the skilled person will readily appreciate that many variations and modifications can be made within the scope of the present invention.

Figure 53:
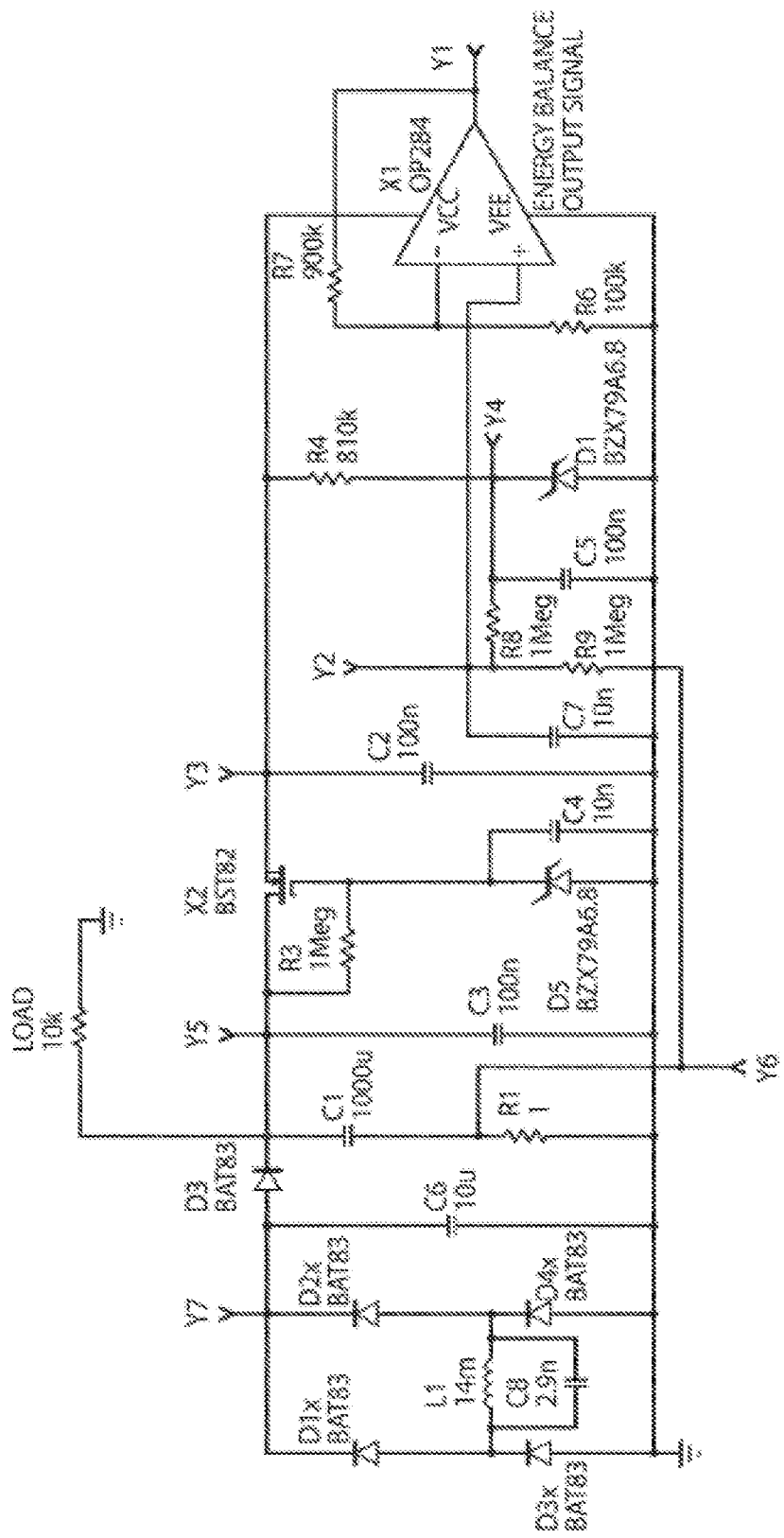
FIG. 53 is a circuit for the arrangement shown in FIG. 52, according to a possible implementation example.

FIG. 53 schematically shows an energy balance measuring circuit of one of the proposed designs of the system for controlling transmission of wireless energy, or energy balance control system. The circuit has an output signal centered on 2.5V and proportionally related to the energy imbalance. The derivative of this signal shows if the value goes up and down and how fast such a change takes place. If the amount of received energy is lower than the energy used by implanted components of the apparatus, more energy is transferred and thus charged into the energy source. The output signal from the circuit is typically feed to an A/D converter and converted into a digital format. The digital information can then be sent to the external energy-transmission device allowing it to adjust the level of the transmitted energy. Another possibility is to have a completely analog system that uses comparators comparing the energy balance level with certain maximum and minimum thresholds sending information to external energy-transmission device if the balance drifts out of the max/min window.

The schematic FIG. 53 shows a circuit implementation for a system that transfers energy to the implanted energy components of the apparatus of the present invention from outside of the patient's body using inductive energy transfer. An inductive energy transfer system typically uses an external transmitting coil and an internal receiving coil. The receiving coil, L1, is included in the schematic FIG. 36; the transmitting parts of the system are excluded.

The implementation of the general concept of energy balance and the way the information is transmitted to the external energy transmitter can of course be implemented in numerous different ways. The schematic FIG. 53 and the above described method of evaluating and transmitting the information should only be regarded as examples of how to implement the control system.

Circuit Details

In FIG. 53 the symbols Y1, Y2, Y3 and so on symbolize test points within the circuit. The components in the diagram and their respective values are values that work in this particular implementation which of course is only one of an infinite number of possible design solutions.

Energy to power the circuit is received by the energy receiving coil L1. Energy to implanted components is transmitted in this particular case at a frequency of 25 kHz. The energy balance output signal is present at test point Y1.

Those skilled in the art will realize that the above various embodiments of the system could be combined in many different ways. For example, the electric switch 1006 of FIG. 36 could be incorporated in any of the embodiments of FIGS. 39-45, the hydraulic valve shifting device 1014 of FIG. 39 could be incorporated in the embodiment of FIG. 38, and the gear box 1024 could be incorporated in the embodiment of FIG. 37. Please observe that the switch simply could mean any electronic circuit or component.

The embodiments described in connection with FIGS. 50, 52 and 53 identify a method and a system for controlling transmission of wireless energy to implanted energy consuming components of an electrically operable apparatus. Such a method and system will be defined in general terms in the following.

A method is thus provided for controlling transmission of wireless energy supplied to implanted energy consuming components of an apparatus as described above. The wireless energy E is transmitted from an external energy source located outside the patient and is received by an internal energy receiver located inside the patient, the internal energy receiver being connected to the implanted energy consuming components of the apparatus for directly or indirectly supplying received energy thereto. An energy balance is determined between the energy received by the internal energy receiver and the energy used for the apparatus. The transmission of wireless energy E from the external energy source is then controlled based on the determined energy balance.

The wireless energy may be transmitted inductively from a primary coil in the external energy source to a secondary coil in the internal energy receiver. A change in the energy balance may be detected to control the transmission of wireless energy based on the detected energy balance change. A difference may also be detected between energy received by the internal energy receiver and energy used for the medical device, to control the transmission of wireless energy based on the detected energy difference.

When controlling the energy transmission, the amount of transmitted wireless energy may be decreased if the detected energy balance change implies that the energy balance is increasing, or vice versa. The decrease/increase of energy transmission may further correspond to a detected change rate.

The amount of transmitted wireless energy may further be decreased if the detected energy difference implies that the received energy is greater than the used energy, or vice versa. The decrease/increase of energy transmission may then correspond to the magnitude of the detected energy difference.

As mentioned above, the energy used for the medical device may be consumed to operate the medical device, and/or stored in at least one energy storage device of the medical device.

When electrical and/or physical parameters of the medical device and/or physical parameters of the patient are determined, the energy may be transmitted for consumption and storage according to a transmission rate per time unit which is determined based on said parameters. The total amount of transmitted energy may also be determined based on said parameters.

When a difference is detected between the total amount of energy received by the internal energy receiver and the total amount of consumed and/or stored energy, and the detected difference is related to the integral over time of at least one measured electrical parameter related to said energy balance, the integral may be determined for a monitored voltage and/or current related to the energy balance.

When the derivative is determined over time of a measured electrical parameter related to the amount of consumed and/or stored energy, the derivative may be determined for a monitored voltage and/or current related to the energy balance.

The transmission of wireless energy from the external energy source may be controlled by applying to the external energy source electrical pulses from a first electric circuit to transmit the wireless energy, the electrical pulses having leading and trailing edges, varying the lengths of first time intervals between successive leading and trailing edges of the electrical pulses and/or the lengths of second time intervals between successive trailing and leading edges of the electrical pulses, and transmitting wireless energy, the transmitted energy generated from the electrical pulses having a varied power, the varying of the power depending on the lengths of the first and/or second time intervals.

In that case, the frequency of the electrical pulses may be substantially constant when varying the first and/or second time intervals. When applying electrical pulses, the electrical pulses may remain unchanged, except for varying the first and/or second time intervals. The amplitude of the electrical pulses may be substantially constant when varying the first and/or second time intervals. Further, the electrical pulses may be varied by only varying the lengths of first time intervals between successive leading and trailing edges of the electrical pulses.

A train of two or more electrical pulses may be supplied in a row, wherein when applying the train of pulses, the train having a first electrical pulse at the start of the pulse train and having a second electrical pulse at the end of the pulse train, two or more pulse trains may be supplied in a row, wherein the lengths of the second time intervals between successive trailing edge of the second electrical pulse in a first pulse train and leading edge of the first electrical pulse of a second pulse train are varied.

When applying the electrical pulses, the electrical pulses may have a substantially constant current and a substantially constant voltage. The electrical pulses may also have a substantially constant current and a substantially constant voltage. Further, the electrical pulses may also have a substantially constant frequency. The electrical pulses within a pulse train may likewise have a substantially constant frequency.

The circuit formed by the first electric circuit and the external energy source may have a first characteristic time period or first time constant, and when effectively varying the transmitted energy, such frequency time period may be in the range of the first characteristic time period or time constant or shorter.

A system comprising an apparatus as described above is thus also provided for controlling transmission of wireless energy supplied to implanted energy consuming components of the apparatus. In its broadest sense, the system comprises a control device for controlling the transmission of wireless energy from an energy-transmission device, and an implantable internal energy receiver for receiving the transmitted wireless energy, the internal energy receiver being connected to implantable energy consuming components of the apparatus for directly or indirectly supplying received energy thereto. The system further comprises a determination device adapted to determine an energy balance between the energy received by the internal energy receiver and the energy used for the implantable energy consuming components of the apparatus, wherein the control device controls the transmission of wireless energy from the external energy-transmission device, based on the energy balance determined by the determination device.

In one embodiment at least one battery may be a part of or replace the energy-transforming device 1002 to supply energy to the apparatus 10 over a power supply line. In one embodiment the battery is not rechargeable. In an alternative embodiment the battery is rechargeable. The battery supply may of course be placed both remote to and incorporated in the device.

Further, the system may comprise any of the following:

A primary coil in the external energy source adapted to transmit the wireless energy inductively to a secondary coil in the internal energy receiver.

The determination device is adapted to detect a change in the energy balance, and the control device controls the transmission of wireless energy based on the detected energy balance change The determination device is adapted to detect a difference between energy received by the internal energy receiver and energy used for the implantable energy consuming components of the apparatus, and the control device controls the transmission of wireless energy based on the detected energy difference.

The control device controls the external energy-transmission device to decrease the amount of transmitted wireless energy if the detected energy balance change implies that the energy balance is increasing, or vice versa, wherein the decrease/increase of energy transmission corresponds to a detected change rate.

The control device controls the external energy-transmission device to decrease the amount of transmitted wireless energy if the detected energy difference implies that the received energy is greater than the used energy, or vice versa, wherein the decrease/increase of energy transmission corresponds to the magnitude of said detected energy difference.

The energy used for the apparatus is consumed to operate the apparatus, and/or stored in at least one energy storage device of the apparatus.

Where electrical and/or physical parameters of the apparatus and/or physical parameters of the patient are determined, the energy-transmission device transmits the energy for consumption and storage according to a transmission rate per time unit which is determined by the determination device based on said parameters. The determination device also determines the total amount of transmitted energy based on said parameters.

When a difference is detected between the total amount of energy received by the internal energy receiver and the total amount of consumed and/or stored energy, and the detected difference is related to the integral over time of at least one measured electrical parameter related to the energy balance, the determination device determines the integral for a monitored voltage and/or current related to the energy balance.

When the derivative is determined over time of a measured electrical parameter related to the amount of consumed and/or stored energy, the determination device determines the derivative for a monitored voltage and/or current related to the energy balance.

The energy-transmission device comprises a coil placed externally to the human body, and an electric circuit is provided to power the external coil with electrical pulses to transmit the wireless energy. The electrical pulses have leading and trailing edges, and the electric circuit is adapted to vary first time intervals between successive leading and trailing edges and/or second time intervals between successive trailing and leading edges of the electrical pulses to vary the power of the transmitted wireless energy. As a result, the energy receiver receiving the transmitted wireless energy has a varied power.

The electric circuit is adapted to deliver the electrical pulses to remain unchanged except varying the first and/or second time intervals.

The electric circuit has a time constant and is adapted to vary the first and second time intervals only in the range of the first time constant, so that when the lengths of the first and/or second time intervals are varied, the transmitted power over the coil is varied.

The electric circuit is adapted to deliver the electrical pulses to be varied by only varying the lengths of first time intervals between successive leading and trailing edges of the electrical pulses.

The electric circuit is adapted to supplying a train of two or more electrical pulses in a row, said train having a first electrical pulse at the start of the pulse train and having a second electrical pulse at the end of the pulse train, and the lengths of the second time intervals between successive trailing edge of the second electrical pulse in a first pulse train and leading edge of the first electrical pulse of a second pulse train are varied by the first electronic circuit.

The electric circuit is adapted to provide the electrical pulses as pulses having a substantially constant height and/or amplitude and/or intensity and/or voltage and/or current and/or frequency.

The electric circuit has a time constant, and is adapted to vary the first and second time intervals only in the range of the first time constant, so that when the lengths of the first and/or second time intervals are varied, the transmitted power over the first coil are varied.

The electric circuit is adapted to provide the electrical pulses varying the lengths of the first and/or the second time intervals only within a range that includes the first time constant or that is located relatively close to the first time constant, compared to the magnitude of the first time constant.

FIGS. 54-57 show in more detail block diagrams of four different ways of hydraulically or pneumatically powering an implanted apparatus according to the invention.

Figure 54:
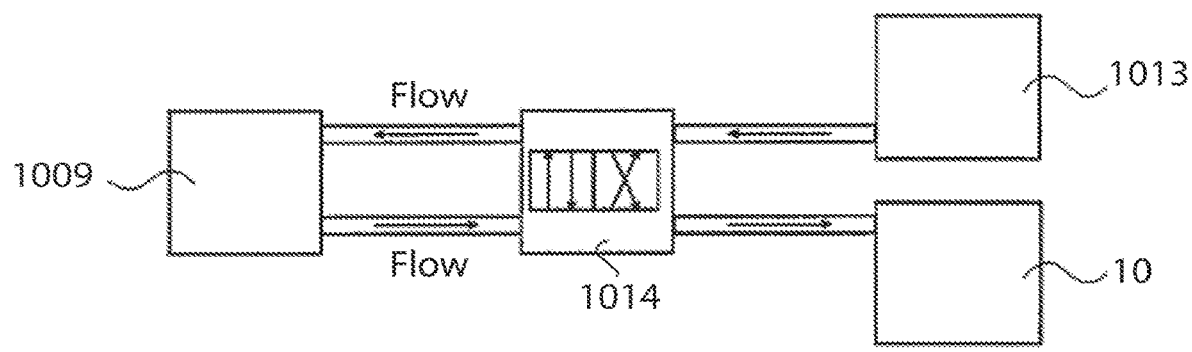
FIGS. 54-60c show various ways of arranging hydraulic or pneumatic powering of an apparatus implanted in a patient.

FIG. 54 shows a system as described above with. The system comprises an implanted apparatus 10 and further a separate regulation reservoir 1013, a one way pump 1009 and an alternate valve 1014.

Figure 55:
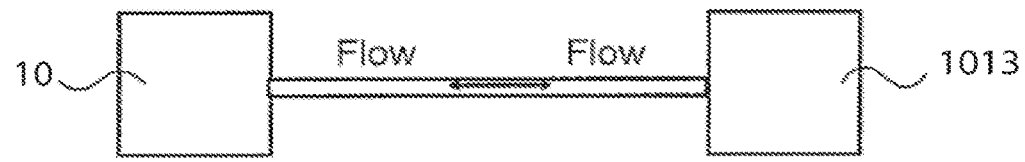

FIG. 55 shows the apparatus 10 and a fluid reservoir 1013. By moving the wall of the regulation reservoir or changing the size of the same in any other different way, the adjustment of the apparatus may be performed without any valve, just free passage of fluid any time by moving the reservoir wall.

Figure 56:
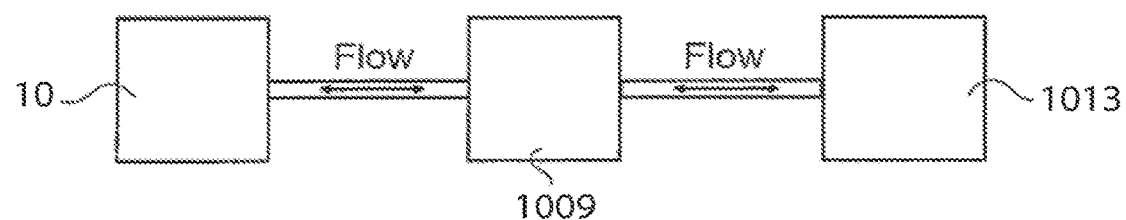

FIG. 56 shows the apparatus 10, a two way pump 1009 and the regulation reservoir 1013.

Figure 57:
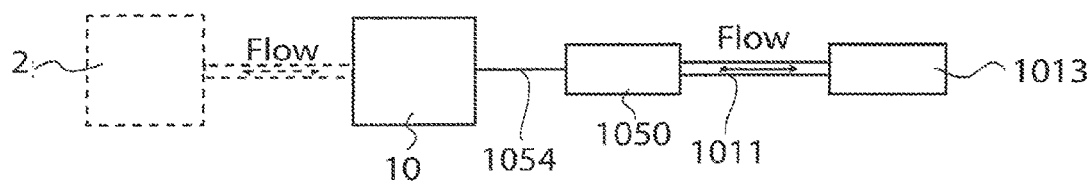

FIG. 57 shows a block diagram of a reversed servo system with a first closed system controlling a second closed system. The servo system comprises a regulation reservoir 1013 and a servo reservoir 1050. The servo reservoir 1050 mechanically controls an implanted apparatus 10 via a mechanical interconnection 1054. The apparatus has an expandable/contactable cavity. This cavity is preferably expanded or contracted by supplying hydraulic fluid from the larger adjustable reservoir 1052 in fluid connection with the apparatus 10. Alternatively, the cavity contains compressible gas, which can be compressed and expanded under the control of the servo reservoir 1050.

The servo reservoir 1050 can also be part of the apparatus itself.

Figure 58A:
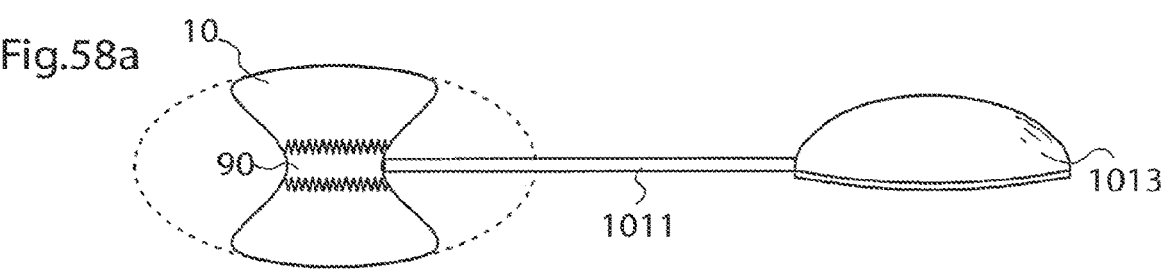
Figure 58B:
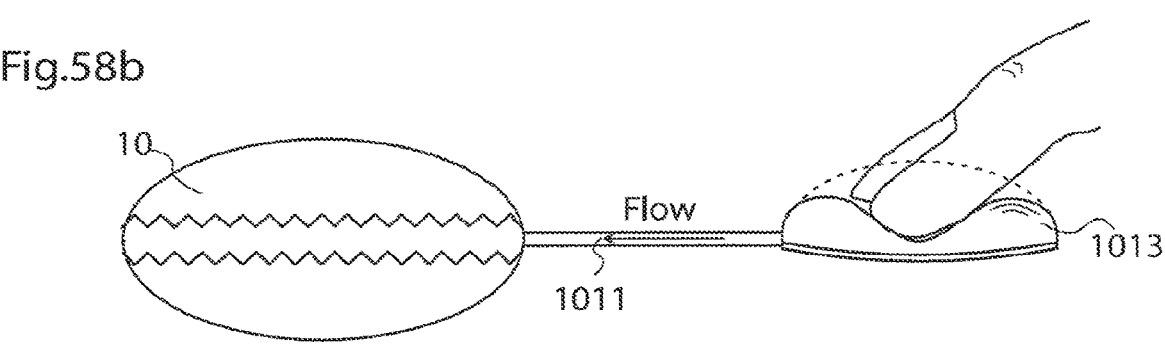
Figure 58C:
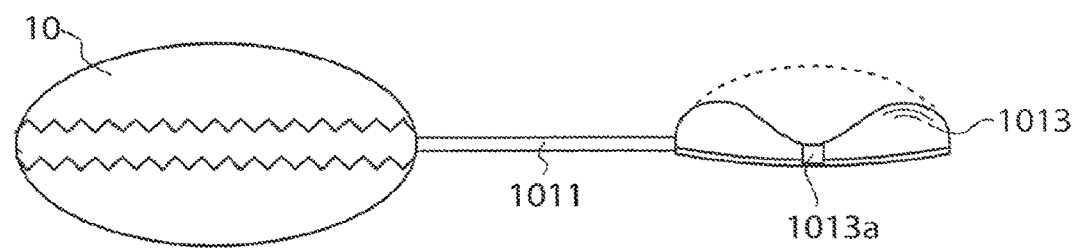
Figure 59:
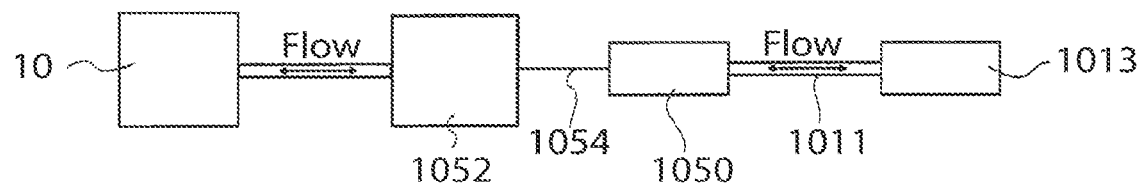

In one embodiment, the regulation reservoir is placed subcutaneous under the patient's skin and is operated by pushing the outer surface thereof by means of a finger. This system is illustrated in FIGS. 58*a-c*. In FIG. 58*a*, a flexible subcutaneous regulation reservoir 1013 is shown connected to a bulge shaped servo reservoir 1050 by means of a conduit 1011. This bellow shaped servo reservoir 1050 is comprised in a flexible apparatus 10. In the state shown in FIG. 58*a*, the servo reservoir 1050 contains a minimum of fluid and most fluid is found in the regulation reservoir 1013. Due to the mechanical interconnection between the servo reservoir 1050 and the apparatus 10, the outer shape of the apparatus 10 is contracted, i.e., it occupies less than its maximum volume. This maximum volume is shown with dashed lines in the figure.

FIG. 58*b* shows a state wherein a user, such as the patient in with the apparatus is implanted, presses the regulation reservoir 1013 so that fluid contained therein is brought to flow through the conduit 1011 and into the servo reservoir 1050, which, thanks to its bellow shape, expands longitudinally. This expansion in turn expands the apparatus 10 so that it occupies its maximum volume, thereby stretching the stomach wall (not shown), which it contacts.

The regulation reservoir 1013 is preferably provided with means 1013*a* for keeping its shape after compression. This means, which is schematically shown in the figure, will thus keep the apparatus 10 in a stretched position also when the user releases the regulation reservoir. In this way, the regulation reservoir essentially operates as an on/off switch for the system.

An alternative embodiment of hydraulic or pneumatic operation will now be described with reference to FIGS. 59 and 60*a-c*. The block diagram shown in FIG. 59 comprises with a first closed system controlling a second closed system. The first system comprises a regulation reservoir 1013 and a servo reservoir 1050. The servo reservoir 1050 mechanically controls a larger adjustable reservoir 1052 via a mechanical interconnection 1054. An implanted apparatus 10 having an expandable/contactable cavity is in turn controlled by the larger adjustable reservoir 1052 by supply of hydraulic fluid from the larger adjustable reservoir 1052 in fluid connection with the apparatus 10.

Figure 60A:
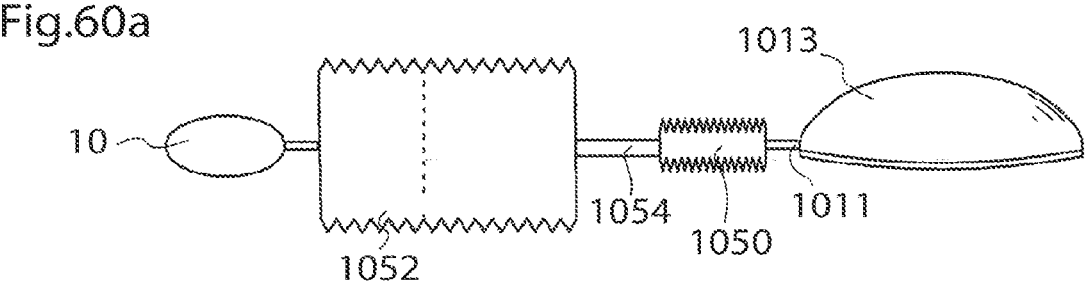
Figure 60B:
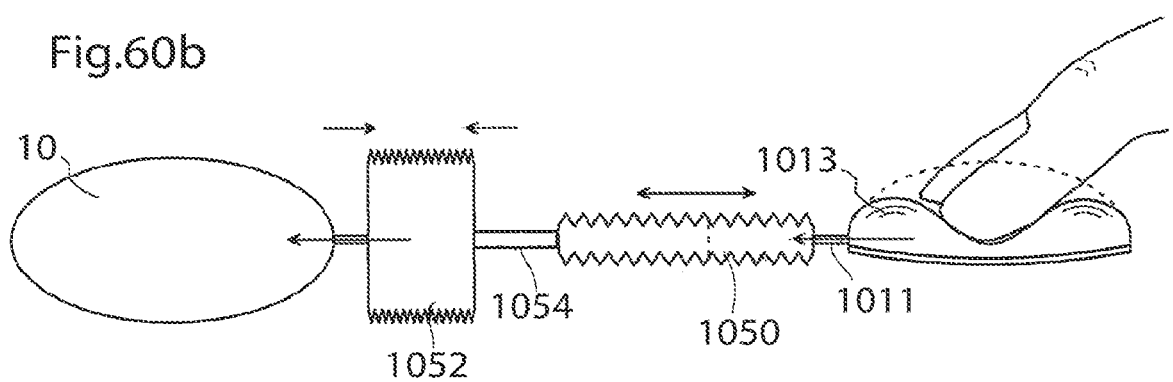
Figure 60C:
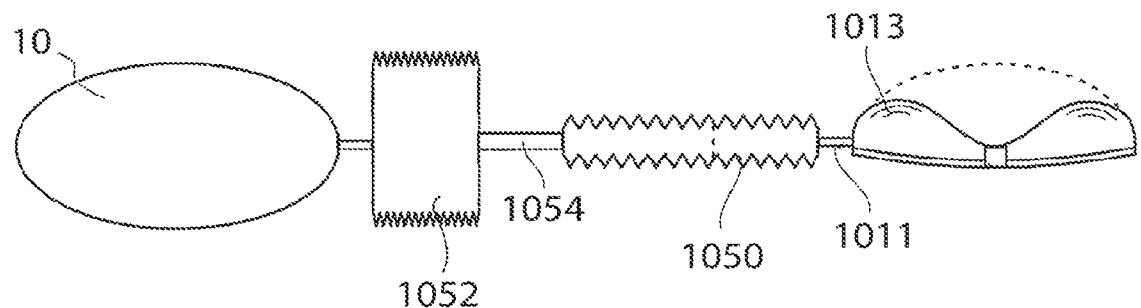

An example of this embodiment will now be described with reference to FIG. 60*a-c*. Like in the previous embodiment, the regulation reservoir is placed subcutaneous under the patient's skin and is operated by pushing the outer surface thereof by means of a finger. The regulation reservoir 1013 is in fluid connection with a bellow shaped servo reservoir 1050 by means of a conduit 1011. In the first closed system 1013, 1011, 1050 shown in FIG. 60*a*, the servo reservoir 1050 contains a minimum of fluid and most fluid is found in the regulation reservoir 1013.

The servo reservoir 1050 is mechanically connected to a larger adjustable reservoir 1052, in this example also having a bellow shape but with a larger diameter than the servo reservoir 1050. The larger adjustable reservoir 1052 is in fluid connection with the apparatus 10. This means that when a user pushes the regulation reservoir 1013, thereby displacing fluid from the regulation reservoir 1013 to the servo reservoir 1050, the expansion of the servo reservoir 1050 will displace a larger volume of fluid from the larger adjustable reservoir 1052 to the apparatus 10. In other words, in this reversed servo, a small volume in the regulation reservoir is compressed with a higher force and this creates a movement of a larger total area with less force per area unit.

Like in the previous embodiment described above with reference to FIGS. 58*a-c*, the regulation reservoir 1013 is preferably provided with means 1013*a* for keeping its shape after compression. This means, which is schematically shown in the figure, will thus keep the apparatus 10 in a stretched position also when the user releases the regulation reservoir. In this way, the regulation reservoir essentially operates as an on/off switch for the system.

Although the different parts described above have specific placements on the drawings it should be understood that these placements might vary, depending on the application.

The lubricating fluid used in any of the embodiments herein is preferably a biocompatible lubricating fluid imitating the synovial fluid of the natural hip joint. According to one embodiment the lubricating fluid is Hyaluronic acid.

In all of the embodiments above it is conceivable that the conduit is excluded and that the channel or channels are in direct connection with the reservoir or the injection port. Please note that any embodiment or part of embodiment as well as any method or part of method could be combined in any way. All examples herein should be seen as part of the general description and therefore possible to combine in any way in general terms. Please note that the description in general should be seen as describing both of an apparatus and a method.

The various aforementioned features of the invention may be combined in any way if such combination is not clearly contradictory. The invention will now be described in more detail in respect of preferred embodiments and in reference to the accompanying drawings. Again, individual features of the various embodiments may be combined or exchanged unless such combination or exchange is clearly contradictory to the overall function of the device.

The invention claimed is:

1. An implantable lubrication device for lubricating a joint of a human or mammal patient by adding a biocompatible lubrication fluid, the implantable lubrication device comprising:
   an added biocompatible lubrication fluid having lubricational properties for replacing or complementing a synovial fluid of a joint,
   an implantable refillable reservoir adapted to store the added biocompatible lubrication fluid, and
   an implantable refill injection port connected to said implantable refillable reservoir for refilling said implantable refillable reservoir with said added biocompatible lubrication fluid,
   an implantable infusion needle in fluid connection with said implantable refillable reservoir, wherein said implantable infusion needle is arranged for longitudinal displacement and has a tip end having a fluid delivery exit port,
   an implantable drive unit coupled to the implantable infusion needle and configured to advance and retract the tip end of the implantable infusion needle for injecting said added biocompatible lubrication fluid into an area of said joint, and
   a self-sealing membrane protruding from the implantable refillable reservoir and being configured to be placed in a recess in a bone adjacent to the joint and further configured to be penetrated by said infusion needle.

2. The implantable lubrication device according to claim 1, wherein said implantable infusion needle is closed at its distal end and has a lateral added biocompatible lubrication fluid delivery exit port.

3. The implantable lubrication device according to claim 1, wherein said implantable infusion needle is configured to penetrate fibrotic tissue.

4. The implantable lubrication device according to claim 1, wherein said implantable refillable reservoir has an adjustable volume.

5. The implantable lubrication device according to claim 4, wherein said implantable refillable reservoir comprises a flexible wall portion.

6. The implantable lubrication device according to claim 1, wherein said implantable refill injection port comprises a self-sealing membrane.

7. The implantable lubrication device according to claim 1, further comprising an implantable pump for pumping said added biocompatible lubrication fluid from said implantable reservoir towards said implantable infusion needle.

8. The implantable lubrication device according to claim 7, wherein said implantable pump is motor driven.

9. The implantable lubrication device according to claim 7, wherein said implantable pump comprises an automatically controlled motor configured to intermittently pump an amount of said added biocompatible lubrication fluid towards said implantable infusion needle.

10. The implantable lubrication device according to claim 7, wherein said implantable pump comprises a movable wall.

11. The implantable lubrication device according to claim 1, wherein the components of the implantable lubrication device are contained within a unitary body.

12. The implantable lubrication device according to claim 1, comprising a system for manually and non-invasively controlling the implantable lubrication device comprising an implantable switch.

13. The implantable lubrication device according to claim 1, comprising a system for manually and non-invasively controlling the implantable lubrication device comprising a wireless remote control.

14. The implantable lubrication device according to claim 1, comprising a system for manually and non-invasively controlling the implantable lubrication device comprising a hydraulic reservoir configured to be manually pressed.

15. The implantable lubrication device according to claim 1, comprising an internal energy source for powering implantable energy consuming components of the implantable lubrication device.

16. The implantable lubrication device according to claim 1, comprising an internal energy receiver, and wherein the implantable lubrication device is adapted to be energized non-invasively and wirelessly by an energy transmission device from outside the patient's body.

17. The implantable lubrication device according to claim 1, comprising at least one sensor for measuring at least one physical parameter of the patient.

18. The implantable lubrication device according to claim 1, comprising at least one sensor for measuring at least one functional parameter related to the implantable lubrication device.

19. The implantable lubrication device according to claim 18, wherein the at least one functional parameter is correlated to the transfer of energy for charging the internal energy source.

20. The implantable lubrication device according to claim 1, comprising a feedback device for sending feedback information from inside the patient's body to at least an external control unit outside of the body of the patient.

* * * * *